(12) United States Patent
Gerspacher et al.

(10) Patent No.: US 8,193,189 B2
(45) Date of Patent: Jun. 5, 2012

(54) QUINOXALINE DERIVATIVES AS TYROSINE KINASE ACTIVITY INHIBITORS

(75) Inventors: Marc Gerspacher, Basel (CH); Pascal Furet, Basel (CH); Eric Vangrevelinghe, Basel (CH); Carole Pissot Sondermann, Basel (CH); Christoph Gaul, Basel (CH); Philipp Holzer, Basel (CH)

(73) Assignee: Novartis AG, Basel (CH)

( * ) Notice: Subject to any disclaimer, the term of this patent is extended or adjusted under 35 U.S.C. 154(b) by 169 days.

(21) Appl. No.: 12/663,698

(22) PCT Filed: Jun. 6, 2008

(86) PCT No.: PCT/EP2008/057058
§ 371 (c)(1),
(2), (4) Date: Dec. 8, 2009

(87) PCT Pub. No.: WO2008/148867
PCT Pub. Date: Dec. 11, 2008

(65) Prior Publication Data
US 2010/0168062 A1    Jul. 1, 2010

(30) Foreign Application Priority Data

Jun. 8, 2007 (EP) .................................. 07109880
Dec. 20, 2007 (EP) .................................. 07150266

(51) Int. Cl.
*A61K 31/495* (2006.01)
(52) U.S. Cl. .......... 514/249; 544/62; 544/116; 544/353; 544/359; 546/199; 546/268.1; 548/335.1; 548/373.1; 548/518; 548/560; 548/950
(58) Field of Classification Search .................. 514/249; 544/62, 116, 352, 359; 546/199, 268.1; 548/335.1, 548/373.1, 518, 560, 950
See application file for complete search history.

(56) References Cited

U.S. PATENT DOCUMENTS 5,545,646 A    8/1996    Straub et al.
5,721,248 A    2/1998    Straub et al.

FOREIGN PATENT DOCUMENTS

EP       0 630 895 A1      6/1994
WO       WO 99/46260 A1    9/1999
WO       WO 2005/056547 A2 6/2005

OTHER PUBLICATIONS

Takanori et al, "Preparation, properties, and X-ray structures of 5,50-bi(8-aminoquinoxalyl)s: novel Wurster-type electron donors witha heterobiaryl skeleton", Tetrahedron Letters, 45, 2004, 329-333.

Aldakov et al; "Dipyrrolyl quinoxalines with extended chromophores are efficient fluorimetric sensors for pyrophosphate"; Chemical Communications 12:1394-1395 (2002).
Anzenbacher et al; "Materials chemistry approach to anion-sensor design"; Tetrahedron 60:11163-11168 (2004).
Denny et al; "Structure-activity relationships for the mutagenic activity of tricyclic intercalating agents in *Salmonella typhimurium*"; Mutation Research 232:233-241 (1990).
Ito et al; "New Synthesis of Quinoxaline Derivatives Based on Palladium Catalyzed Oligomerization of 1,2-Diisocyanoarenes"; Heterocycles 42(2):597-615 (1996).
Ito et al; "Asymmetric Synthesis of Helical Poly(quinoxaline-2,3-diyl)s by Palladium-Mediated Polymerization of 1,2-Diisocyanbenzenes: Effective Control of the Screw-Sense by a Binaphthyl Group at the Chain-End"; J Am Chem Soc 120(46):11890-11893 (1998).
Nicolaus; "Symbiotic Approach to Drug Design" in Decision Making in Drug Research, F Gross (ed), Plenum Press, New York pp. 173-186 (1983).
Suginome et al; "Highly Effective, Easily Accessible, Screw-Sense-Determining End Group in the Asymmetric Polymerization of 1,2-diisocyanbenzenes"; Organic Letters 4(3):351-354 (2002).
Suzuki et al; "Preparation, properties, and X-ray structures of 5,5'-bi(9-aminoquinoxalyl)s: novel Wurster-type electron donors with a heterobiaryl skeleton"; Tetrahedron Letters 45:329-333 (2004).

*Primary Examiner* — James O Wilson
*Assistant Examiner* — Douglas M Willis
(74) *Attorney, Agent, or Firm* — Laura K. Madden

(57) ABSTRACT

The present invention relates to quinoxaline compound of the formula (I):

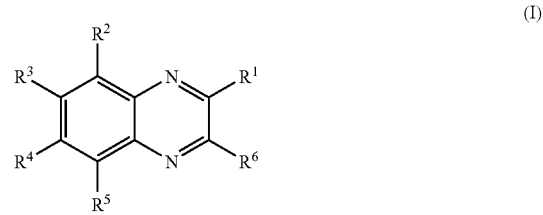

wherein
$R^1$ is carbocyclyl or heterocyclyl, either of which is optionally substituted with 1, 2, 3, 4 or 5 $R^7$;
$R^2$ is carbocyclyl or heterocyclyl, either of which is optionally substituted with 1, 2, 3, 4 or 5 $R^8$;
$R^3$, $R^4$, $R^5$ and $R^6$ are each independently hydrogen or $R^9$; and
$R^7$, $R^8$ and $R^9$ are each independently selected from organic and inorganic substituents, their use in therapy of diseases, in particular diseases mediated by the tyrosine kinase activity of Janus kinases, including JAK-2 and JAK-3 kinases.

10 Claims, No Drawings

QUINOXALINE DERIVATIVES AS TYROSINE KINASE ACTIVITY INHIBITORS

This application is a U.S. National Phase filing of International Application Serial No. PCT/EP2008/057058 filed 6 Jun. 2008 and claims priority to E.P. Application Serial No. 07109880.0 filed 8 Jun. 2007 and E.P. Application Serial No. 07150266.0 filed 20 Dec. 2007, the contents of which are incorporated herein by reference in their entirety.

FIELD OF THE INVENTION

The present invention relates to compounds, their use in therapy and to other subject matter. In particular, the present invention concerns compounds which may be useful as inhibitors of the tyrosine kinase activity of Janus kinases, including JAK-2 and JAK-3 kinases

BACKGROUND OF THE INVENTION

U.S. Pat. No. 5,721,248 and EP-A-0630895 disclose dihydropyridine compounds which are substituted at the 4-position by a bicyclic group, which may be a quinoxaline. The compounds are described as being suitable for use in the treatment of cardiovascular disease.

The 2- and 8-positions of quinoxaline are shown below:

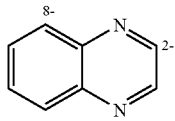

SUMMARY OF THE INVENTION

The invention provides quinoxaline compounds in which the 2- and 8-positions of the quinoxaline ring are substituted by cyclic groups. The compounds may be useful as inhibitors of the tyrosine kinase activity of Janus kinases, including JAK-2 and JAK-3 kinases. Consequently, the compounds may be useful in the therapy of proliferative diseases such as tumor diseases, leukaemias, polycythemia vera, essential thrombocythemia, and myelofibrosis with myeloid metaplasia. Through the inhibition of JAK-3 kinase, compounds of the invention also have utility as immunosuppressive agents, for example for the treatment of diseases such as organ transplant rejection, lupus, multiple sclerosis, rheumatoid arthritis, psoriasis, dermatitis, Crohn's disease, type-1 diabetes and complications from type-1 diabetes.

Compounds of the invention may exist in different forms, such as free acids, free bases, esters and other prodrugs, salts and tautomers, for example, and the claims embrace all variant forms of the compounds.

The extent of protection includes counterfeit or fraudulent products which contain or purport to contain a compound of the invention irrespective of whether they do in fact contain such a compound and irrespective of whether any such compound is contained in a therapeutically effective amount.

Included in the scope of protection are packages which include a description or instructions which indicate that the package contains a species or pharmaceutical formulation of the invention and a product which is or comprises, or purports to be or comprise, such a formulation or species. Such packages may be, but are not necessarily, counterfeit or fraudulent.

Features, integers, characteristics, compounds, chemical moieties or groups described in conjunction with a particular aspect, embodiment or example of the invention are to be understood to be applicable to any other aspect, embodiment or example described herein unless incompatible therewith.

DETAILED DESCRIPTION OF THE INVENTION

Description of Various Embodiments

Embodiments of the invention are described below. It will be appreciated that the features specified in each embodiment may be combined with other specified features, to provide further embodiments.

The term "hydrocarbyl" as used herein includes reference to a moiety consisting exclusively of hydrogen and carbon atoms; such a moiety may comprise an aliphatic and/or an aromatic moiety. The moiety may comprise 1, 2, 3, 4, 5, 6, 7, 8, 9, 10, 11, 12, 13, 14, 15, 16, 17, 18, 19 or 20 carbon atoms. Examples of hydrocarbyl groups include $C_{1-6}$ alkyl (e.g. $C_1$, $C_2$, $C_3$ or $C_4$ alkyl, for example methyl, ethyl, propyl, isopropyl, n-butyl, sec-butyl or tert-butyl); $C_{1-6}$ alkyl substituted by aryl (e.g. benzyl) or by cycloalkyl (e.g. cyclopropylmethyl); cycloalkyl (e.g. cyclopropyl, cyclobutyl, cyclopentyl or cyclohexyl); aryl (e.g. phenyl, naphthyl or fluorenyl) and the like.

The terms "alkyl" and "$C_{1-8}$ alkyl" as used herein include reference to a straight or branched chain alkyl moiety having 1, 2, 3, 4, 5, 6, 7 or 8 carbon atoms. This term includes reference to groups such as methyl, ethyl, propyl (n-propyl or isopropyl), butyl (n-butyl, sec-butyl or tert-butyl), pentyl, hexyl, heptyl, octyl and the like. In particular, alkyl may have 1, 2, 3 or 4 carbon atoms.

The terms "alkenyl" and "$C_{2-6}$ alkenyl" as used herein include reference to a straight or branched chain alkyl moiety having 2, 3, 4, 5 or 6 carbon atoms and having, in addition, at least one double bond, of either E or Z stereochemistry where applicable. This term includes reference to groups such as ethenyl, 2-propenyl, 1-butenyl, 2-butenyl, 3-butenyl, 1-pentenyl, 2-pentenyl, 3-pentenyl, 1-hexenyl, 2-hexenyl and 3-hexenyl and the like.

The terms "alkynyl" and "$C_{2-6}$ alkynyl" as used herein include reference to a straight or branched chain alkyl moiety having 2, 3, 4, 5 or 6 carbon atoms and having, in addition, at least one triple bond. This term includes reference to groups such as ethynyl, 1-propynyl, 2-propynyl, 1-butynyl, 2-butynyl, 3-butynyl, 1-pentynyl, 2-pentynyl, 3-pentynyl, 1-hexynyl, 2-hexynyl and 3-hexynyl and the like.

The terms "alkoxy" and "$C_{1-6}$ alkoxy" as used herein include reference to —O-alkyl, wherein alkyl is straight or branched chain and comprises 1, 2, 3, 4, 5 or 6 carbon atoms. In one class of embodiments, alkoxy has 1, 2, 3 or 4 carbon atoms. This term includes reference to groups such as methoxy, ethoxy, propoxy, isopropoxy, butoxy, tert-butoxy, pentoxy, hexoxy and the like.

The term "cycloalkyl" as used herein includes reference to an alicyclic moiety having 3, 4, 5, 6, 7 or 8 carbon atoms. The group may be a bridged or polycyclic ring system. More often cycloalkyl groups are monocyclic. This term includes reference to groups such as cyclopropyl, cyclobutyl, cyclopentyl, cyclohexyl, norbornyl, bicyclo[2.2.2]octyl and the like.

The term "aryl" as used herein includes reference to an aromatic ring system comprising 6, 7, 8, 9, 10, 11, 12, 13, 14, 15 or 16 ring carbon atoms. Aryl is often phenyl but may be a polycyclic ring system, having two or more rings, at least one of which is aromatic. This term includes reference to groups such as phenyl, naphthyl, fluorenyl, azulenyl, indenyl, anthryl and the like.

The term "carbocyclyl" as used herein includes reference to a saturated (e.g. cycloalkyl) or unsaturated (e.g. aryl) ring moiety having 3, 4, 5, 6, 7, 8, 9, 10, 11, 12, 13, 14, 15 or 16 carbon ring atoms. In particular, carbocyclyl includes a 3- to 10-membered ring or ring system and, in particular, a 5- or 6-membered ring, which may be saturated or unsaturated. A carbocyclic moiety is, for example, selected from cyclopropyl, cyclobutyl, cyclopentyl, cyclohexyl, norbornyl, bicyclo[2.2.2]octyl, phenyl, naphthyl, fluorenyl, azulenyl, indenyl, anthryl and the like.

The term "heterocyclyl" as used herein includes reference to a saturated (e.g. heterocycloalkyl) or unsaturated (e.g. heteroaryl) heterocyclic ring moiety having from 3, 4, 5, 6, 7, 8, 9, 10, 11, 12, 13, 14, 15 or 16 ring atoms, at least one of which is selected from nitrogen, oxygen, phosphorus, silicon and sulphur. In particular, heterocyclyl includes a 3- to 10-membered ring or ring system and more particularly a 5- or 6-membered ring, which may be saturated or unsaturated.

A heterocyclic moiety is, for example, selected from oxiranyl, azirinyl, 1,2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, β-carbolinyl, phenanthridinyl, acridinyl, perimidinyl, phenanthrolinyl, furazanyl, phenazinyl, phenothiazinyl, phenoxazinyl, chromenyl, isochromanyl, chromanyl and the like.

The term "heterocycloalkyl" as used herein includes reference to a saturated heterocyclic moiety having 3, 4, 5, 6 or 7 ring carbon atoms and 1, 2, 3, 4 or 5 ring heteroatoms selected from nitrogen, oxygen, phosphorus and sulphur. The group may be a polycyclic ring system but more often is monocyclic. This term includes reference to groups such as azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl and the like.

The term "heteroaryl" as used herein includes reference to an aromatic heterocyclic ring system having 5, 6, 7, 8, 9, 10, 11, 12, 13, 14, 15 or 16 ring atoms, at least one of which is selected from nitrogen, oxygen and sulphur. The group may be a polycyclic ring system, having two or more rings, at least one of which is aromatic, but is more often monocyclic. This term includes reference to groups such as pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, purinyl, isoquinolinyl, quinazolinyl, pteridinyl and the like.

The term "halogen" as used herein includes reference to F, Cl, Br or I. In particular, halogen may be F or Cl, of which F is more common.

The term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted" as used herein means substituted or unsubstituted. It will, of course, be understood that substituents are only at positions where they are chemically possible, the person skilled in the art being able to decide (either experimentally or theoretically) without inappropriate effort whether a particular substitution is possible. For example, amino or hydroxy groups with free hydrogen may be unstable if bound to carbon atoms with unsaturated (e.g. olefinic) bonds. Additionally, it will of course be understood that the substituents described herein may themselves be substituted by any substituent, subject to the aforementioned restriction to appropriate substitutions as recognised by the skilled man.

The term "pharmaceutically acceptable" as used herein includes reference to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio. This term includes acceptability for both human and veterinary purposes.

Where two or more moieties are described as being "each independently" selected from a list of atoms or groups, this means that the moieties may be the same or different. The identity of each moiety is therefore independent of the identities of the one or more other moieties.

The invention provides quinoxaline compounds in which the 2- and 8-positions of the quinoxaline ring are substituted by cyclic groups. The cyclic groups may be the same or different and may be substituted or unsubstituted. In embodiments, the cyclic groups are carbocyclyl or heterocyclyl and are substituted or unsubstituted.

Included in the invention are quinoxaline compounds of the formula (I):

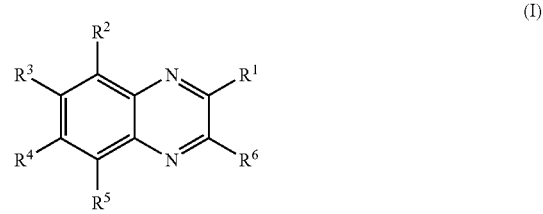

(I)

wherein
R$^1$ is carbocyclyl or heterocyclyl, either of which is optionally substituted with 1, 2, 3, 4 or 5 R$^7$;
R$^2$ is carbocyclyl or heterocyclyl, either of which is optionally substituted with 1, 2, 3, 4 or 5 R$^8$;
R$^3$, R$^4$, R$^5$ and R$^6$ are each independently hydrogen or R$^9$; and
R$^7$, R$^8$ and R$^9$ are each independently selected from organic and inorganic substituents;
or a pharmaceutically acceptable salt or prodrug thereof.
R$^1$ According to formula (I), R$^1$ is carbocyclyl or heterocyclyl, either of which is optionally substituted with 1, 2, 3, 4 or 5 R$^7$.

In one embodiment, R$^1$ comprises a monocyclic ring having 3, 4, 5, 6 or 7 ring members. Alternatively, R$^1$ may comprise a fused ring system comprising 2 or more fused rings, for example two fused rings having 5 or 6 ring members.

In a particular embodiment, $R^1$ is a 5- or 6-membered carbocycle or heterocycle, and is optionally substituted with 1, 2, 3, 4 or 5 $R^7$. $R^1$ may be aromatic or heteroaromatic. Alternatively, $R^1$ may be saturated group, e.g. cycloalkyl optionally substituted with 1, 2, 3, 4 or 5 $R^7$. $R^1$ may also be an unsaturated carbocyclic or unsaturated heterocyclic moiety.

Of mention are compounds in which $R^1$ is aryl (e.g. phenyl or naphthyl) or heteroaryl (e.g. pyridinyl or pyrazolyl), either of which is optionally substituted with one or more $R^7$ groups, e.g. 1, 2, 3, 4 or 5 $R^7$ groups. Compounds in which $R^1$ is phenyl optionally substituted with 1, 2, 3, 4 or 5 $R^7$ are of particular mention. Compounds in which $R^1$ is pyridinyl optionally substituted with 1, 2, 3 or 4 $R^7$ are also of particular mention. Also of particular mention are compounds in which $R^1$ is pyrazolyl optionally substituted with 1, 2 or 3 $R^7$.

In certain compounds, $R^1$ is substituted with at least 1 $R^7$, e.g. 1, 2 or 3 $R^7$. Of particular mention are compounds in which $R^1$ is phenyl or pyridinyl or pyrazolyl, each independently substituted with 1, 2 or 3 $R^7$, preferably 1 or 2 $R^7$.

Where present, the or each $R^7$ is independently selected from organic or inorganic substituents.

In certain compounds, at least one $R^7$ is independently selected from —W—$R^{10}$, wherein:
 W is a bond or a linker comprising 1 to 20 (e.g. 1 to 8) in-chain atoms and, for example, comprising one or more linkages selected from —O—, —C(O)—, —N($R^{11}$)—, hydrocarbylene optionally substituted with 1, 2, 3, 4 or 5 $R^{13}$, and heterocyclylene optionally substituted with 1, 2, 3, 4 or 5 $R^{13}$;
 $R^{10}$ is selected from hydrogen, except when W is a bond; hydrocarbyl optionally substituted with 1, 2, 3, 4 or 5 $R^{13}$; and —(CH$_2$)$_k$-heterocyclyl optionally substituted with 1, 2, 3, 4 or 5 $R^{13}$;
 $R^{11}$ is selected from $R^{12}$, —O$R^{12}$, —C(O)$R^{12}$, —C(O)O$R^{12}$ and —S(O)$_l$$R^{12}$;
 $R^{12}$ is selected from hydrogen; hydrocarbyl optionally substituted with 1, 2, 3, 4 or 5 $R^{13}$; and —(CH$_2$)$_k$-heterocyclyl optionally substituted with 1, 2, 3, 4 or 5 $R^{13}$;
 $R^{13}$ is selected from $R^{14}$; hydrocarbyl optionally substituted with 1, 2, 3, 4 or 5 $R^{14}$; and —(CH$_2$)$_k$-heterocyclyl optionally substituted with 1, 2, 3, 4 or 5 $R^{14}$;
 $R^{14}$ is independently selected from halogen, trifluoromethyl, cyano, nitro, oxo, =N$R^{15}$, —O$R^{15}$, —C(O)$R^{15}$, —C(O)N($R^{15}$)$R^{16}$, —C(O)O$R^{15}$, —OC(O)$R^{15}$, —C(N$R^{15}$)N($R^{15}$)$R^{16}$, —S(O)$_l$$R^{15}$, —S(O)$_l$N($R^{15}$)$R^{16}$, —N($R^{15}$)$R^{16}$, —N($R^{15}$)N($R^{15}$)$R^{16}$, —N($R^{15}$)C(O)$R^{16}$ and —N($R^{15}$)S(O)$_l$$R^{16}$;
 $R^{15}$ and $R^{16}$ are each independently hydrogen or selected from hydrocarbyl and —(CH$_2$)$_k$-heterocyclyl, either of which is optionally substituted with 1, 2, 3, 4 or 5 substituents independently selected from halogen, cyano, amino, hydroxy, C$_{1-6}$ alkyl and C$_{1-6}$ alkoxy;
 k is 0, 1, 2, 3, 4, 5 or 6; and
 l is 0, 1, or 2.

In one embodiment, W is a bond or is selected from the following linkers:
 —$W^1$—;
 —$W^1$—$W^2$—;
 —$W^1$—$W^2$—$W^3$—;
 —$W^1$—$W^2$—$W^3$—$W^4$—; and
 —$W^1$—$W^2$—$W^3$—$W^4$—$W^5$—;
wherein $W^1$, $W^2$, $W^3$, $W^4$ and $W^5$ are each independently selected from —O—, —C(O)—, —N($R^{11}$)—, hydrocarbylene (e.g. C$_{1-6}$ alkylene) optionally substituted with 1, 2, 3, 4 or 5 $R^{13}$, and heterocyclylene optionally substituted with 1, 2, 3, 4 or 5 $R^{13}$.

Of mention are compounds in which W is —$W^1$—, —$W^1$—$W^2$— or —$W^1$—$W^2$—$W^3$—.

Also of mention are compounds in which W is a bond or a linker comprising 1, 2, 3 or 4 linkages independently selected from —O—, —C(O)—, —S(O)$_l$—, —N($R^{11}$)— and C$_{1-6}$ alkylene (e.g. methylene or ethylene) optionally substituted with 1, 2, 3, 4 or 5 $R^{13}$.

Included are compounds in which $R^{10}$ is hydrocarbyl, e.g. C$_{1-6}$ alkyl, optionally substituted with 1, 2, 3, 4 or 5 $R^{13}$. The invention also includes compounds in which $R^{10}$ is heterocyclyl optionally substituted with 1, 2, 3, 4 or 5 $R^{13}$. For example, $R^{10}$ may be a nitrogen-containing heterocycle, e.g. piperadyl (e.g. 4-piperadyl), piperazinyl or morpholinyl, optionally substituted with 1, 2, 3, 4 or 5 $R^{13}$.

In certain compounds, $R^1$ is substituted with at least one $R^7$, wherein said $R^7$ is selected from halogen (e.g. fluorine, chlorine or bromine), hydroxy, cyano, amino, —C(O)OH, C$_{1-6}$ alkyl, C$_{1-6}$ alkoxy (e.g. C$_1$, C$_2$, C$_3$ or C$_4$ alkoxy), —C(O)—C$_{1-6}$ alkyl, —C(O)O—C$_{1-6}$ alkyl, —S(O)$_l$—C$_{1-6}$ alkyl, —C(O)NH—C$_{1-6}$ alkyl, —C(O)N(C$_{1-6}$ alkyl)$_2$, —NH(C$_{1-6}$ alkyl) and —N(C$_{1-6}$ alkyl)$_2$, wherein any C$_{1-6}$ alkyl group present is optionally substituted with 1, 2, 3, 4 or 5 substituents independently selected from halogen, cyano, amino, hydroxy and C$_{1-6}$ alkoxy.

Of mention are compounds in which $R^1$ is substituted with 1, 2 or 3 $R^7$, wherein at least one $R^7$ is selected from hydroxy, C$_{1-6}$ alkyl optionally substituted with 1, 2, 3, 4 or 5 $R^{13}$, C$_{1-6}$ alkoxy optionally substituted with 1, 2, 3, 4 or 5 $R^{13}$, C$_{1-6}$ alkoxyalkyl optionally substituted with 1, 2, 3, 4 or 5 $R^{13}$, —S(O)$_l$$R^{15}$, —S(O)$_l$N($R^{15}$)$R^{16}$ and —N($R^{15}$)S(O)$_l$$R^{16}$, wherein $R^{15}$ and $R^{16}$ are typically each hydrogen or C$_{1-6}$ alkyl optionally substituted with 1, 2, 3, 4 or 5 $R^{13}$.

By way of example, $R^1$ may be phenyl substituted with 1, 2 or 3 $R^7$, wherein at least one $R^7$ is C$_{1-6}$ alkyl, e.g. C$_1$, C$_2$, C$_3$ or C$_4$ alkyl, or C$_{1-6}$ alkoxy, e.g. C$_1$, C$_2$, C$_3$ or C$_4$ alkoxy, either of which is optionally substituted with 1, 2, 3, 4 or 5 $R^{13}$. Of mention are compounds in which $R^1$ is phenyl substituted with 1, 2 or 3 $R^7$, wherein at least one $R^7$ is methyl or ethyl. Also of mention are compounds in which $R^1$ is phenyl substituted with 2 or 3 groups selected from methoxy and ethoxy. For example, $R^1$ may be selected from 3,4-dimethoxyphenyl, 3,4-diethoxyphenyl and 3,4,5-trimethoxyphenyl. Of particular mention are compounds in which $R^1$ is 3,4,5-trimethoxyphenyl.

In certain compounds $R^1$ is substituted with 1, 2, or 3 $R^7$, wherein at least one $R^7$ is —W—$R^{10}$. By way of example, $R^1$ may be phenyl substituted with 1, 2, or 3 $R^7$, wherein at least one $R^7$ is —W—$R^{10}$. Included are compounds in which said at least one $R^7$ is present at the 4-position of the phenyl ring. Said W may, for example, be a bond or a linker comprising 1, 2, 3, 4 or 5 linkages independently selected from —O—, —C(O)—, —S(O)$_l$—, —N($R^{11}$)— and C$_{1-6}$ alkylene (e.g. methylene or ethylene) optionally substituted with 1, 2, 3, 4 or 5 $R^{13}$. In certain compounds, said W is a bond. In other compounds, said W is selected from —C(O)—, C$_{1-6}$ alkylene, —O—C$_{1-6}$ alkylene- and —C$_{1-6}$ alkylene-O—, wherein the C$_{1-6}$ alkylene moieties (e.g. C$_1$, C$_2$, C$_3$ or C$_4$ alkylene) are optionally substituted with 1, 2, 3, 4 or 5 $R^{13}$. Said $R^{10}$ may, for example, be heterocyclyl, e.g. morpholinyl, pyrrolidinyl, piperidinyl, imidazolyl or piperazinyl, optionally substituted with 1, 2, 3, 4 or 5 $R^{13}$. $R^1$ may comprise one or more further $R^7$ substituents, wherein said further $R^7$ are independently selected from, for example, $C_{1-6}$ alkyl (e.g. methyl or ethyl), $C_{1-6}$ alkoxy (e.g. methoxy or ethoxy) and halogen (e.g. fluorine or chlorine).

$R^2$

According to formula (I), $R^2$ is carbocyclyl or heterocyclyl, either of which is optionally substituted with 1, 2, 3, 4 or 5 $R^8$.

In one embodiment, $R^2$ comprises a monocyclic ring having 3, 4, 5, 6 or 7 ring members. Alternatively, $R^2$ may comprise a fused ring system comprising 2 or more fused rings, for example two fused rings having 5 or 6 ring members.

In one embodiment, $R^2$ is a 5- or 6-membered carbocycle or heterocycle, and is optionally substituted with 1, 2, 3, 4 or 5 $R^8$. $R^2$ may be aromatic. Alternatively, $R^2$ may be saturated group, e.g. cycloalkyl optionally substituted with 1, 2, 3, 4 or 5 $R^7$.

Of mention are compounds in which $R^2$ is aryl (e.g. phenyl or naphthyl) or heteroaryl (e.g. pyridinyl), either of which is optionally substituted with 1, 2, 3, 4 or 5 $R^8$. Compounds in which $R^2$ is phenyl optionally substituted with 1, 2, 3, 4 or 5 $R^8$ are of particular mention.

In certain compounds, $R^2$ is substituted with at least 1, e.g. 1, 2 or 3, $R^8$. Of particular mention are compounds in which $R^2$ is phenyl substituted with 1, 2 or 3 $R^8$.

In particular compounds, $R^2$ is other than optionally substituted dihydropyridinyl.

Where present, the or each $R^8$ is independently selected from organic or inorganic substituents.

In certain compounds, at least one $R^8$ is independently selected from —Y—$R^{17}$, wherein:

Y is a bond or a linker comprising 1 to 20 (e.g. 1 to 8) in-chain atoms and, for example, comprising one or more linkages selected from O—, —C(O)—, —N($R^{11}$)—, hydrocarbylene optionally substituted with 1, 2, 3, 4 or 5 $R^{13}$, and heterocyclylene optionally substituted with 1, 2, 3, 4 or 5 $R^{13}$; and $R^{17}$ is selected from hydrogen, except when Y is a bond; hydrocarbyl optionally substituted with 1, 2, 3, 4 or 5 $R^{13}$; and —(CH$_2$)$_k$-heterocyclyl optionally substituted with 1, 2, 3, 4 or 5 $R^{13}$;

and wherein $R^{11}$ and $R^{13}$ are as defined elsewhere herein.

In one embodiment, Y is selected from the following linkers:

—$Y^1$—;
—$Y^1$—$Y^2$—;
—$Y^1$—$Y^2$—$Y^3$—;
—$Y^1$—$Y^2$—$Y^3$—$Y^4$—; and
—$Y^1$—$Y^2$—$Y^3$—$Y^4$—$Y^5$—;

wherein $Y^1, Y^2, Y^3, Y^4$ and $Y^5$ are each independently selected from —O—, —C(O)—, —S(O)$_t$—, —N($R^{11}$)—, hydrocarbylene (e.g. $C_{1-5}$ alkylene) optionally substituted with 1, 2, 3, 4 or 5 $R^{13}$, and heterocyclylene optionally substituted with 1, 2, 3, 4 or 5 $R^{13}$.

Of mention are compounds in which Y is —$Y^1$—, —$Y^1$—$Y^2$— or —$Y^1$—$Y^2$—$Y^3$—. Also of mention are compounds in which Y is a bond or a linker comprising 1, 2, 3 or 4 linkages independently selected from —O—, —C(O)—, —S(O)$_t$—, —N($R^{11}$)— and $C_{1-6}$ alkylene optionally substituted with 1, 2, 3, 4 or 5 $R^{13}$.

The invention includes compounds in which $R^{17}$ is heterocyclyl optionally substituted with 1, 2, 3, 4 or 5 $R^{13}$. Of particular mention are compounds in which $R^{17}$ is a nitrogen-containing heterocycle, e.g. piperazinyl or morpholinyl, optionally substituted with 1, 2, 3, 4 or 5 $R^{13}$.

In certain compounds, $R^2$ is substituted with at least one $R^8$, wherein said $R^8$ is selected from halogen (e.g. fluorine, chlorine or bromine), hydroxy, cyano, amino, —C(O)OH, $C_{1-6}$ alkyl, $C_{1-6}$ alkoxy (e.g. $C_1$, $C_2$, $C_3$ or $C_4$ alkoxy), —C(O)—$C_{1-6}$ alkyl, —C(O)O—$C_{1-6}$ alkyl, —S(O)$_t$—$C_{1-6}$ alkyl, —NH($C_{1-6}$ alkyl) and —N($C_{1-6}$ alkyl)$_2$, wherein any $C_{1-6}$ alkyl group present is optionally substituted with 1, 2, 3, 4 or 5 substituents independently selected from halogen, cyano, amino, hydroxy and $C_{1-6}$ alkoxy.

Of mention are compounds in which $R^2$ is substituted with 1, 2 or 3 $R^8$, wherein at least one $R^8$ comprises a group selected from —S(O)$_t$— (e.g. —S(O)$_2$—) and —N($R^{11}$)—. Included are compounds in which $R^2$ is phenyl substituted with 1, 2 or 3 $R^8$, wherein at least one $R^8$ comprises a group selected from —S(O)$_t$— (e.g. —S(O)$_2$—) and —N($R^{11}$)—. For example, said at least one $R^8$ may be —S(O)$_t$$R^{15}$, —S(O)$_t$N($R^{15}$)$R^{16}$ or —N($R^{15}$)S(O)$_t$$R^{16}$, wherein $R^{15}$ and $R^{16}$ are typically each hydrogen or $C_{1-6}$ alkyl optionally substituted with 1, 2, 3, 4 or 5 $R^{13}$.

In other compounds $R^2$ is substituted with 1, 2, or 3 $R^8$, wherein at least one $R^8$ is —Y—$R^{17}$. Included are compounds in which $R^2$ is phenyl substituted with 1, 2, or 3 $R^8$, wherein at least one $R^8$ is —Y—$R^{17}$. Included are compounds in which said at least one $R^8$ is present at the 4-position of the phenyl ring. Said Y may, for example, be a bond or a linker comprising 1, 2, 3 or 4 linkages independently selected from —O—, —C(O)—, —S(O)$_t$—, —N($R^{11}$)— and $C_{1-6}$ alkylene (e.g. methylene or ethylene) optionally substituted with 1, 2, 3, 4 or 5 $R^{13}$. In certain compounds, said Y is selected from —C(O)—, —$C_{1-6}$ alkylene-, —C(O)—$C_{1-6}$ alkylene- and —$C_{1-6}$ alkylene-C(O)—, wherein the $C_{1-6}$ alkylene (e.g. $C_1, C_2, C_3$ or $C_4$ alkylene) moieties are optionally substituted with 1, 2, 3, 4 or 5 $R^{13}$. In particular compounds, said Y is selected from —C(O)—, —CH$_2$—, —C(C$_{1-6}$ alkyl)$_2$, —C(O)—CH$_2$— and —CH$_2$—C(O)—. Said $R^{17}$ may, for example, be heterocyclyl, e.g. morpholinyl, thiomorpholinyl or piperazinyl, optionally substituted with 1, 2, 3, 4 or 5 $R^{13}$. Included are compounds in which said $R^{17}$ is 1,1-dioxido-thiomorpholinyl optionally substituted with 1, 2 or 3 $R^{13}$. Of mention are compounds in which $R^2$ is phenyl and said at least one $R^8$ is —C(O)$R^{17}$ or —CH$_2$C(O)$R^{17}$, wherein $R^{17}$ is heterocyclyl (e.g. morpholinyl, thiomorpholinyl or piperazinyl) optionally substituted with 1, 2, 3, 4 or 5 $R^{13}$. $R^2$ may comprise one or more further $R^8$ substituents, wherein said further $R^8$ are each independently selected from, for example, $C_{1-6}$ alkyl (e.g. methyl or ethyl), $C_{1-6}$ alkoxy (e.g. methoxy or ethoxy) and halogen (e.g. fluorine or chlorine).

$R^3, R^4, R^5$ & $R^6$

According to formula (I), $R^3, R^4, R^5$ and $R^6$ are each independently hydrogen or $R^9$, wherein are each independently hydrogen or $R^9$, wherein the or each $R^9$ is independently selected from organic and inorganic substituents.

In one embodiment, $R^3, R^4, R^5$ and $R^6$ are each independently hydrogen or $R^9$, wherein the or each $R^9$ is independently selected from $R^{13}$, wherein $R^{13}$ is as defined elsewhere herein.

Of mention are compounds in which $R^3, R^4, R^5$ and $R^6$ are each independently selected from hydrogen, halogen (e.g. fluorine or chlorine), cyano, hydroxy, $C_{1-8}$ alkyl and —N($R^{13}$)$R^{14}$, wherein $R^{13}$ and $R^{14}$ are each independently hydrogen or $C_{1-8}$ alkyl.

Of further mention are compounds in which $R^3$ and $R^4$ are each independently selected from hydrogen, halogen, cyano, hydroxy, $C_{1-8}$ alkyl and —N($R^{13}$)$R^{14}$; and $R^5$ and $R^6$ are each independently selected from hydrogen, hydroxy and —N($R^{13}$)$R^{14}$; and wherein $R^{13}$ and $R^{14}$ are each independently hydrogen or $C_{1-8}$ alkyl. In some compounds, $R^4$ is $C_{1-6}$ alkyl (e.g. methyl) or halogen (e.g. fluorine or chlorine)

The invention includes compounds in which at least one of $R^3, R^4, R^5$ and $R^6$ are each hydrogen. Included are compounds in which $R^3$, $R^4$ and $R^5$ are each hydrogen. Also included are compounds in which $R^6$ is hydrogen.

Of particular mention is a compound of the following formula:

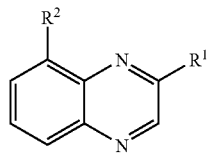

(II)

or a pharmaceutically acceptable salt or prodrug thereof.

In one embodiment, $R^1$ is substituted with at least one $R^7$, and $R^2$ is substituted with at least one $R^8$.

Also of mention is a compound of the following formula:

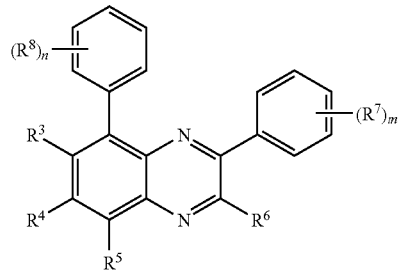

(III)

wherein m and n are each independently 1, 2, 3, 4 or 5; or a pharmaceutically acceptable salt or prodrug thereof.

Of particular mention is a compound of the following formula:

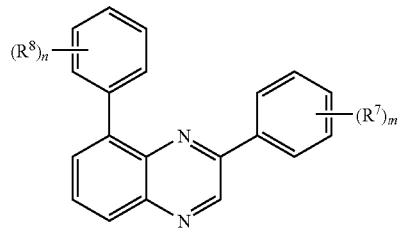

(IV)

wherein m and n are each independently 1, 2, 3, 4 or 5; or a pharmaceutically acceptable salt or prodrug thereof.

Included are compounds of said formulae in which m and n are each independently 1, 2 or 3.

In certain compounds of formulae (III) and (IV), at least one $R^7$ is selected from halogen (e.g. fluorine, chlorine or bromine), hydroxy, cyano, amino, —C(O)OH, $C_{1-6}$ alkyl, $C_{1-6}$ alkoxy (e.g. $C_1$, $C_2$, $C_3$ or $C_4$ alkoxy), —C(O)—$C_{1-6}$ alkyl, —C(O)O—$C_{1-6}$ alkyl, —S(O)$_t$—$C_{1-6}$ alkyl, —C(O)NH—$C_{1-6}$ alkyl, —C(O)N($C_{1-6}$ alkyl)$_2$, —NH($C_{1-6}$ alkyl) and —N($C_{1-6}$ alkyl)$_2$, wherein any $C_{1-6}$ alkyl group present is optionally substituted with 1, 2, 3, 4 or 5 substituents independently selected from halogen, cyano, amino, hydroxy and $C_{1-6}$ alkoxy.

In particular compounds of formulae (III) and (IV), at least one $R^7$ is selected from hydroxy, $C_{1-6}$ alkoxy optionally substituted with 1, 2, 3, 4 or 5 $R^{13}$, $C_{1-6}$ alkoxyalkyl optionally substituted with 1, 2, 3, 4 or 5 $R^{13}$, —S(O)$_t$$R^{15}$, —S(O)$_t$N($R^{15}$)$R^{18}$ and —N($R^{15}$)S(O)$_t$$R^{18}$, wherein $R^{15}$ and $R^{16}$ are typically each hydrogen or $C_{1-6}$ alkyl optionally substituted with 1, 2, 3, 4 or 5 $R^{13}$. In other compounds of formulae (III) and (IV), at least one $R^7$ is independently $C_{1-6}$ alkoxy, e.g. $C_1$, $C_2$, $C_3$ or $C_4$ alkoxy, optionally substituted with 1, 2, 3, 4 or 5 $R^{13}$.

In other compounds of said formulae, at least one $R^7$ is —W—$R^{10}$. Included are compounds in which said at least one $R^7$ is present at the 4-position of the phenyl ring. Said W may, for example, be a bond or a linker comprising 1, 2, 3 or 4 linkages independently selected from —O—, —C(O)—, —S(O)$_t$—, —N($R^{11}$)— and $C_{1-6}$ alkylene (e.g. methylene or ethylene) optionally substituted with 1, 2, 3, 4 or 5 $R^{13}$. In certain compounds, said W is a bond. In other compounds, said W is selected from —C(O)—, —O—$C_{1-6}$ alkylene-, and —$C_{1-6}$ alkylene-O—, wherein the $C_{1-6}$ alkylene (e.g. $C_1$, $C_2$, $C_3$ or $C_4$ alkylene) moieties are optionally substituted with 1, 2, 3, 4 or 5 $R^{13}$. Said $R^{10}$ may, for example, be heterocyclyl, e.g. morpholinyl, pyrrolidinyl, piperidinyl, imidazolyl or piperazinyl, optionally substituted with 1, 2, 3, 4 or 5 $R^{13}$. $R^1$ may comprise one or more further $R^7$ substituents, wherein said further $R^7$ are independently selected from, for example, $C_{1-6}$ alkyl (e.g. methyl or ethyl), $C_{1-6}$ alkoxy (e.g. methoxy or ethoxy) and halogen (e.g. fluorine or chlorine).

In certain compounds of formulae (III) and (IV), at least one $R^8$ is selected from halogen (e.g. fluorine, chlorine or bromine), hydroxy, cyano, amino, —C(O)OH, $C_{1-6}$ alkyl, $C_{1-6}$ alkoxy (e.g. $C_1$, $C_2$, $C_3$ or $C_4$ alkoxy), —C(O)—$C_{1-6}$ alkyl, —C(O)O—$C_{1-6}$ alkyl, —S(O)$_t$—$C_{1-6}$ alkyl, —NH($C_{1-6}$ alkyl), —N($C_{1-6}$ alkyl)$_2$, —C(O)NH—$C_{1-6}$ alkyl, —C(O)N($C_{1-6}$ alkyl)$_2$ and, —S(O)$_t$—$C_{1-6}$ alkyl, wherein any $C_{1-6}$ alkyl group present is optionally substituted with 1, 2, 3, 4 or 5 substituents independently selected from halogen, cyano, amino, hydroxy and $C_{1-6}$ alkoxy.

In other compounds of said formulae, at least one $R^8$ comprises a group selected from S(O)$_t$— (e.g. —S(O)$_2$—) and —N($R^{11}$)—. For example, said at least one $R^8$ may be —S(O)$_t$ $R^{15}$, —S(O)$_t$N($R^{15}$)$R^{16}$ or —N($R^{15}$)S(O)$_t$$R^{16}$, wherein $R^{15}$ and $R^{16}$ are typically each hydrogen or $C_{1-6}$ alkyl optionally substituted with 1, 2, 3, 4 or 5 $R^{13}$.

In other compounds of said formulae, at least one $R^8$ is —Y—$R^{17}$. Included are compounds in which said at least one $R^8$ is present at the 4-position of the phenyl ring. Said Y may, for example, be a bond or a linker comprising 1, 2, 3 or 4 linkages independently selected from —O—, —C(O)—, —S(O)$_t$—, —N($R^{11}$)— and $C_{1-6}$ alkylene (e.g. methylene or ethylene) optionally substituted with 1, 2, 3, 4 or 5 $R^{13}$. In certain compounds, said Y is selected from —C(O)—, —$C_{1-6}$ alkylene-, —C(O)—$C_{1-6}$ alkylene- and —$C_{1-6}$ alkylene-C(O)—, wherein the $C_{1-6}$ alkylene (e.g. $C_1$, $C_2$, $C_3$ or $C_4$ alkylene) moieties are optionally substituted with 1, 2, 3, 4 or 5 $R^{13}$. In particular compounds, said Y is selected from —C(O)—, —CH$_2$—, —C($C_{1-6}$ alkyl)$_2$, —C(O)—CH$_2$— and —CH$_2$—C(O)—. Said $R^{17}$ may, for example, be heterocyclyl, e.g. morpholinyl, thiomorpholinyl or piperazinyl, optionally substituted with 1, 2, 3, 4 or 5 $R^{13}$. Included are compounds in which said $R^{17}$ is 1,1-dioxido-thiomorpholinyl optionally substituted with 1, 2 or 3 $R^{13}$. Of mention are compounds in which said at least one $R^8$ is —C(O)$R^{17}$ or —CH$_2$C(O)$R^{17}$, wherein $R^{17}$ is heterocyclyl (e.g. morpholinyl, piperazinyl or 1,1-dioxido-thiomorpholinyl) optionally substituted with 1, 2, 3, 4 or 5 $R^{13}$. $R^2$ may comprise one or more further $R^8$ substituents, wherein said further $R^8$ are each independently selected from, for example, $C_{1-6}$ alkyl (e.g. methyl or ethyl), $C_{1-6}$ alkoxy (e.g. methoxy or ethoxy) and halogen (e.g. fluorine or chlorine).

Compounds of the invention may be in the form of pharmaceutically acceptable salts. Pharmaceutically acceptable salts can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., US, 1985, p. 1418, the disclosure of which is hereby incorporated by reference; see also Stahl et al, Eds, "Handbook of Pharmaceutical Salts Properties Selection and Use", Verlag Helvetica Chimica Acta and Wiley-VCH, 2002.

The invention thus includes pharmaceutically acceptable salts of the disclosed compounds wherein the parent compound is modified by making acid or base salts thereof. for example the conventional non-toxic salts or the quaternary ammonium salts which are formed, e.g. from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The invention includes prodrugs for the active pharmaceutical species of the invention, for example in which one or more functional groups are protected or derivatised but can be converted in vivo to the functional group, as in the case of esters of carboxylic acids convertible in vivo to the free acid, or in the case of protected amines, to the free amino group. The term "prodrug," as used herein, represents in particular compounds which are rapidly transformed in vivo to the parent compound, for example, by hydrolysis in blood. A thorough discussion is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987; H Bundgaard, ed, Design of Prodrugs, Elsevier, 1985; and Judkins, et al. Synthetic Communications, 26(23), 4351-4367 (1996), each of which is incorporated herein by reference.

Prodrugs therefore include drugs having a functional group which has been transformed into a reversible derivative thereof. Typically, such prodrugs are transformed to the active drug by hydrolysis. As examples may be mentioned the following:

| Functional Group | Reversible derivative |
|---|---|
| Carboxylic acid | Esters, including e.g. acyloxyalkyl esters, amides |
| Alcohol | Esters, including e.g. sulfates and phosphates as well as carboxylic acid esters |
| Amine | Amides, carbamates, imines, enamines, |
| Carbonyl (aldehyde, ketone) | Imines, oximes, acetals/ketals, enol esters, oxazolidines and thiazoxolidines |

Prodrugs also include compounds convertible to the active drug by an oxidative or reductive reaction. As examples of oxidative activation may be mentioned N- and O-dealkylation, oxidative deamination, N-oxidation and epoxidation. As example of reductive activation may be mentioned azo reduction, sulfoxide reduction, disulfide reduction, bioreductive alkylation and nitro reduction.

Also to be mentioned as metabolic activations of prodrugs are nucleotide activation, phosphorylation activation and decarboxylation activation. For additional information, see "The Organic Chemistry of Drug Design and Drug Action", R B Silverman (particularly Chapter 8, pages 497 to 546), incorporated herein by reference.

The use of protecting groups is fully described in 'Protective Groups in Organic Chemistry', edited by J W F McOmie, Plenum Press (1973), and 'Protective Groups in Organic Synthesis', 2nd edition, T W Greene & P G M Wutz, Wiley-Interscience (1991).

Thus, it will be appreciated by those skilled in the art that, although protected derivatives of compounds of the invention may not possess pharmacological activity as such, they may be administered, for example parenterally or orally, and thereafter metabolized in the body to form compounds of the invention which are pharmacologically active. Such derivatives are therefore examples of "prodrugs". All prodrugs of the described compounds are included within the scope of the invention.

Some groups mentioned herein (especially those containing heteroatoms and conjugated bonds) may exist in tautomeric forms and all these tautomers are included in the scope of the disclosure. More generally, many species may exist in equilibrium, as for example in the case of organic acids and their counterpart anions; a reference herein to a species accordingly includes reference to all equilibrium forms thereof.

Compounds of the invention may also contain one or more asymmetric carbon atoms and may therefore exhibit optical and/or diastereoisomerism. Such a compound may exist in optically active form or in the form of a mixture of optical isomers, e.g. in the form of a racemic mixture. All optical isomers and their mixtures, including the racemic mixtures, are part of the present invention. Thus, any given formula given herein is intended to represent a racemate, one or more enantiomeric forms, one or more diastereomeric forms, one or more atropisomeric forms, and mixtures thereof. Furthermore, certain structures may exist as geometric isomers (i.e. cis and trans isomers), as tautomers, or as atropisomers. All diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e.g. HPLC, chromatography over silica). All stereoisomers are included within the scope of the disclosure. Where a single enantiomer or diasteromer is disclosed, the disclosure also covers the other enantiomers or diastereomers, and also racemates; in this regard, particular reference is made to the specific compounds listed herein.

Geometric isomers may also exist in the compounds of the present invention. The present invention contemplates the various geometric isomers and mixtures thereof resulting from the arrangement of substituents around a carbon-carbon double bond and designates such isomers as of the Z or E configuration, wherein the term "Z" represents substituents on the same side of the carbon—carbon double bond and the term "E" represents substituents on opposite sides of the carbon—carbon double bond.

The invention therefore includes all variant forms of the defined compounds, for example any tautomer or any pharmaceutically acceptable salt, ester, acid or other variant of the defined compounds and their tautomers as well as substances which, upon administration, are capable of providing directly or indirectly a compound as defined above or providing a species which is capable of existing in equilibrium with such a compound. Furthermore, any formula given herein is intended to represent hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{125}$I respectively. Various isotopically labeled compounds of the present invention, for example those into which radioactive isotopes such as $^3$H, $^{13}$C, and $^{14}$C are incorporated. Such isotopically labelled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT) including drug or substrate tissue distribution assays, or in radioactive treatment of patients. In particular, an $^{18}$F or labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a. readily available isotopically labeled reagent for a non-isotopically labeled reagent.

Compounds of the invention may be prepared using, for example, a Suzuki (Miyaura) or analogous coupling reaction, for example a Stille reaction. By way of illustration, a compound of the invention may be prepared according to the following Schemes:

Scheme 1

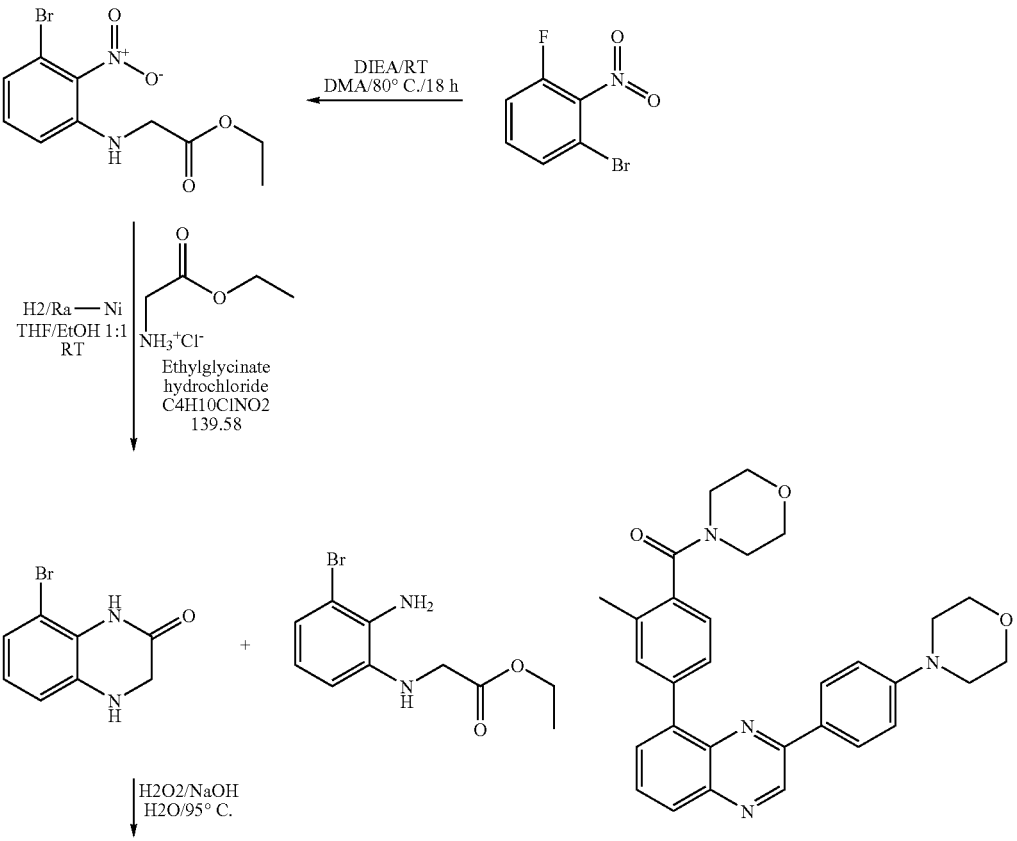

-continued
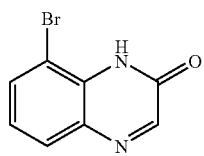
POCl3/55° C. ↓
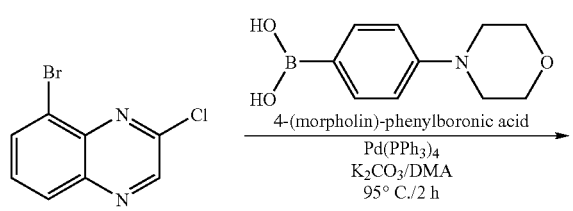
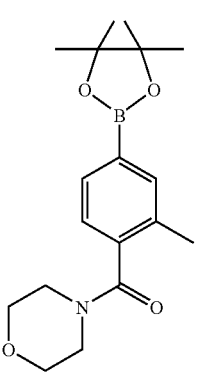
Pd(OAc)2/S-Phos
K3PO4/1,2-DME
105° C./2 h
Scheme 2
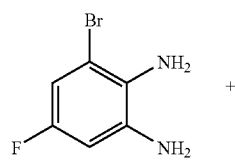
+
-continued
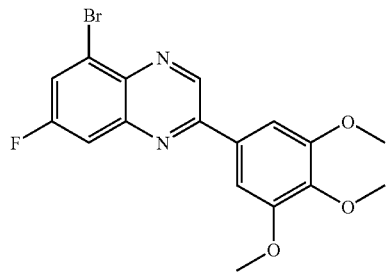
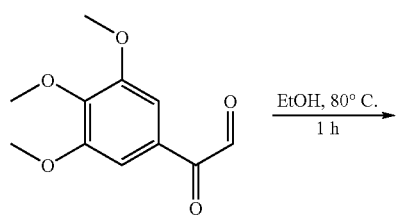
EtOH, 80° C.
1 h
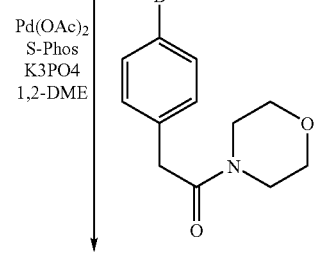
Pd(OAc)2
S-Phos
K3PO4
1,2-DME
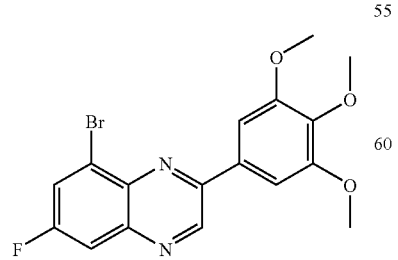
+
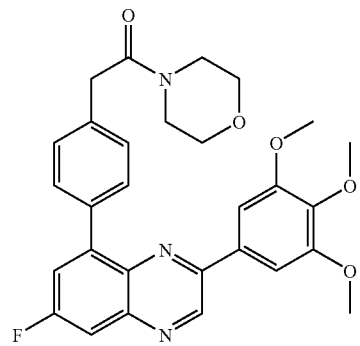

Scheme 3

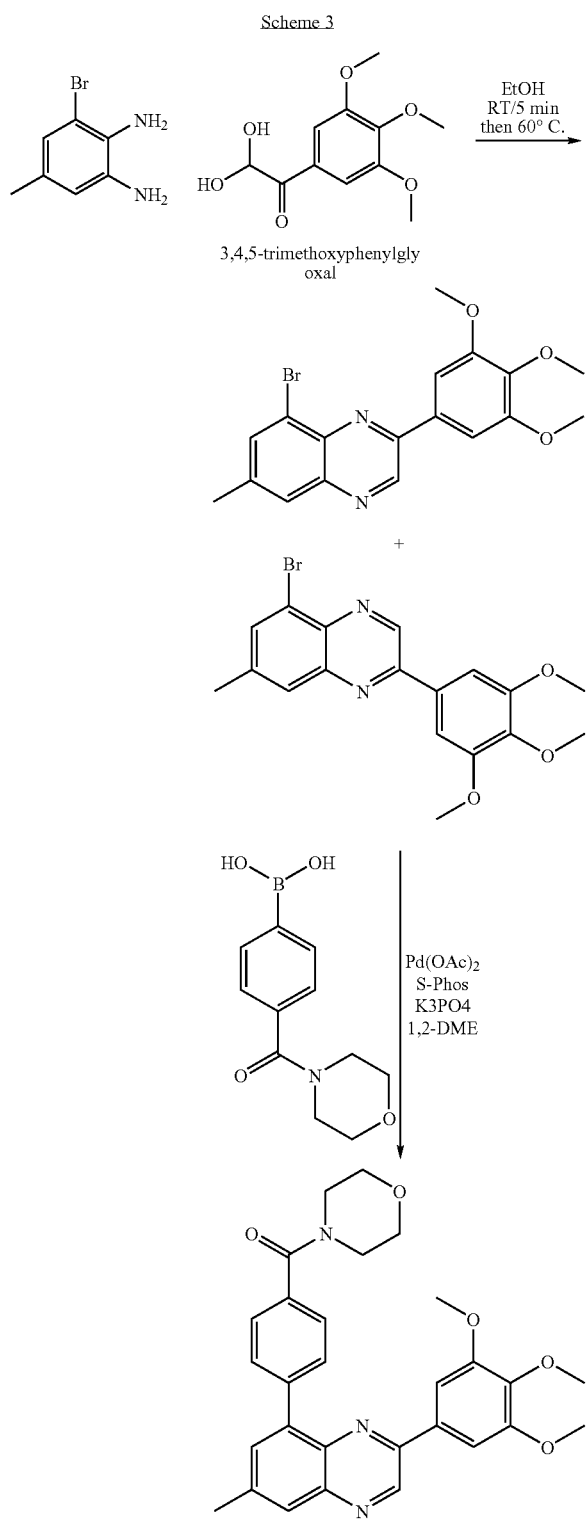

It will be understood that the processes detailed above are solely for the purpose of illustrating the invention and should not be construed as limiting. A process utilising similar or analogous reagents and/or conditions (for example, an analogous base, solvent, catalyst, ligand or reaction temperature) known to one skilled in the art may also be used to obtain a compound of the invention.

Any mixtures of final products or intermediates obtained can be separated on the basis of the physico-chemical differences of the constituents, in a known manner, into the pure final products or intermediates, for example by chromatography, distillation, fractional crystallisation, or by the formation of a salt if appropriate or possible under the circumstances.

Compounds of the invention have valuable pharmacological properties, as described hereinbefore and hereinafter. The compounds may be useful in the therapy (i.e. the treatment, prevention or delay of progression) of proliferative diseases and immunological diseases.

The invention therefore also relates to a method for the treatment of a proliferative disease in a patient, which comprises administering a compound of the invention or a pharmaceutically acceptable salt or prodrug thereof, in a quantity effective against the said disease. The patient will generally be a warm-blooded animal requiring such treatment.

The invention relates also to pharmaceutical compositions comprising an effective amount, especially an amount effective in the treatment of one of the above-mentioned disorders, of compound of the invention or a pharmaceutically acceptable salt thereof together with pharmaceutically acceptable carriers that are suitable for topical, enteral, for example oral or rectal, or parenteral administration and that may be inorganic or organic, solid or liquid. Used for oral administration can be especially tablets or gelatin capsules that comprise the active ingredient together with diluents and/or lubricants. Tablets may also comprise binders, and, if desired, disintegrators and/or effervescent mixtures, or adsorbents, dyes, flavorings and sweeteners. It is also possible to use the pharmacologically active compounds of the present invention in the form of parenterally administrable compositions or in the form of infusion solutions. The present pharmaceutical compositions, which may, if desired, comprise other pharmacologically active substances are prepared in a manner known per se, for example by means of conventional mixing, granulating, confectioning, dissolving or lyophilising processes, and comprise approximately from 1% to 95%, especially from approximately 1% to approximately 20%, active ingredient(s).

The dosage of the active ingredient to be administered may depend upon a variety of factors including type, species, age, weight, sex and medical condition of the patient; the severity of the condition to be treated; the route of administration; the renal and hepatic function of the patient; and the particular compound employed. A physician, clinician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. In general, a compound of the invention may be applied in a daily dosage between about 1 mg and 1000 mg.

Compounds of the invention may be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. A compound of formula I can besides or in addition be administered especially for tumor therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Therapeutic agents for possible combination are especially one or more antiproliferative, cytostatic or cytotoxic compounds, for example one or several agents selected from the group which includes, but is not limited to, an inhibitor of polyamine biosynthesis, an inhibitor of a protein kinase, especially of a serine/threonine protein kinase, such as protein kinase C, or of a tyrosine protein kinase, such as the EGF receptor tyrosine kinase, e.g. Iressa®, the VEGF receptor tyrosine kinase, e.g. PTK787 or Avastin®, or the PDGF receptor tyrosine kinase, e.g. STI571 (Glivec®), a cytokine, a negative growth regulator, such as TGF-β or IFN-β, an aromatase inhibitor, e.g. letrozole (Femara®) or anastrozole, an inhibitor of the interaction of an SH2 domain with a phosphorylated protein, antiestrogens, topoisomerase I inhibitors, such as irinotecan, topoisomerase II inhibitors, microtubule active agents, e.g. paclitaxel or an epothilone, alkylating agents, antiproliferative antimetabolites, such as gemcitabine or capecitabine, platin compounds, such as carboplatin or cis-platin, bisphosphonates, e.g. AREDIA® or ZOMETA®, and monoclonal antibodies, e.g. against HER2, such as trastuzumab.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

The following Examples illustrate the invention.

Abbreviations

The following abbreviations are used in the Examples:

| AcOH | Acetic acid |
| --- | --- |
| DMA | N, N-Dimethylacetamide |
| DMF | N, N-Dimethylformamide |
| EtOH | ethanol |
| H.V. | High Vacuum |
| KOAc | Potassium acetate |
| min | minutes |
| PdCl$_2$(dppf)•CH$_2$Cl$_2$ | 1,1'-bis(diphenylphosphino)ferrocenedichloropalladium(II) dichloromethane |
| PdCl$_2$(PPh$_3$)$_2$ | Bis(triphenylphosphine)palladium(II) dichloride |
| Pd(OAc)$_2$ | Palladium (II) acetate |
| Ra-Ni | Raney Nickel |
| R$_t$ | retention time |
| RT | Room temperature |
| S-Phos | 2-dicyclohexylphosphino-2',6'-dimethoxybiphenyl |
| DMAP | 4-(dimethylamino)pyridine |
| TFA | Trifluoroacetic acid |
| UPLC | Ultra Performance Liquid Chromatography |
| HPLC | High Performance Liquid Chromatography |

| HPLC Conditions | |
| --- | --- |
| A: | |
| System | Agilent 1100 Series with Waters Micromass ZQ |
| Column | XBridge C18 2.5 micron, 3 × 30 mm |
| Eluents | A: H$_2$O, B: acetonitrile, both containing 0.1% TFA |
| Flow Rate | 1.4-2.4 mL/min |
| Gradient | 10-90% B in 2.4 min |

| HPLC Conditions | |
| --- | --- |
| B: | |
| System | Agilent 1100 Series |
| Column | Macherey-Nagel CC125/4 Nucleosil 100-3 C18 HD |
| Column Temperature | 30° C. |
| Eluents | A: H$_2$O, B: acetonitrile, both containing 0.1% TFA |
| Flow Rate | 1.0 mL/min |
| Gradient | 2-100% B in 7.0 min |

Preparation of Boronic Acid and Boronic Ester Starting Compounds

The following preparations illustrate the synthesis of boronic acid or boronic esters used in the preparation of the Examples. If not specified, the boronic acids or esters are obtained from commercial source. The aryl boronic esters are prepared according to a modified procedure of Miyaura et al., J. Org. Chem. 1995, 60, 7508-7510 from their corresponding haloarenes.

Preparation 1

(4-Boronic acid-2-fluoro-phenyl)-morpholin-4-yl-methanone

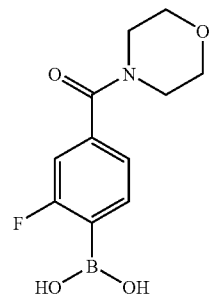

A microwave tube is charged with 1.499 g (5.2 mmol) of (4-Bromo-3-fluoro-phenyl)-morpholin-4-yl-methanone (CAS 897016-95-4), 1.48 g (5.71 mmol) bis(pinacolato)diboron, 127 mg (0.15 mmol) PdCl$_2$(dppf).CH$_2$Cl$_2$ and 1.02 g (10.4 mmol) of KOAc. After several cycle of vacuum/purge with argon, 6 ml of dry DMA are added. The reaction mixture is then heated at 80° C. for 15 h. After cooling, the reaction mixture is partitioned between EtOAc and water. The aqueous phase is re-extracted twice with water. The combined organic layers are washed with water, saturated brine, dried over Na$_2$SO$_4$, filtered and the filtrate is concentrated in vacuo to afford, after drying in HV, the title compound which is used in the next step without further purification. Note: the boronic ester is hydrolyzed into its corresponding boronic acid under the reaction condition.

Preparation 2

1-Morpholin-4-yl-2-[4-(4,4,5,5-tetramethyl-[1,3,2]dioxaborolan-2-yl)-phenyl]-ethanone

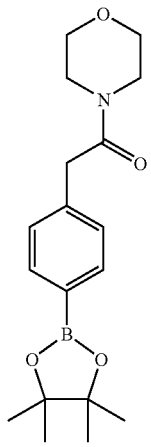

The title compound is obtained analogously to Preparation 1, but using 2-(4-Bromo-phenyl)-1-morpholin-4-yl-ethanone (CAS 349428-85-9).

Preparation 3

2-(4-Bromo-phenyl)-1-(1,1-dioxido-thiomorpholin-4-yl)-ethanone

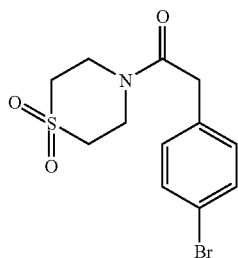

A solution of 1.17 g (5 mmol) (4-Bromo-phenyl)-acetyl chloride (CAS 37859-24-8) in 25 ml $CH_2Cl_2$ is added dropwise to a solution of 710 mg (5.25 mmol) thiomorpholine 1,1-dioxide in 25 ml $CH_2Cl_2$. After complete addition, the reaction mixture is partitioned between water and $CH_2Cl_2$. The aqueous phase is re-extracted twice with $CH_2Cl_2$. The combined organic solution is washed with brine, dried over $Na_2SO_4$ and concentrated in vacuo to afford the title compound as a light yellow residue.

Preparation 4

1-(1,1-Dioxido-thiomorpholin-4-yl)-2-[4-(4,4,5,5-tetramethyl-[1,3,2]dioxaborolan-2-yl)-phenyl]-ethanone

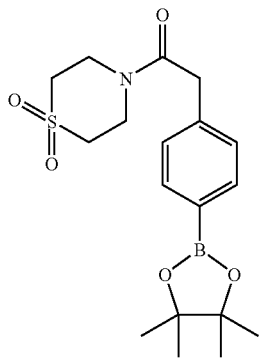

The title compound is obtained analogously to Preparation 1, but using 2-(4-Bromo-phenyl)-1-(1,1-dioxido-thiomorpholin-4-yl)-ethanone (as prepared in Preparation 3).

Preparation 5

1-(4-Methyl-piperazin-1-yl)-2-[4-(4,4,5,5-tetramethyl-[1,3,2]dioxaborolan-2-yl)-phenyl]-ethanone

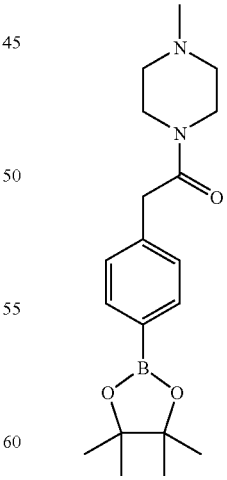

The title compound is obtained analogously to Preparation 1, but using 2-(4-Bromo-phenyl)-1-(4-methyl-piperazin-1-yl)-ethanone (CAS 349430-56-4).

Preparation 6

[2-Methyl-4-(4,4,5,5-tetramethyl-[1,3,2]dioxaborolan-2-yl)-phenyl]-morpholin-4-yl-methanone

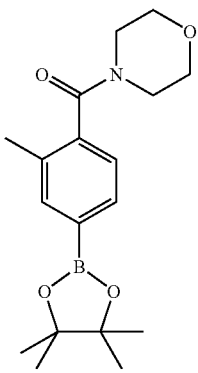

The title compound is obtained analogously to Preparation 1, but using (4-Bromo-2-methyl-phenyl)-morpholin-4-yl-methanone (CAS 276677-17-9)

Preparation 7

(4-Bromo-2-fluoro-phenyl)-morpholin-4-yl-methanone

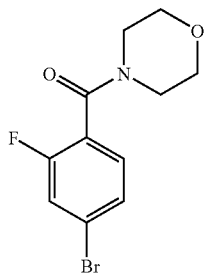

A solution of 3.8 ml (44 mmol) oxalyl chloride in 30 ml $CH_2Cl_2$ is added dropwise to a iced-cooled solution of 4.88 g (21.9 mmol) 4-bromo-2-fluorobenzoic acid in 180 ml $CH_2Cl_2$. After complete addition, the cooling bath is removed and stirring maintained for 15 h at RT. The solvent is evaporated to dryness, the resultant colorless residue is dried under vacuum and then diluted with 80 ml $CH_2Cl_2$. This solution of 2-Fluoro-4-bromobenzoyl chloride (CAS 151982-51-3) is then added dropwise to a mixture of 9.55 ml (54.7 mmol) of diisopropylethylamine, 2.01 ml (23 mmol) of morpholine in 100 ml $CH_2Cl_2$. After 1 h 30, the reaction mixture is diluted with water and the two phases are separated. The aqueous phase is re-extracted with $CH_2Cl_2$ and the combined organic extracts are washed with water, saturated brine, dried over $Na_2SO_4$, filtered and the filtrate is concentrated in vacuo to afford, after drying in HV, the title compound which is used in the next step without further purification.

Preparation 8

[2-Fluoro-4-(4,4,5,5-tetramethyl-[1,3,2]dioxaborolan-2-yl)-phenyl]-morpholin-4-yl-methanone

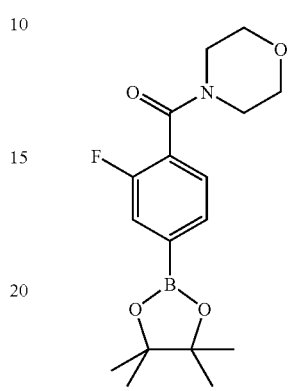

The title compound is obtained analogously to Preparation 1, but using (4-Bromo-2-fluoro-phenyl)-morpholin-4-yl-methanone (as obtained in preparation 7)

Preparation 9

4-(4-Bromo-benzyl)-thiomorpholine-1,1-dioxide

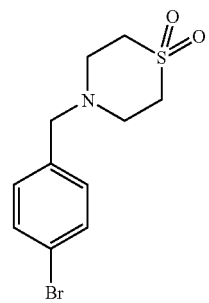

2.18 ml (15.5 mmol) of triethylamine are added to a colorless suspension of 1.28 g (5 mmol) of 4-bromobenzyl bromide and 944 mg (5.5 mmol) thiomorpholine-1,1-dioxide hydrochloride in 15 ml DMF. After 3 h at RT, the reaction mixture is partitioned between $CH_2Cl_2$ and $H_2O$. The aqueous phase is re-extracted four times with $CH_2Cl_2$. The combined organic extracts are washed with water, dried over $Na_2SO_4$, filtered and the filtrate is concentrated in vacuo to afford, after drying in HV, the title compound which is used in the next step without further purification.

Preparation 10

4-[4-(4,4,5,5-Tetramethyl-[1,3,2]dioxaborolan-2-yl)-benzyl]-thiomorpholine 1,1-dioxide

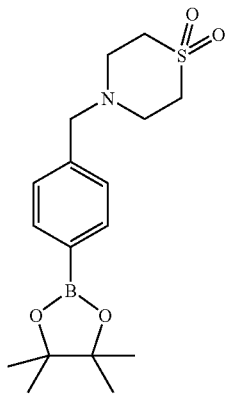

The title compound is obtained analogously to Preparation 1, but using 4-(4-Bromo-benzyl)-thiomorpholine-1,1-dioxide (as obtained in preparation 9).

Preparation 11

4-[2-Fluoro-4-(4,4,5,5-tetramethyl-[1,3,2]dioxaborolan-2-yl)-benzyl]-morpholine

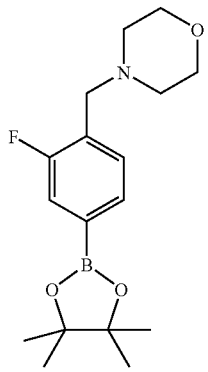

The title compound is obtained analogously to Preparation 1, but using 4-(4-Bromo-2-fluoro-benzyl)-morpholine (CAS 338454-98-1).

Preparation 12

(4-Bromo-2-methyl-phenyl)-(4-methyl-piperazin-1-yl)-methanone

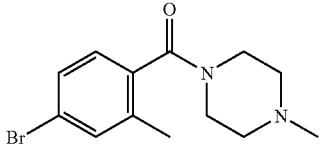

A solution of 0.850 ml (10 mmol) oxalyl chloride in 20 ml $CH_2Cl_2$ is added dropwise to a iced-cooled solution of 1.10 g (5 mmol) 4-bromo-2-methylbenzoic acid in 30 ml $CH_2Cl_2$. After complete addition, the cooling bath is removed and stirring maintained for 1 h at RT. The solvent is evaporated to dryness, the resultant colorless residue is dried under vacuum and then diluted with 25 ml $CH_2Cl_2$. This solution is then added dropwise to a mixture of 1.01 g (10 mmol) of N-methylpiperazine in 25 ml $CH_2Cl_2$. After 1 h 30, the reaction mixture is diluted with water and the two phases are separated. The aqueous phase is re-extracted with $CH_2Cl_2$ and the combined organic extracts are successively washed with a sat.solution of $NaHCO_3$, water, sat. brine, dried over $Na_2SO_4$, filtered and the filtrate is concentrated in vacuo to afford, after drying in HV, the title compound which is used in the next step without further purification.

Preparation 13

(4-Methyl-piperazin-1-yl)-[2-methyl-4-(4,4,5,5-tetramethyl-[1,3,2]dioxaborolan-2-yl)-phenyl]-methanone

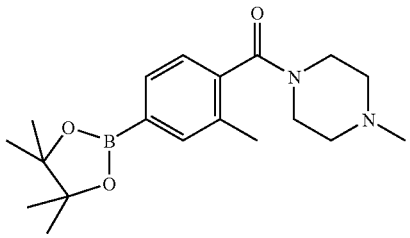

The title compound is obtained analogously to Preparation 1, but using (4-Bromo-2-methyl-phenyl)-(4-methyl-piperazin-1-yl)-methanone (as obtained in preparation 12).

Preparation 14

4-Bromo-2-methoxy-1-(2-methoxy-ethoxy)-benzene

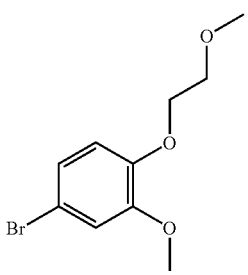

2.0 g (9.65 mmol) 4-bromoguaiacol and 1.89 g (5.8 mmol) Cs$_2$CO$_3$ are suspended in 20.0 ml dry DMF and 1.02 ml (10.6 mmol) 2-bromoethylmethylether are introduced at RT under an argon flux. The resulting pale brown suspension is heated to 100° C. for 15 h. After cooling, the reaction mixture is partitioned between EtOAc and water. The aqueous phase is re-extracted twice with EtOAc. The combined organic solution is washed with brine, dried over Na$_2$SO$_4$ and concentrated in vacuo to afford the title compound as a light yellow residue.

Preparation 15

2-[3-Methoxy-4-(2-methoxy-ethoxy)-phenyl]-4,4,5,5-tetramethyl-[1,3,2]dioxaborolane

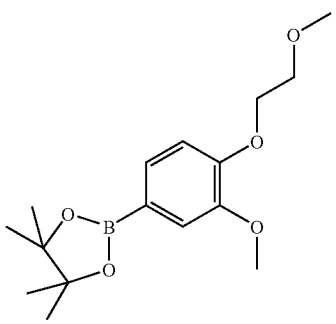

The title compound is obtained analogously to Preparation 1, but using 4-Bromo-2-methoxy-1-(2-methoxy-ethoxy)-benzene (as obtained in preparation 14).

Preparation 16

4-(4-Bromo-2-fluoro-benzyl)-thiomorpholine 1,1-dioxide

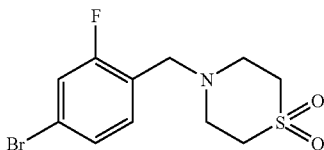

The title compound is obtained analogously to Preparation 9, but using 4-Bromo-2-fluorobenzyl bromide.

Preparation 17

4-[2-Fluoro-4-(4,4,5,5-tetramethyl-[1,3,2]dioxaborolan-2-yl)-benzyl]-thiomorpholine 1,1-dioxide

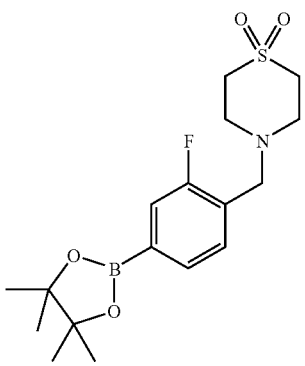

The title compound is obtained analogously to Preparation 1, but using 4-(4-Bromo-2-fluoro-benzyl)-thiomorpholine 1,1-dioxide (as obtained in preparation 16).

Preparation 18

2-(4-Bromo-2-fluoro-phenyl)-1-morpholin-4-yl-ethanone

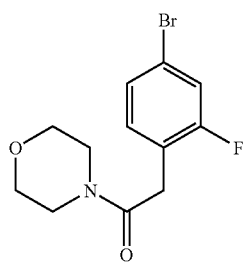

The title compound is obtained analogously to Preparation 12, but using 4-Bromo-2-fluorophenylacetic acid (CAS 114897-92-6) and morpholine.

Preparation 19

2-[2-Fluoro-4-(4,4,5,5-tetramethyl-[1,3,2]dioxaborolan-2-yl)-phenyl]-1-morpholin-4-yl-ethanone

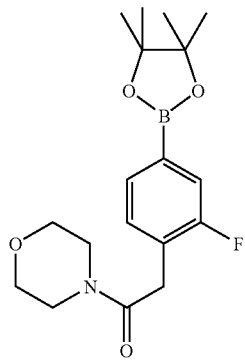

The title compound is obtained analogously to Preparation 1, but using 2-(4-Bromo-2-fluoro-phenyl)-1-morpholin-4-yl-ethanone (as obtained in preparation 18).

Preparation 20

4-Bromo-2,N,N-trimethyl-benzamide

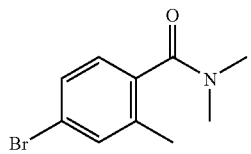

The title compound is obtained analogously to Preparation 12, but using N,N-dimethylamine.

Preparation 21

2,N,N-Trimethyl-4-(4,4,5,5-tetramethyl-[1,3,2]dioxaborolan-2-yl)-benzamide

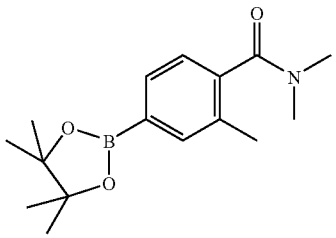

The title compound is obtained analogously to Preparation 1, but using 4-Bromo-2,N,N-trimethyl-benzamide (as obtained in preparation 20).

Preparation 22

4-Bromo-1-bromomethyl-2-trifluoromethyl-benzene

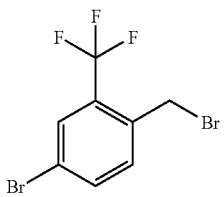

4-Bromo-1-methyl-2-trifluoromethyl-benzene (3 g, 12.55 mmol), N-bromosuccinimide (2.68 g, 15.06 mmol, 1.2 eq) and dibenzoylperoxid (60 mg, 2.5 mmol, 0.02 eq) are stirred in carbon tetrachloride under ultraviolet light at reflux for 5 h. The reaction mixture is cooled to RT, filtered and the filtrate is concentrated in vacuo. The residue is carefully purified by chromatography (silicagel, pure hexanes) to afford the title compound as a colorless liquid.

Preparation 23

4-(4-Bromo-2-trifluoromethyl-benzyl)-morpholine

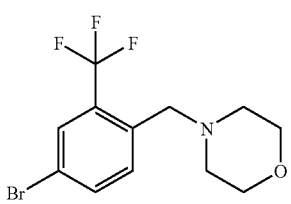

The title compound is obtained analogously to Preparation 9, but using 4-Bromo-1-bromomethyl-2-trifluoromethyl-benzene (as obtained in preparation 22) and morpholine.

Preparation 24

4-[4-(4,4,5,5-Tetramethyl-[1,3,2]dioxaborolan-2-yl)-2-trifluoromethyl-benzyl]-morpholine

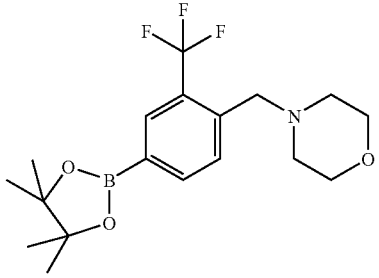

The title compound is obtained analogously to Preparation 1, but using 4-(4-Bromo-2-trifluoromethyl-benzyl)-morpholine (as obtained in preparation 23).

Preparation 25

(4-Bromo-2-methyl-phenyl)-methanol

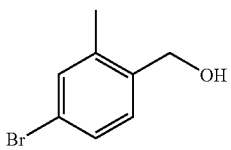

4-bromo-2-methylbenzoic acid (5 g, 22.8 mmol) is dissolved in dry THF (100 ml) and cooled to 0° C. A 1M solution of $BH_3$·THF in THF (34 mL, 34 mmol) is slowly added. The resulting colorless suspension is then stirred overnight, allowing it to gradually reach room temperature. $K_2CO_3$ solid (1.1 g) and $H_2O$ (100 ml) are added to the colorless solution and the mixture is stirred for an additional 30 minutes. THF is then evaporated and the residue extracted with EtOAc (30 ml). The organic phase is washed with 1N HCl (3×50 ml), dried over $Na_2SO_4$ and evaporated. The residue gives the title compound which is used in the next step without further purification.

Preparation 26

4-Bromo-1-bromomethyl-2-methyl-benzene

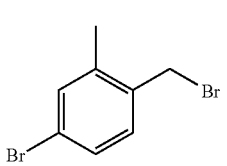

To a stirred solution of (4-Bromo-2-methyl-phenyl)-methanol (as obtained in preparation 25) (4.58 g, 22.8 mmol) in CH$_2$Cl$_2$ (50 ml) is added, under Argon and at RT, carbon tetrabromide (9.27 g, 27.4 mmol) followed by triphenylphosphine (7.25 g, 27.4 mmol). The mixture is stirred overnight and then concentrated in vacuo. The crude residue is then purified by chromatography (silicagel, hexane:EtOAc 25:1) to afford the title compound as a clear oil.

Preparation 27

4-(4-Bromo-2-methyl-benzyl)-thiomorpholine 1,1-dioxide

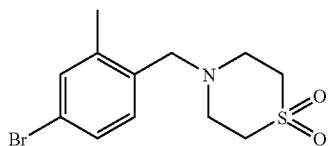

The title compound is obtained analogously to Preparation 9, but using 4-Bromo-1-bromomethyl-2-methyl-benzene (as obtained in preparation 26).

Preparation 28

4-[2-Methyl-4-(4,4,5,5-tetramethyl-[1,3,2]dioxaborolan-2-yl)-benzyl]-thiomorpholine 1,1-dioxide

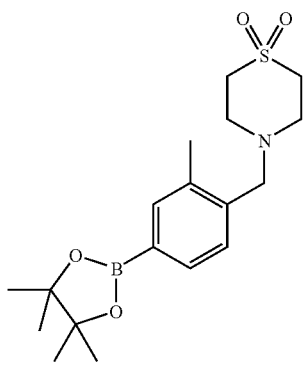

The title compound is obtained analogously to Preparation 1, but using 4-(4-Bromo-2-methyl-benzyl)-thiomorpholine 1,1-dioxide (as obtained in preparation 27).

Preparation 29

4-(4-Bromo-2,6-difluoro-benzyl)-morpholine

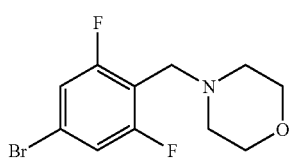

The title compound is obtained analogously to Preparation 9, but using 5-Bromo-2-bromomethyl-1,3-difluoro-benzene (CAS 162744-60-7) and morpholine.

Preparation 30

4-[2,6-Difluoro-4-(4,4,5,5-tetramethyl-[1,3,2]dioxaborolan-2-yl)-benzyl]-morpholine

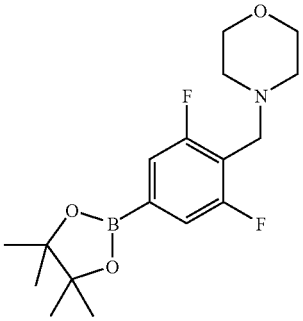

The title compound is obtained analogously to Preparation 1, but using 4-(4-Bromo-2,6-difluoro-benzyl)-morpholine (as obtained in preparation 29).

Preparation 31

4-(4-Bromo-2-methyl-benzyl)-morpholine

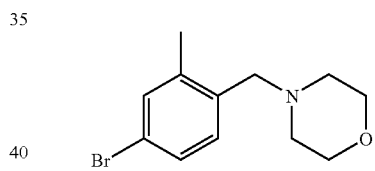

The title compound is obtained analogously to Preparation 9, but using 4-Bromo-1-bromomethyl-2-methyl-benzene (as obtained in preparation 26) and morpholine.

Preparation 32

4-[2-Methyl-4-(4,4,5,5-tetramethyl-[1,3,2]dioxaborolan-2-yl)-benzyl]-morpholine

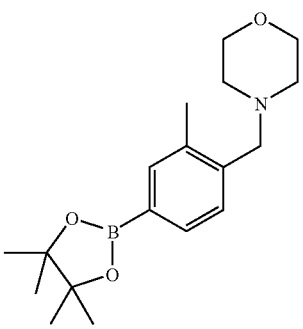

The title compound is obtained analogously to Preparation 1, but using 4-(4-Bromo-2-methyl-benzyl)-morpholine (as obtained in preparation 31).

Preparation 33

(4-Bromo-2-chloro-phenyl)-methanol

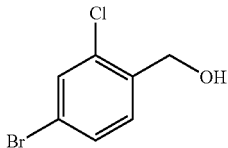

The title compound is obtained analogously to Preparation 25, but using 4-bromo-2-chlorobenzoic acid.

Preparation 34

4-Bromo-1-bromomethyl-2-chloro-benzene

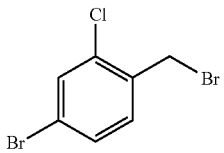

The title compound is obtained analogously to Preparation 26, but using (4-Bromo-2-chloro-phenyl)-methanol Preparation 35

4-(4-Bromo-2-chloro-benzyl)-thiomorpholine 1,1-dioxide

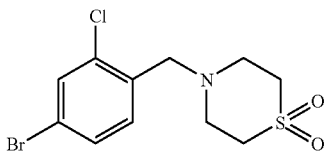

The title compound is obtained analogously to Preparation 9, but using 4-Bromo-1-bromomethyl-2-chloro-benzene (as obtained in preparation 34).

Preparation 36

4-[2-Chloro-4-(4,4,5,5-tetramethyl-[1,3,2]dioxaborolan-2-yl)-benzyl]-thiomorpholine 1,1-dioxide

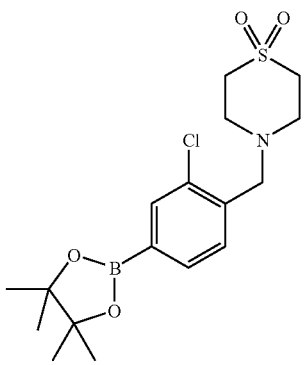

The title compound is obtained analogously to Preparation 1, but using 4-(4-Bromo-2-chloro-benzyl)-thiomorpholine 1,1-dioxide (as obtained in preparation 35).

Preparation 37

(4-Bromo-2-methyl-phenyl)-pyrrolidin-1-yl-methanone

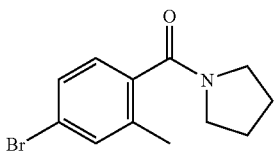

The title compound is obtained analogously to Preparation 12, but using pyrrolidine.

Preparation 38

[2-Methyl-4-(4,4,5,5-tetramethyl-[1,3,2]dioxaborolan-2-yl)-phenyl]-pyrrolidin-1-yl-methanone

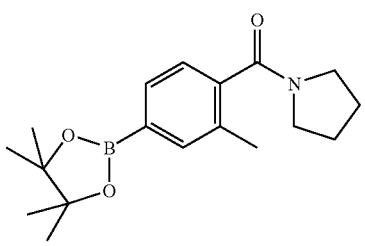

The title compound is obtained analogously to Preparation 1, but using (4-Bromo-2-methyl-phenyl)-pyrrolidin-1-yl-methanone (as obtained in preparation 37).

Preparation 39

2-(4-Bromo-2-fluoro-phenyl)-1-(1,1-dioxido-thiomorpholin-4-yl)-ethanone

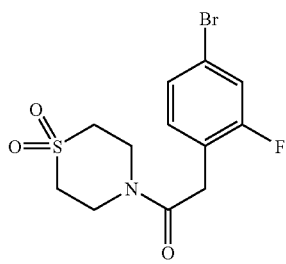

The title compound is obtained analogously to Preparation 12, but using 4-Bromo-2-fluorophenylacetic acid (CAS 114897-92-6) and thiomorpholine 1,1-dioxide.

Preparation 40

1-(1,1-Dioxido-thiomorpholin-4-yl)-2-[2-fluoro-4-(4,4,5,5-tetramethyl-1,3,2]dioxaborolan-2-yl)-phenyl]-ethanone

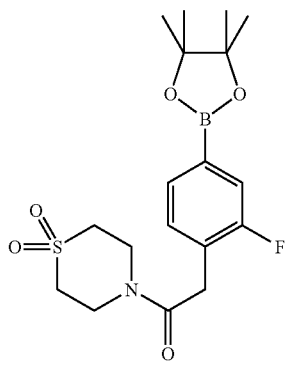

The title compound is obtained analogously to Preparation 1, but using 2-(4-Bromo-2-fluoro-phenyl)-1-(1,1-dioxido-thiomorpholin-4-yl)-ethanone (as obtained in preparation 39).

Preparation 41

1-(4-Bromo-2-methyl-benzyl)-1H-imidazole

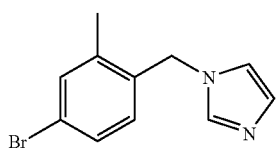

The title compound is obtained analogously to Preparation 9, but using 4-Bromo-1-bromomethyl-2-methyl-benzene (as obtained in preparation 26) and imidazole.

Preparation 42

1-[2-Methyl-4-(4,4,5,5-tetramethyl-[1,3,2]dioxaborolan-2-yl)-benzyl]-1H-imidazole

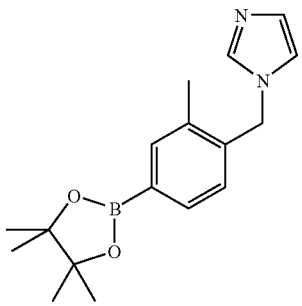

The title compound is obtained analogously to Preparation 1, but using 1-(4-Bromo-2-methyl-benzyl)-1H-imidazole (as obtained in preparation 41).

Preparation 43

(4-Bromo-2-fluoro-phenyl)-(1,1-dioxido-thiomorpholin-4-yl)-methanone

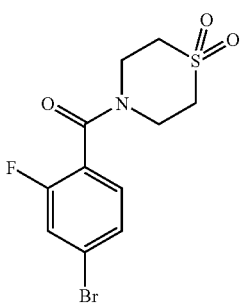

The title compound is obtained analogously to Preparation 7, but using thiomorpholine 1,1-dioxide Preparation 44

(1,1-Dioxido-thiomorpholin-4-yl)-[2-fluoro-4-(4,4,5,5-tetramethyl-[1,3,2]dioxaborolan-2-yl)-phenyl]-methanone

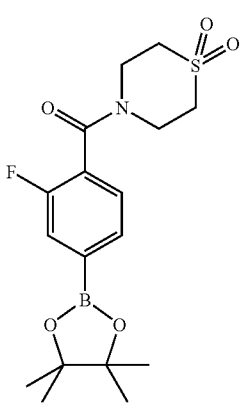

The title compound is obtained analogously to Preparation 1, but using (4-Bromo-2-fluoro-phenyl)-(1,1-dioxido-thiomorpholin-4-yl)-methanone (as obtained in preparation 43)

Preparation 45

(4-Bromo-2-chloro-phenyl)-morpholin-4-yl-methanone

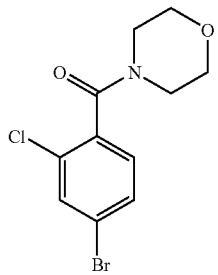

The title compound is obtained analogously to Preparation 7, but using 4-Bromo-2-chloro-benzoic acid (CAS 59748-90-2)

Preparation 46

[2-Chloro-4-(4,4,5,5-tetramethyl-[1,3,2]dioxaborolan-2-yl)-phenyl]-morpholin-4-yl-methanone

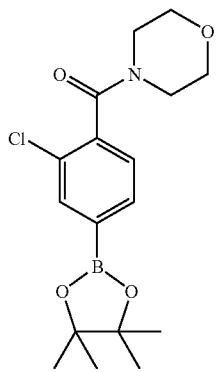

The title compound is obtained analogously to Preparation 1, but using (4-Bromo-2-chloro-phenyl)-morpholin-4-yl-methanone (as obtained in preparation 45)

Preparation 47

4-{3-[2-Methyl-4-(4,4,5,5-tetramethyl-≡1,3,2]dioxaborolan-2-yl)-phenoxy]-propyl}-morpholine

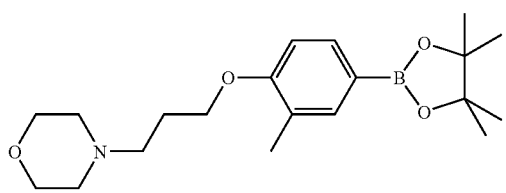

The title compound is obtained analogously to Preparation 1, but using 4-[3-(4-Bromo-2-methyl-phenoxy)-propyl]-morpholine (CAS 434303-70-5)

Preparation 48

1-(4-Bromo-2-methyl-phenyl)-1-methyl-ethylamine

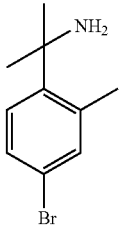

In a dried apparatus, Cerium (III) trichloride ultradry (5 g, 20.28 mmol) is introduced under Ar and anhydrous THF is added (40 ml). The resultant suspension gives a milky solution after 24 h stirring at RT. The mixture is then cooled to −65° C. and a solution of MeLi (1.6 M in Et$_2$O, 12.67 mL, 20.28 mmol) is added dropwise and the canary yellow suspension is stirred for 30 min. A solution of 4-bromo-2-methylbenzonitrile (1.365 g, 6.76 mmol) in THF (5 ml) is added and the reaction is further stirred at −65° C. for 4 h before allowing to warm to −40° C. The brown suspension is quenched by addition of 20 ml of 25% ammoniaque solution and then allow to warm to RT. The resulting solids are removed by filtration on a pad of Celite and washed three times with EtOAc. The combined filtrates are washed with brine, dried over Na$_2$SO$_4$ and concentrated in vacuo to give the desired compound as a colorless liquid. R$_t$=0.735 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 211 (M-NH$_3$+1, $^{79}$Br)$^+$.

Preparation 49

4-[1-(4-Bromo-2-methyl-phenyl)-1-methyl-ethyl]-morpholine

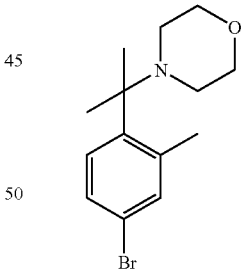

A solution of 1-(4-Bromo-2-methyl-phenyl)-1-methyl-ethylamine (preparation 48, 544 mg, 2 mmol), 2,2'-dibromodiethylether (579.8 mg, 2.5 mmol) and N,N-diisopropylethylamine (1.027 ml, 6 mmol) in DMF (7 ml) is heated to 100° C. for 16 h and then allowed to cool to RT. The reaction mixture is partitioned between water and CH$_2$Cl$_2$. The aqueous phase is re-extracted twice, the combined organic phases are dried over Na$_2$SO$_4$ and concentrated in vacuo. The residue is purified by flash chromatography (silicagel, CH$_2$Cl$_2$:EtOAc=1:0=>0:1) to afford the title compound as a pale yellow oil, R$_t$=0.786 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 298 (M+1, $^{79}$Br)$^+$.

Preparation 50

4-{1-Methyl-1-[2-methyl-4-(4,4,5,5-tetramethyl-[1,3,2]dioxaborolan-2-yl)-phenyl]-ethyl}-morpholine

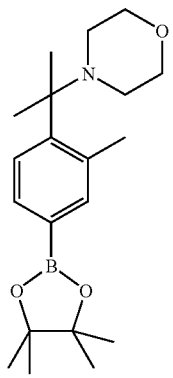

The title compound is obtained analogously to Preparation 1, but using 4-[1-(4-Bromo-2-methyl-phenyl)-1-methyl-ethyl]-morpholine (preparation 49)

Preparation 51

4-[1-(4-Bromo-2-methyl-phenyl)-1-methyl-ethyl]-thiomorpholine 1,1-dioxide

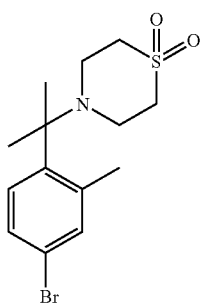

A solution of 1-(4-Bromo-2-methyl-phenyl)-1-methyl-ethylamine (preparation 48, 544 mg, 2 mmol), vinyl sulfone (200 μl, 2 mmol) in EtOH (8 ml) is heated to 100° C. for 6 h and then allowed to cool to RT. EtOH is removed under HV and the residue is purified by flash chromatography (silicagel, $CH_2Cl_2$:EtOAc=1:0=>0:1) to afford the title compound as a pale pink solid, $R_t$=1.231 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+0.1% TFA, flow rate 1.0 ml/min); MS: 346 (M+1, $^{79}Br)^+$.

Preparation 52

4-{1-Methyl-1-[2-methyl-4-(4,4,5,5-tetramethyl-[1,3,2]dioxaborolan-2-yl)-phenyl]-ethyl}-thiomorpholine 1,1-dioxide

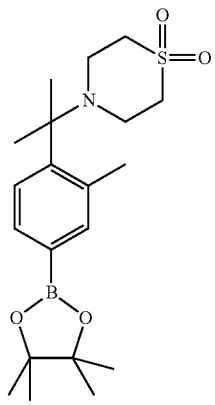

The title compound is obtained analogously to Preparation 1, but using 4-[1-(4-Bromo-2-methyl-phenyl)-1-methyl-ethyl]-thiomorpholine 1,1-dioxide (preparation 51)

Preparation 53

4-Bromo-2-methyl-phenyl)-(4-ethyl-piperazin-1-yl)-methanone

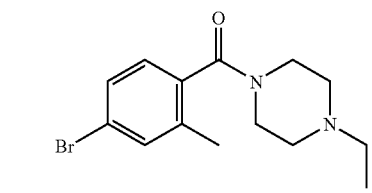

The title compound is obtained analogously to Preparation 12, but using N-ethylpiperazine

Preparation 54

(4-Ethyl-piperazin-1-yl)-[2-methyl-4-(4,4,5,5-tetramethyl-[1,3,2]dioxaborolan-2-yl)-phenyl]-methanone

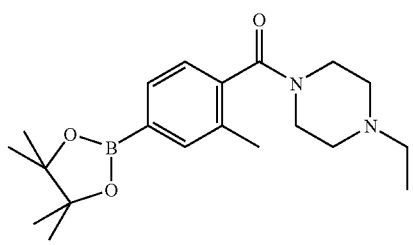

The title compound is obtained analogously to Preparation 1, but using 4-Bromo-2-methyl-phenyl)-(4-ethyl-piperazin-1-yl)-methanone (as obtained in preparation 53).

Preparation 55

4-{3-[2-Methoxy-4-(4,4,5,5-tetramethyl-[1,3,2]dioxaborolan-2-yl)-phenoxy]-propyl}-morpholine

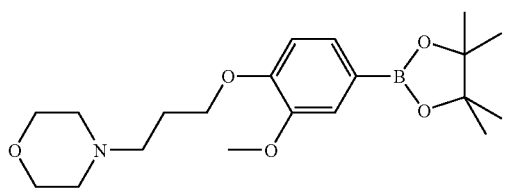

A solution of 4-(3-Chloro-propyl)-morpholine (460 mg, 2.75 mmol), Cs$_2$CO$_3$ (493 mg, 1.515 mmol) and 2-Methoxy-4-(4,4,5,5-tetramethyl-[1,3,2]dioxaborolan-2-yl)-phenol (703 mg, 2.75 mmol) in dry DMF (15 ml) are heated at 80° C. under argon for 24 h and then allowed to cool to RT. DMF is removed under HV and the residue is re-taken in EtOAc and washed with de-ionized water. The aqueous phase is re-extracted with EtOAc and the combined organic extracts are washed with saturated brine, dried over Na$_2$SO$_4$, filtered and concentrated under vacuum to dryness. After drying under HV, the title compound is obtained as a solid, R$_f$=0.878 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 378 (M+1)$^+$.

Preparation 56

1-Methyl-4-[4-(4,4,5,5-tetramethyl-[1,3,2]dioxaborolan-2-yl)-phenyl]-piperazine

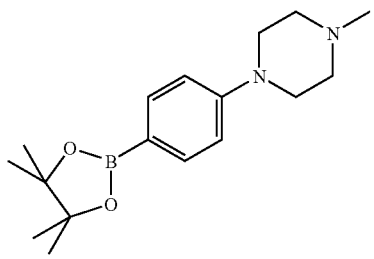

To a cooled (−78° C.) solution of 1-(4-Bromo-phenyl)-4-methyl-piperazine (8.05 g, 31.54 mmol, CAS 130307-08-3) in dry THF (500 ml) are added dropwise 28 ml of a solution of n-BuLi (2.5M in hexanes, 69 mmol). After 1 h, of 2-isopropoxy-4,4,5,5-tetramethyl-1,3,2-dioxaborolane (13.1 ml, 63.1 mmol) in solution in dry THF (20 ml) are introduced. After complete addition, the reaction mixture is allowed to slowly warm up to RT. The reaction mixture is then diluted with 200 ml of a saturated solution of NH$_4$Cl and most of the THF is removed by evaporation. The residue is diluted with EtOAc and the phases are separated. The aqueous phase is re-extracted three times with EtOAc and the combined organic extracts are washed twice with de-ionized water, once with saturated brine, dried over Na$_2$SO$_4$, filtered and concentrated in vacuo. The residue is purified by chromatography (silicagel, CH$_2$Cl$_2$/EtOH 9:1) to afford the title compound as a colorless solid, R$_f$=0.851 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 303 (M+1)$^+$.

Preparation 57

1-(4-Bromo-2-methyl-benzyl)-4-ethyl-piperazine

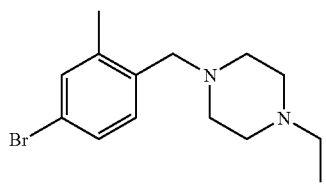

The title compound is obtained analogously to Preparation 9, but using 4-Bromo-1-bromomethyl-2-methyl-benzene (as obtained in preparation 26) and N-ethylpiperazine.

Preparation 58

1-Ethyl-4-[2-methyl-4-(4,4,5,5-tetramethyl-[1,3,2]dioxaborolan-2-yl)-benzyl]-piperazine

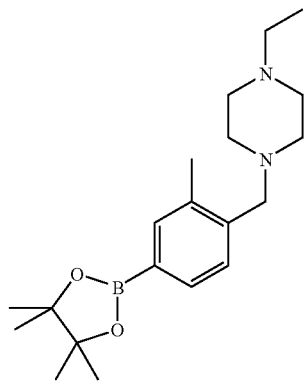

The title compound is obtained analogously to Preparation 1, but using 1-(4-Bromo-2-methyl-benzyl)-4-ethyl-piperazine (as obtained in preparation 57).

Preparation 59

4-Bromo-N-(2-dimethylamino-ethyl)-2,N-dimethyl-benzamide

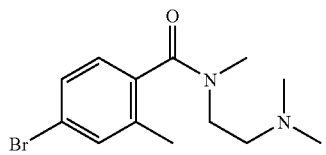

The title compound is obtained analogously to Preparation 12, but using N,N,N'-Trimethyl-ethane-1,2-diamine Preparation 60

N-(2-Dimethylamino-ethyl)-2,N-dimethyl-4-(4,4,5,5-tetramethyl-[1,3,2]dioxaborolan-2-yl)-benzamide

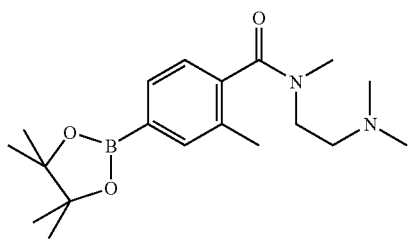

The title compound is obtained analogously to Preparation 1, but using 4-Bromo-N-(2-dimethylamino-ethyl)-2,N-dimethyl-benzamide (as obtained in preparation 59).

Preparation 61

4-Methanesulfonyloxy-piperidine-1-carboxylic acid tert-butyl ester

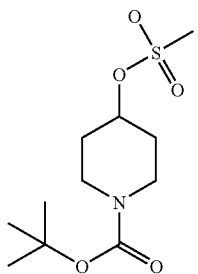

To a stirred solution of 4-hydroxy-piperidine-1-carboxylic acid tert-butyl ester (25.55 g, 123 mmol) in $CH_2Cl_2$ (250 ml), cooled to 0° C., is slowly added $Et_3N$ (18.95 ml, 135.4 mmol) followed by methane sulfonyl chloride (9.569 ml, 123.14 mmol) and DMAP (152 mg, 1.23 mmol). The mixture is stirred at room temperature overnight. The suspension is diluted with $CH_2Cl_2$ and the phases are separated. The aqueous phase is re-extracted 3× with $CH_2Cl_2$. The combined organic layers are washed with brine, dried over $Na_2SO_4$, filtered and the filtrate is concentrated in vacuo. Upon concentration, the desired compound precipitates and is collected by filtration to afford, after drying in HV, the title compound as a colorless solid.

Preparation 62

4-(4-Bromo-pyrazol-1-yl)-piperidine-1-carboxylic acid tert-butyl ester

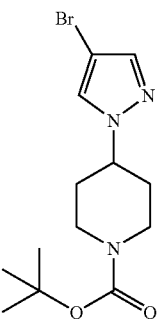

NaH (60% in mineral oil, 1.36 g, 34 mmol) is added portionwise to a stirred solution of 4-bromopyrazole (4.58 g, 30.9 mmol) in DMF (20 ml). The resulting mixture is stirred for 1 h at 0° C. and 4-Methanesulfonyloxy-piperidine-1-carboxylic acid tert-butyl ester (as obtained in preparation 61, 8.62 g, 30.9 mmol) is added. The resulting pale suspension is heated at 100° C. for 1 h. The reaction is quenched with water and extracted with EtOAc several times. The combined organic layers are washed with brine, dried over $Na_2SO_4$, filtered and the filtrate is concentrated in vacuo. The residue is purified by chromatography on a 120 g silica gel column on a Combiflash Companion™ (Isco Inc.) apparatus (gradient hexanes: TBDME from 1:0=>0:1) to afford the title compound as a colorless solid, $R_t$=1.213 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+0.1% TFA, flow rate 1.0 ml/min); MS: 330 (M+1, $^{79}Br$)$^+$.

Preparation 63

4-[4-(4,4,5,5-Tetramethyl-[1,3,2]dioxaborolan-2-yl)-pyrazol-1-yl]-piperidine-1-carboxylic acid tert-butyl ester

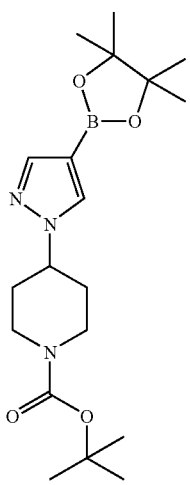

The title compound is obtained analogously to Preparation 1, but using 4-(4-Bromo-pyrazol-1-yl)-piperidine-1-carboxylic acid tert-butyl ester (as obtained in preparation 62).

Preparation 64

4-Bromo-2-fluoro-1-methylsulfanyl-benzene

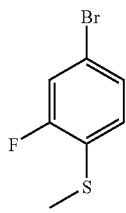

To a stirred solution of 2-fluorothioanisole (5.12 g, 35.3 mmol) in $CH_2Cl_2$ (30 ml) is added dropwise a solution of dibrome (1.8 ml, 35.51 mmol) in $CH_2Cl_2$ (10 ml). After complete addition, the red solution is then poured onto a saturated solution of $NaHCO_3$ and extracted with $CH_2Cl_2$ several times. The combined organic layers are washed with brine, dried over $Na_2SO_4$, filtered and the filtrate is concentrated in vacuo. The residue is purified by chromatography (silicagel, n-hexanes/$CH_2Cl_2$ 9:1) to afford the title compound, $R_t$=1.324 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+ 0.1% TFA, flow rate 1.0 ml/min).

Preparation 65

4-Bromo-2-fluoro-1-methanesulfonyl-benzene

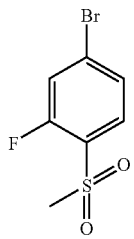

In a 50 ml sealable tube is introduced 4-Bromo-2-fluoro-1-methylsulfanyl-benzene (as obtained in preparation 63, 5 g, 22.6 mmol) followed by 4.6 ml AcOH. 9.3 ml of a 30% $H_2O_2$ solution in $H_2O$ is added at RT. The tube is sealed and the resulting colorless biphasic solution is stirred at 100° C. for 2 h. After cooling, the pH of the medium is set basic with solid $NaHCO_3$ and then extracted with $CH_2Cl_2$ several times. The combined organic layers are washed with brine, dried over $Na_2SO_4$, filtered and the filtrate is concentrated in vacuo. The title compound is obtained as a colorless solid, $R_t$=0.916 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+0.1% TFA, flow rate 1.0 ml/min)

Preparation 66

2-(3-Fluoro-4-methanesulfonyl-phenyl)-4,4,5,5-tetramethyl-[1,3,2]dioxaborolane

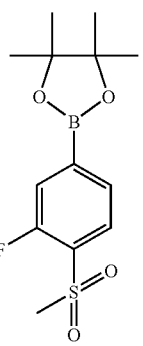

The title compound is obtained analogously to Preparation 56, but using 4-Bromo-2-fluoro-1-methanesulfonyl-benzene (as obtained in preparation 65).

Preparation 67

(4-Bromo-2-methyl-phenyl)-(4-dimethylamino-piperidin-1-yl)-methanone

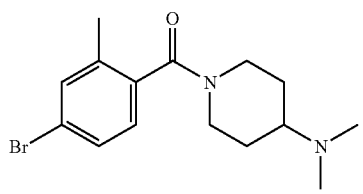

The title compound is obtained analogously to Preparation 12, but using dimethyl-piperidin-4-yl-amine Preparation 68

(4-Dimethylamino-piperidin-1-yl)-[2-methyl-4-(4,4,5,5-tetramethyl-[1,3,2]dioxaborolan-2-yl)-phenyl]-methanone

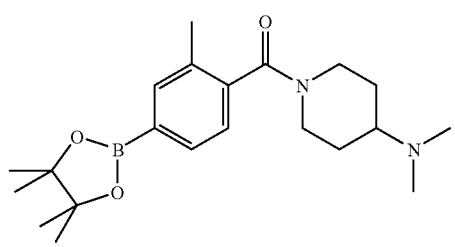

The title compound is obtained analogously to Preparation 1, but using (4-Bromo-2-methyl-phenyl)-(4-dimethylamino-piperidin-1-yl)-methanone (as obtained in preparation 67).

Preparation 69

1-(4-Bromo-2-methyl-phenyl)-4-ethyl-piperazine

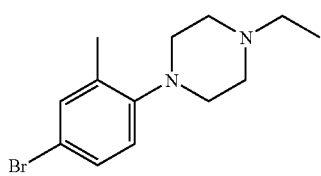

4-(4-Ethyl-piperazin-1-yl)-3-methyl-phenylamine (1.3 g, 6 mmol) in hydrobromic acid (61% in H$_2$O, 9.2 ml, 70 mmol) is diazotized at 0° C. with sodium nitrite (443 mg, 6.42 mmol) in 2.3 ml H$_2$O and the mixture is poured into a solution of copper(I) bromide (1.84 g, 12.5 mmol) in hydrobromic acid (61% in H$_2$O, 7.7 ml, 58.8 mmol) at 0° C. The cooling bath is then removed and the mixture is heated at 60° C. for 5 h. After cooling, the mixture is basified with a 2M NaOH solution and diluted with CH$_2$Cl$_2$. After separation, the aqueous phase is extracted with CH$_2$Cl$_2$ several times. The combined organic layers are washed with brine, dried over Na$_2$SO$_4$, filtered and the filtrate is concentrated in vacuo. The residue is purified by chromatography on a 120 g silica gel column on a Combiflash Companion™ (Isco Inc.) apparatus (gradient CH$_2$Cl$_2$/CH$_2$Cl$_2$:EtOH:NH3 90:9:1 from 1:0=>4:6) to afford the title compound as a pale brown solid, R$_t$=0.878 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 283 (M+1, $^{79}$Br)$^+$.

Preparation 70

1-Ethyl-4-[2-methyl-4-(4,4,5,5-tetramethyl-[1,3,2]dioxaborolan-2-yl)-phenyl]-piperazine

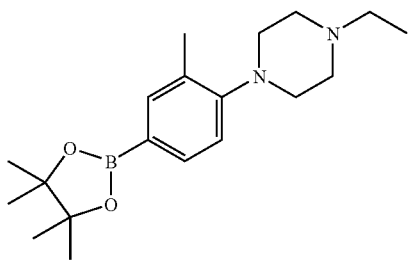

The title compound is obtained analogously to Preparation 1, but using 1-(4-Bromo-2-methyl-phenyl)-4-ethyl-piperazine (as obtained in preparation 69).

Preparation 71

1-(2-Methoxy-phenyl)-4-methyl-piperazine

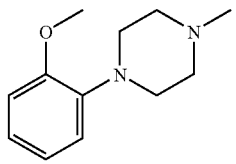

Formaldehyde (1.84 ml in solution) is added to a solution of 1-(2-methoxyphenyl)-piperazine (4.77 g, 24.3 mmol) in 1,2-dichloroethane. NaHB(OAc)$_3$ (7.59 g, 34 mmol) is then added portionwise. After stirring at RT overnight, the reaction is quenched by addition of a saturated solution of NaHCO$_3$. The mixture is extracted several times with EtOAc and the combined organic layers are washed with brine, dried over Na$_2$SO$_4$, filtered and the filtrate is concentrated in vacuo to afford the title compound as a colorless oil, R$_t$=0.615 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 207 (M+1)$^+$.

Preparation 72

1-(4-Bromo-2-methoxy-phenyl)-4-methyl-piperazine

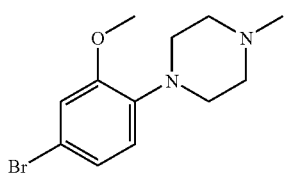

A bromine solution (1.24 ml, 24.2 mmol) in 9.7 ml AcOH is added dropwise to a cooled solution (ca. 5° C.) of 1-(2-Methoxy-phenyl)-4-methyl-piperazine (as obtained in preparation 71, 5 g, 24.2 mmol) in AcOH (87 ml). After complete addition, the cooling bath is removed and reaction mixture allowed to warm up to RT. The dark violet solution is concentrated in vacuo, 20 ml de-ionized water is added and the pH is adjusted basic with a 20% NaOH solution. The mixture is extracted several times with CH$_2$Cl$_2$ and the combined organic layers are washed with brine, dried over Na$_2$SO$_4$, filtered and the filtrate is concentrated in vacuo. The residue is purified by chromatography on a 120 g silica gel column on a Combiflash Companion™ (Isco Inc.) apparatus (gradient CH$_2$Cl$_2$/CH$_2$Cl$_2$:EtOH:NH$_3$ 90:9:1 from 1:0=>0:1) to afford the title compound as a dark brown oil, R$_t$=0.767 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 285 (M+1, $^{79}$Br)$^+$.

Preparation 73

1-[2-Methoxy-4-(4,4,5,5-tetramethyl-[1,3,2]dioxaborolan-2-yl)-phenyl]-4-methyl-piperazine

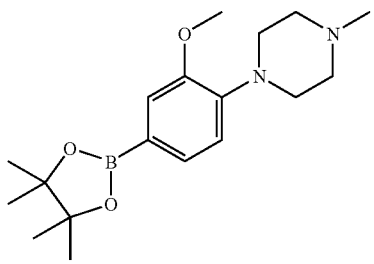

The title compound is obtained analogously to Preparation 1, but using 1-(4-Bromo-2-methoxy-phenyl)-4-methyl-piperazine (as obtained in preparation 72).

Preparation 74

5-Bromo-pyridine-2-carboxylic acid (2-dimethylamino-ethyl)-methyl-amide

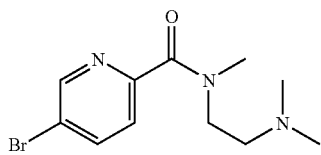

The title compound is obtained analogously to Preparation 12, but using N,N,N'-Trimethyl-ethane-1,2-diamine and 5-Bromo-pyridine-2-carboxylic acid

Preparation 75

5-(4,4,5,5-Tetramethyl-[1,3,2]dioxaborolan-2-yl)-pyridine-2-carboxylic acid (2-dimethylamino-ethyl)-methyl-amide

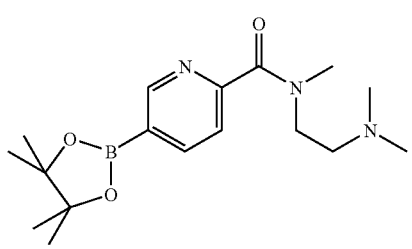

The title compound is obtained analogously to Preparation 1, but using 5-Bromo-pyridine-2-carboxylic acid (2-dimethylamino-ethyl)-methyl-amide (as obtained in preparation 74).

Preparation 76

5-Bromo-3-methyl-pyridine-2-carboxylic acid (2-dimethylamino-ethyl)-methyl-amide

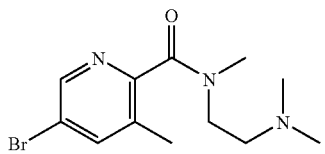

The title compound is obtained analogously to Preparation 12, but using N,N,N'-Trimethyl-ethane-1,2-diamine and 5-Bromo-3-methyl-pyridine-2-carboxylic acid

Preparation 77

3-Methyl-5-(4,4,5,5-tetramethyl-[1,3,2]dioxaborolan-2-yl)-pyridine-2-carboxylic acid (2-dimethylamino-ethyl)-methyl-amide

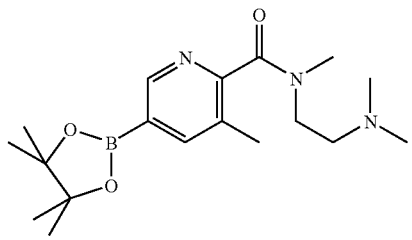

The title compound is obtained analogously to Preparation 1, but using 5-Bromo-3-methyl-pyridine-2-carboxylic acid (2-dimethylamino-ethyl)-methyl-amide (as obtained in preparation 76).

Preparation 78

4-{3-[4-(4,4,5,5-Tetramethyl-[1,3,2]dioxaborolan-2-yl)-pyrazol-1-yl]-propyl}-morpholine

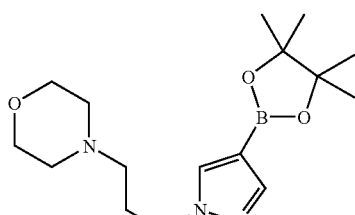

A solution of 4-(3-Chloro-propyl)-morpholine (702 mg, 4.2 mmol), $Cs_2CO_3$ (753 mg, 2.31 mmol) and 4-(4,4,5,5-Tetramethyl-[1,3,2]dioxaborolan-2-yl)-1H-pyrazole (832 mg, 4.2 mmol) in 5 ml dry DMF are heated at 80° C. under argon for 24 h and then allowed to cool to RT. DMF is removed under HV and the residue is re-taken in EtOAc and washed with de-ionized water. The aqueous phase is re-extracted with EtOAc and the combined organic extracts are washed with saturated brine, dried over $Na_2SO_4$, filtered and concentrated under vacuum to dryness. After drying under HV, the title compound is obtained as a pale orange oil, $R_t$=0.728 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+ 0.1% TFA, flow rate 1.0 ml/min); MS: 322 (M+1)$^+$.

Preparation 79

1-(2-Methoxy-ethyl)-4-(4,4,5,5-tetramethyl-[1,3,2]dioxaborolan-2-yl)-1H-pyrazole

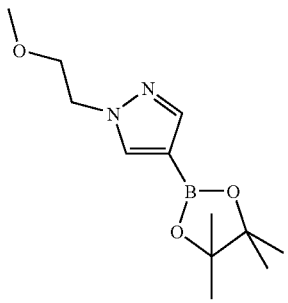

The title compound is obtained analogously to Preparation 78, but using 2-chloroethyl methyl ether.

Preparation 80

3-Methanesulfonyloxy-azetidine-1-carboxylic acid tert-butyl ester

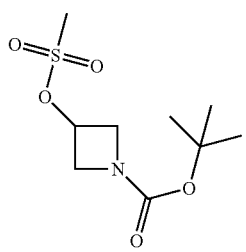

The title compound is obtained analogously to Preparation 61, but using 3-Hydroxy-azetidine-1-carboxylic acid tert-butyl ester.

Preparation 81

3-[4-(4,4,5,5-Tetramethyl-[1,3,2]dioxaborolan-2-yl)-pyrazol-1-yl]-azetidine-1-carboxylic acid tert-butyl ester

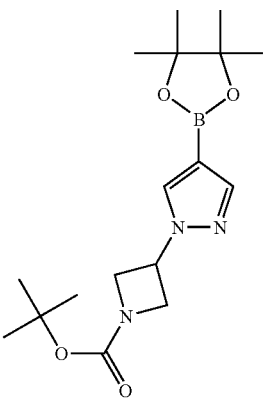

NaH (60% in mineral oil, 222 mg, 5.6 mmol) is added portionwise to a stirred solution of 4-(4,4,5,5-Tetramethyl-[1,3,2]dioxaborolan-2-yl)-1H-pyrazole (1.10 g, 5.56 mmol) in DMF (20 ml). The resulting mixture is stirred for 1 h at 0° C. and then allowed to warm to RT. A solution of 3-Methanesulfonyloxy-azetidine-1-carboxylic acid tert-butyl ester (as obtained in preparation 80, 1.39 g, 5.56 mmol) in DMF (3 ml) is then added dropwise. After complete addition, the reaction mixture is heated at 95° C. for 5 h. The reaction is quenched with water and extracted with EtOAc several times. The combined organic layers are washed with brine, dried over $Na_2SO_4$, filtered and the filtrate is concentrated in vacuo. The residue is purified by chromatography on a 40 g silica gel column on a Combiflash Companion™ (Isco Inc.) apparatus (gradient $CH_2Cl_2$: TBDME from 1:0=>0:1) to afford the title compound as a colorless foam, $R_t$=1.200 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+0.1% TFA, flow rate 1.0 ml/min); MS: 350 (M+1)$^+$.

Preparation 82

Methanesulfonic acid tetrahydro-pyran-4-yl ester

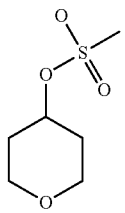

The title compound is obtained analogously to Preparation 61, but using Tetrahydro-pyran-4-ol.

Preparation 83

4-Bromo-1-(tetrahydro-pyran-4-yl)-1H-pyrazole

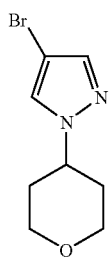

The title compound is obtained analogously to Preparation 62, but using Methanesulfonic acid tetrahydro-pyran-4-yl ester (as obtained in preparation 82).

Preparation 84

1-(Tetrahydro-pyran-4-yl)-4-(4,4,5,5-tetramethyl-[1,3,2]dioxaborolan-2-yl)-1H-pyrazole

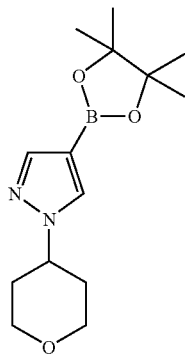

The title compound is obtained analogously to Preparation 1, but using 4-Bromo-1-(tetrahydro-pyran-4-yl)-1H-pyrazole (as obtained in preparation 83).

Preparation 85

4-(4-Bromo-2,6-difluoro-benzyl)-piperazin-2-one

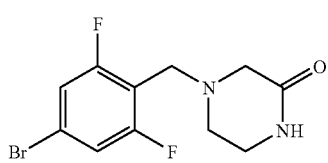

The title compound is obtained analogously to Preparation 9, but using 5-Bromo-2-bromomethyl-1,3-difluoro-benzene (CAS 162744-60-7) and piperazin-2-one.

Preparation 86

4-[2,6-Difluoro-4-(4,4,5,5-tetramethyl-[1,3,2]dioxaborolan-2-yl)-benzyl]-piperazin-2-one

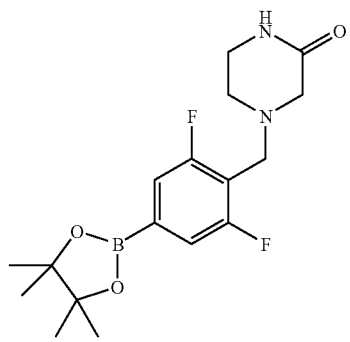

The title compound is obtained analogously to Preparation 1, but using 4-(4-Bromo-2,6-difluoro-benzyl)-piperazin-2-one (as obtained in preparation 85).

Preparation 87

4-Bromo-N-(2-hydroxy-ethyl)-2-methyl-benzamide

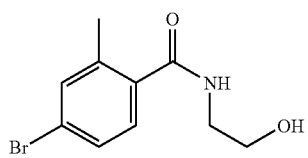

The title compound is obtained analogously to Preparation 12, but using 2-aminoethanol Preparation 88

N-(2-Hydroxy-ethyl)-2-methyl-4-(4,4,5,5-tetramethyl-[1,3,2]dioxaborolan-2-yl)-benzamide

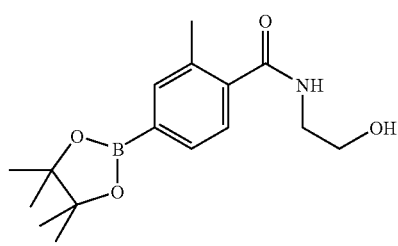

The title compound is obtained analogously to Preparation 1, but using 4-Bromo-N-(2-hydroxy-ethyl)-2-methyl-benzamide (as obtained in preparation 87).

Preparation 89

4-(4-Bromo-pyrazol-1-yl)-piperidine

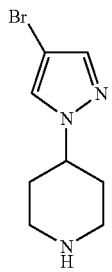

A 4 M solution of HCl in 1,4-dioxane (13.5 ml, 54 mmol) is added to a solution of 4-(4-Bromo-pyrazol-1-yl)-piperidine-1-carboxylic acid tert-butyl ester (as obtained in preparation 62, 5.92 g, 17.94 mmol) in CH$_2$Cl$_2$ (50 ml) and the reaction mixture is stirred at RT for 6 h. The suspension is filtered on a Por. 4 Fritte and the cake dissolved in EtOAc. A saturated solution of NaHCO$_3$ is added and the phases are separated. The aqueous phase is extracted 3× with EtOAc. The combined organic layers are washed with NaHCO$_3$, brine, dried over Na$_2$SO$_4$, filtered and the filtrate is concentrated in vacuo. The residue is used without further purification in the next step, and afford the title compound as pale orange solid, R$_t$=0.582 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 330 (M+1, $^{79}$Br)$^+$ Preparation 90

1-[4-(4-Bromo-pyrazol-1-yl)-piperidin-1-yl]-ethanone

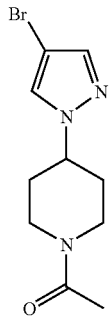

Acetyl chloride (312 μl, 4.35 mmol) is added dropwise, under stirring at 0° C., to a solution of 4-(4-Bromo-pyrazol-1-yl)-piperidine (as obtained in preparation 89, 1 g, 4.34 mmol), Et$_3$N (1.824 ml, 13.04 mmol) in CH$_2$Cl$_2$. The cooling bath is then removed and the reaction mixture stirred at RT for an additional 1 h. The mixture is then diluted with de-ionized water and the phases are separated. The organic phase is washed several times with de-ionized water and the aqueous layer re-extracted with CH$_2$Cl$_2$. The combined organic layers are washed with brine, dried over Na$_2$SO$_4$, filtered and the filtrate is concentrated in vacuo. The residue is used without further purification in the next step, and afford the title compound as yellow solid, R$_t$=0.786 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 272 (M+1, $^{79}$Br)$^+$ Preparation 91

1-{4-[4-(4,4,5,5-Tetramethyl-[1,3,2]dioxaborolan-2-yl)-pyrazol-1-yl]-piperidin-1-yl}-ethanone

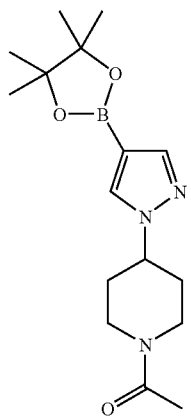

The title compound is obtained analogously to Preparation 1, but using 1-[4-(4-Bromo-pyrazol-1-yl)-piperidin-1-yl]-ethanone (as obtained in preparation 90).

Preparation 92 and 93

NaH (60% in mineral oil, 410 mg, 10.2 mmol) is added portionwise to a stirred solution of 4-bromo-3-methylpyrazole (1.69 g, 10.2 mmol) in DMF (20 ml). The resulting mixture is stirred for 1 h at 0° C. and 4-Methanesulfonyloxy-piperidine-1-carboxylic acid tert-butyl ester (as obtained in preparation 61, 2.839 g, 10.16 mmol) is added. The resulting pale suspension is heated at 95° C. for 1 h. The reaction is quenched with water and extracted with EtOAc several times. The combined organic layers are washed with brine, dried over Na$_2$SO$_4$, filtered and the filtrate is concentrated in vacuo. The residue is purified by chromatography on a 120 g silica gel column on a Combiflash Companion™ (Isco Inc.) apparatus (gradient hexanes:TBDME from 1:0=>1:1) to afford the two regioisomers identified by preparation 92 and preparation 93.

Preparation 92

4-(4-Bromo-5-methyl-pyrazol-1-yl)-piperidine-1-carboxylic acid tert-butyl ester

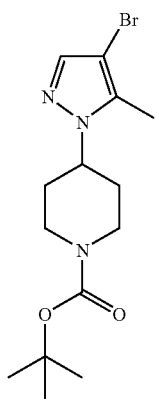

$R_t$=1.252 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+ 0.1% TFA, flow rate 1.0 ml/min); MS: 344 (M+1, $^{79}Br$)$^+$.

Preparation 93

4-(4-Bromo-3-methyl-pyrazol-1-yl)-piperidine-1-carboxylic acid tert-butyl ester

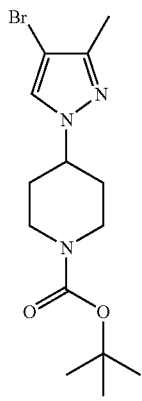

$R_t$=1.247 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+ 0.1% TFA, flow rate 1.0 ml/min); MS: 344 (M+1, $^{79}Br$)$^+$.

Preparation 94

4-[5-Methyl-4-(4,4,5,5-tetramethyl-[1,3,2]dioxaborolan-2-yl)-pyrazol-1-yl]-piperidine-1-carboxylic acid tert-butyl ester

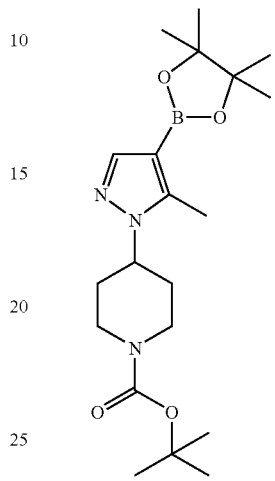

The title compound is obtained analogously to Preparation 1, but using 4-(4-Bromo-5-methyl-pyrazol-1-yl)-piperidine-1-carboxylic acid tert-butyl ester (as obtained in preparation 92).

Preparation 95

4-[3-Methyl-4-(4,4,5,5-tetramethyl-[1,3,2]dioxaborolan-2-yl)-pyrazol-1-yl]-piperidine-1-carboxylic acid tert-butyl ester

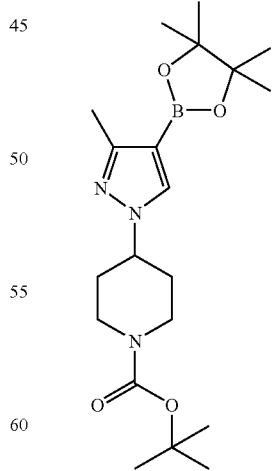

The title compound is obtained analogously to Preparation 1, but using 4-(4-Bromo-3-methyl-pyrazol-1-yl)-piperidine-1-carboxylic acid tert-butyl ester (as obtained in preparation 93).

Preparation 96

4-(4-Bromo-pyrazol-1-yl)-1-cyclopropyl-piperidine

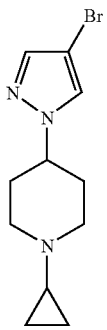

Acetic acid (1.258 ml, 21.98 mmol) is added dropwise, under stirring at RT, to a solution of 4-(4-Bromo-pyrazol-1-yl)-piperidine (as obtained in preparation 89, 1.686 g, 7.327 mmol) and [(1-ethoxy-1-cyclopropyl)oxy]trimethylsilane (2.210 ml, 10.99 mmol) in MeOH (20 ml). Sodium cyanoborohydride (775 mg, 11.7) is then added in one portion at RT. The mixture is then heated at 60° C. for 3 h. After cooling, the reaction mixture is concentrated in vacuo and the residue dissolved in EtOAc and diluted with saturated NaHCO$_3$. After separation, the aqueous phase is re-extracted 3× with EtOAc. The combined organic layers are washed with brine, dried over Na$_2$SO$_4$, filtered and the filtrate is concentrated in vacuo. The residue is used without further purification in the next step, and afford the title compound as colorless solid, R$_t$=0.618 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 270 (M+1, $^{79}$Br)$^+$

Preparation 97

1-Cyclopropyl-4-[4-(4,4,5,5-tetramethyl-[1,3,2]dioxaborolan-2-yl)-pyrazol-1-yl]-piperidine

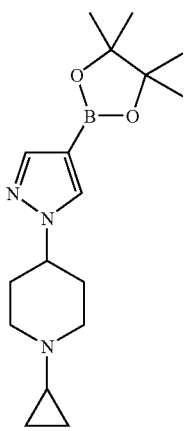

The title compound is obtained analogously to Preparation 1, but using 4-(4-Bromo-pyrazol-1-yl)-1-cyclopropyl-piperidine (as obtained in preparation 96).

Preparation 98

(rac)-3-Methanesulfonyloxymethyl-piperidine-1-carboxylic acid tert-butyl ester

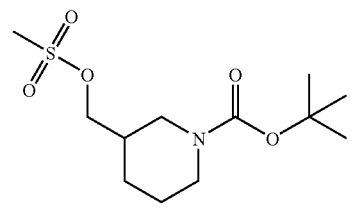

The title compound is obtained analogously to Preparation 61, but using 3-Hydroxymethyl-piperidine-1-carboxylic acid tert-butyl ester.

Preparation 99

(rac)-3-(4-Bromo-pyrazol-1-ylmethyl)-piperidine-1-carboxylic acid tert-butyl ester

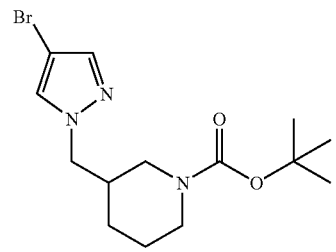

The title compound is obtained analogously to Preparation 62, but using (rac)-3-Methanesulfonyloxymethyl-piperidine-1-carboxylic acid tert-butyl ester (as obtained in preparation 98).

Preparation 100

(rac)-3-[4-(4,4,5,5-Tetramethyl-[1,3,2]dioxaborolan-2-yl)-pyrazol-1-ylmethyl]-piperidine-1-carboxylic acid tert-butyl ester

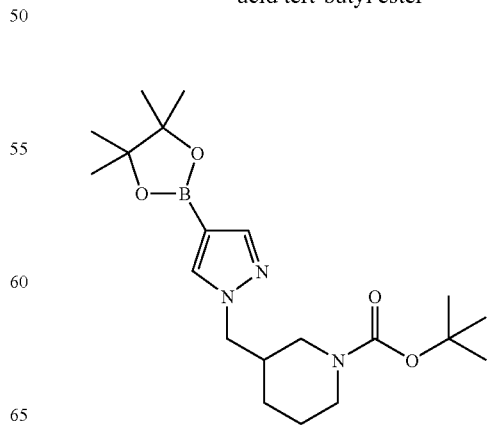

The title compound is obtained analogously to Preparation 1, but using (rac)-3-(4-Bromo-pyrazol-1-ylmethyl)-piperidine-1-carboxylic acid tert-butyl ester (as obtained in preparation 99).

Preparation 101

4-[4-(4,4,5,5-Tetramethyl-[1,3,2]dioxaborolan-2-yl)-pyrazol-1-ylmethyl]-piperidine-1-carboxylic acid tert-butyl ester

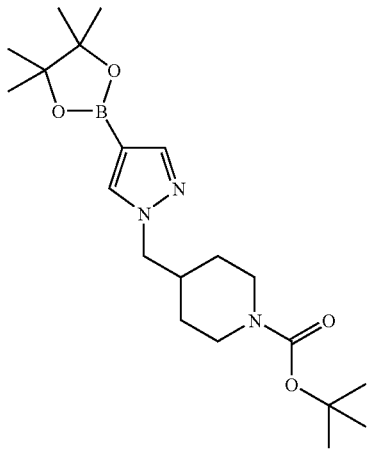

The title compound is obtained analogously to Preparation 100, but using 4-(4-Bromo-pyrazol-1-ylmethyl)-piperidine-1-carboxylic acid tert-butyl ester (obtained analogously to preparation 99 from 4-Methanesulfonyloxymethyl-piperidine-1-carboxylic acid tert-butyl ester).

Preparation 102

4-[3,5-Dimethyl-4-(4,4,5,5-tetramethyl-[1,3,2]dioxaborolan-2-yl)-pyrazol-1-yl]-piperidine-1-carboxylic acid tert-butyl ester

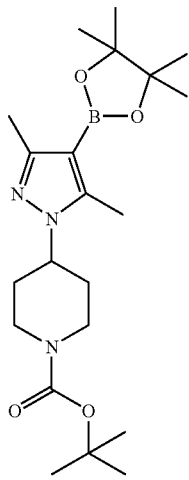

The title compound is obtained analogously to Preparation 1, but using 4-(4-Bromo-3,5-dimethyl-pyrazol-1-yl)-piperidine-1-carboxylic acid tert-butyl ester (obtained analogously to preparation 92 from 4-Bromo-3,5-dimethyl-1H-pyrazole).

Preparation 103

(rac)-3-[4-(4,4,5,5-Tetramethyl-[1,3,2]dioxaborolan-2-yl)-pyrazol-1-yl]-piperidine-1-carboxylic acid tert-butyl ester

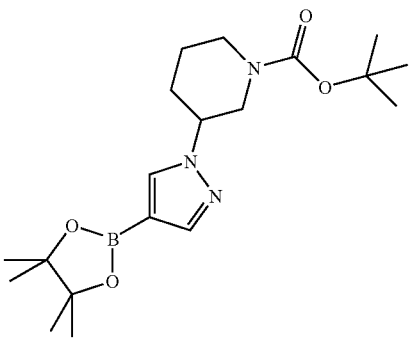

The title compound is obtained analogously to Preparation 100, but using (rac)-3-(4-Bromo-pyrazol-1-yl)-piperidine-1-carboxylic acid tert-butyl ester (obtained analogously to preparation 99 from (rac)-3-Methanesulfonyloxy-piperidine-1-carboxylic acid tert-butyl ester).

Preparation 104

1-(5-Bromo-2-methoxy-phenyl)-4-methyl-piperazine

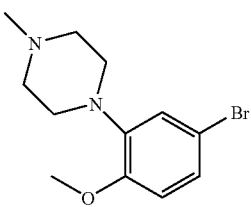

A mixture of 5-bromo-2-methoxyaniline (2.00 g, 9.60 mmol) and bis(2-chloroethyl)-methylaminde hydrochloride (2.04 g, 10.4 mmol) in xylene (40 ml) is heated to reflux (155° C., oilbath) for 29 h. After cooling to RT, the xylene layer is washed with $H_2O$ (3×). The organic layer is discarded and the pH of the aqueous layer is adjusted to pH>13. The aqueous layer is extracted with $CH_2Cl_2$ (3×). The combined organic layers are dried ($Na_2SO_4$), filtered, concentrated under reduced pressure, and put under HV overnight to afford the title compound as a brown solid, $R_t$=4.8 min (HPLC conditions B); MS: 287 (M+1)$^+$

Preparation 105

1-[2-Methoxy-5-(4,4,5,5-tetramethyl-[1,3,2]dioxaborolan-2-yl)-phenyl]-4-methyl-piperazine

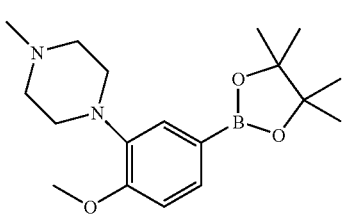

The title compound is obtained analogously to Preparation 1, but using 1-(5-Bromo-2-methoxy-phenyl)-4-methyl-piperazine (as obtained in preparation 104).

Preparation 106

(4-Bromo-1-methyl-1H-pyrrol-2-yl)-(4-methyl-piperazin-1-yl)-methanone

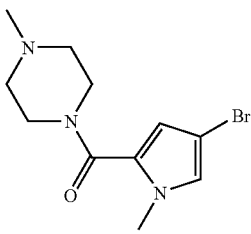

The title compound is obtained analogously to Preparation 12, but using 4-Bromo-1-methyl-1H-pyrrole-2-carboxylic acid.

Preparation 107

(4-Methyl-piperazin-1-yl)-[1-methyl-4-(4,4,5,5-tetramethyl-[1,3,2]dioxaborolan-2-yl)-1H-pyrrol-2-yl]-methanone

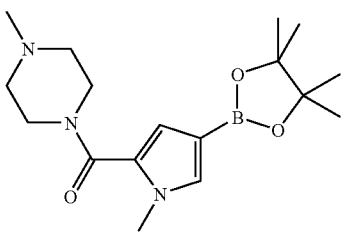

The title compound is obtained analogously to Preparation 1, but using (4-Bromo-1-methyl-1H-pyrrol-2-yl)-(4-methyl-piperazin-1-yl)-methanone (as obtained in preparation 106).

Example 1

{3-Fluoro-4-[3-(3,4,5-trimethoxy-phenyl)-quinoxalin-5-yl]-phenyl}-morpholin-4-yl-methanone

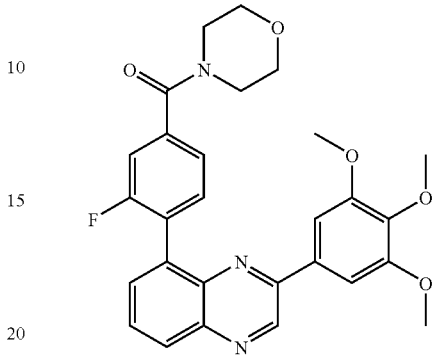

A microwave tube is charged with 50 mg (0.133 mmol) of 8-Bromo-2-(3,4,5-trimethoxy-phenyl)-quinoxaline, 50.6 mg (ca. 0.140 mmol) of (4-Boronic acid-2-fluoro-phenyl)-morpholin-4-yl-methanone, 5.1 mg (0.012 mmol) of S-Phos, 87 mg (0.4 mmol) of $K_3PO_4$ and 0.9 mg (0.004 mmol) of $Pd(OAc)_2$. After several cycles of vacuum/purge with argon, 3 ml of a mixture consisting of 36 µl deionized water in 15 ml 1,2-dimethoxy-ethane, are added. The reaction mixture is then heated to 105° C. for 2 h 30. After cooling, the reaction mixture is diluted with $CH_2Cl_2$, poured onto a saturated solution of $Na_2CO_3$ and extracted 3× with $CH_2Cl_2$. The combined organic layers are washed with water, brine, dried over $Na_2SO_4$, filtered and the filtrate is concentrated in vacuo. The residue is purified by chromatography (silicagel, $CH_2Cl_2$:EtOH=95:5=>4:6) to afford the title compound as a yellow solid, $R_t$=1.132 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+0.1% TFA, flow rate 1.0 ml/min); MS: 500 (M+1)$^+$.

The starting materials can be prepared as follows:

Step 1.1

(3-Bromo-2-nitro-phenylamino)-acetic acid ethyl ester

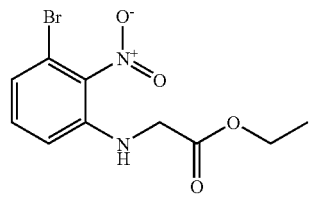

9.90 g (69.6 mmol) ethylglycinate hydrochloride are suspended under argon in 100 mL of dry DMA. 24.3 mL (139 mmol) diisopropylethylamine and 10.21 g (46.4 mmol) of 2-bromo-6-fluoronitrobenzene are then added at RT. The orange solution is then heated to 80° C. for 16 h. After cooling, the reaction mixture is poured onto iced-cold water and the suspension is collected by filtration to afford, after drying in HV at 50° C., the title compound as a dark orange solid, which is used in the next step without further purification.

Step 1.2

8-Bromo-3,4-dihydro-1H-quinoxalin-2-one

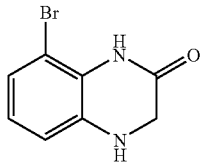

10.33 g (ca. 25.9 mmol) (3-Bromo-2-nitro-phenylamino)-acetic acid ethyl ester is hydrogenated in the presence of 2.84 g Ra—Ni (B113W EtOH, Degussa) in 340 ml of THF:EtOH=1:1 for 20 h. The reaction mixture is filtered on hyflo and the filtrate is concentrated in vacuo. A mixture of the title compound with uncyclized (2-Amino-3-bromo-phenylamino)-acetic acid ethyl ester is obtained and used as obtained in the next synthetic step.

Step 1.3

8-Bromo-1H-quinoxalin-2-one

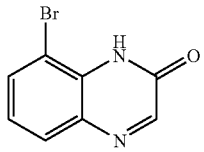

A sealable tube is charged with 4.99 g (39.549 mmol) of a mixture of 8-Bromo-3,4-dihydro-1H-quinoxalin-2-one with (2-Amino-3-bromo-phenylamino)-acetic acid ethyl ester (as obtained in step 1.2). 50 mL of a 1M NaOH solution and 12.1 ml of a 30% $H_2O_2$ aqueous solution are added. The tube is sealed and heated to 95° C. for 1 h. After cooling, 50 mL of 1M HCl solution are added slowly and the brown solid is collected by filtration, to afford, after drying in HV at 50° C., the title compound which is used without further purification.

Step 1.4

8-Bromo-2-chloro-quinoxaline

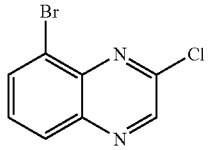

A mixture of 2.0 g (ca. 7.64 mmol) 8-Bromo-1H-quinoxalin-2-one and 36 ml of $POCl_3$ is heated to 50° C. for 16 h. After cooling, the excess of $POCl_3$ is evaporated, water is then added and extracted 3× with $CH_2Cl_2$. The combined organic layers are successively washed with water, $NaHCO_3$, saturated brine, dried over $Na_2SO_4$, filtered and the filtrate is concentrated in vacuo. The residue is purified by chromatography (silicagel, hexane:CH2Cl2=7:3=>1:1) to afford the title compound as a pale orange solid, MS: 243 (M)$^+$

Step 1.5

8-Bromo-2-(3,4,5-trimethoxy-phenyl)-quinoxaline

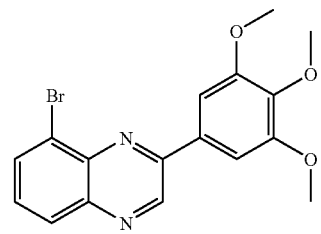

A microwave tube is charged with 30 mg (0.123 mmol) of 8-Bromo-2-chloro-quinoxaline, 26.4 mg (0.123 mmol) of 3,4,5-trimethoxyphenylboronic acid, 40 mg (0.370 mmol) of $Na_2CO_3$ and 4.4 mg (0.0037 mmol) of $Pd(PPh_3)_4$. After several cycles of vacuum/purge with argon, 1.5 ml of dry DMF are added. The reaction mixture is then heated tot 105° C. for 15 h. After cooling, the yellow suspension is poured onto de-ionized water and filtered. After drying under H.V. at 50° C., the residue is purified by chromatography (silicagel, hexane:EtOAc=100=>1:1) to afford the title compound as a yellow solid, $R_t$=1.294 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+0.1% TFA, flow rate 1.0 ml/min); MS: 375 (M)$^+$.

Using the same synthetic methods as described in Example 1, reaction of 8-Bromo-2-(3,4,5-trimethoxy-phenyl)-quinoxaline and the appropriate boronic acid or ester derivative leads to the following Examples:

Example 2

8-(4-Methanesulfonyl-phenyl)-2-(3,4,5-trimethoxyphenyl)-quinoxaline

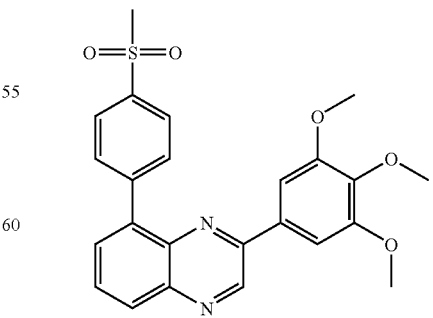

$R_t$=1.142 min (Acquity HPLC BEH C18, 2.1×50 mm, 1.7 micron, detection 215 nM, 0.1 min 2% $CH_3CN$ in $H_2O$, 2% to 100% CH$_3$CN in H$_2$O in 1.5 min, 0.4 min 100% CH$_3$CN+ 0.1% TFA, flow rate 1.0 ml/min); MS: 451 (M+1)$^+$.

Example 3

8-(4-Ethanesulfonyl-phenyl)-2-(3,4,5-trimethoxy-phenyl)-quinoxaline

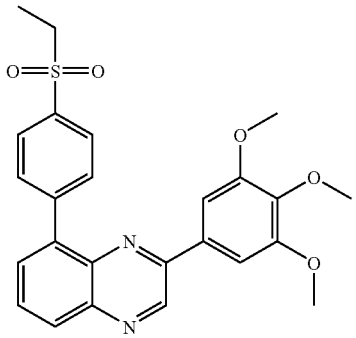

R$_t$=1.061 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 465 (M+1)$^+$.

Example 4

8-[4-(Propane-2-sulfonyl)-phenyl]-2-(3,4,5-tri-methoxy-phenyl)-quinoxaline

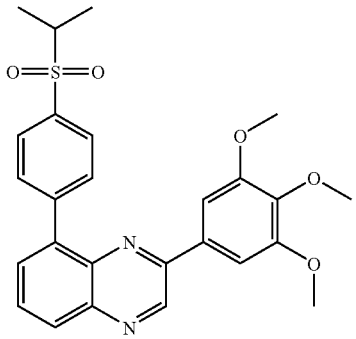

R$_t$=1.217 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 479 (M+1)$^+$.

Example 5

4-[3-(3,4,5-Trimethoxy-phenyl)-quinoxalin-5-yl]-benzenesulfonamide

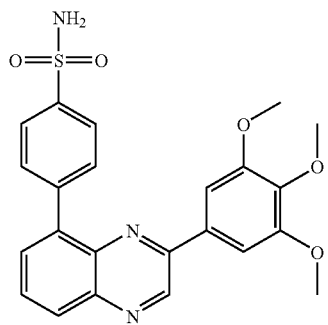

R$_t$=1.049 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 452 (M+1)$^+$.

Example 6

N-Methyl-4-[3-(3,4,5-trimethoxy-phenyl)-quinoxa-lin-5-yl]-benzenesulfonamide

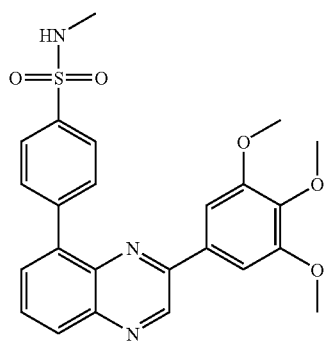

R$_t$=1.144 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 466 (M+1)$^+$.

Example 7

N-Ethyl-4-[3-(3,4,5-trimethoxy-phenyl)-quinoxalin-5-yl]-benzenesulfonamide

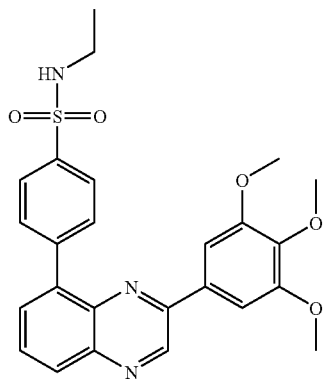

$R_t$=1.061 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 480 (M+1)$^+$.

Example 8

N,N-Dimethyl-4-[3-(3,4,5-trimethoxy-phenyl)-quinoxalin-5-yl]-benzenesulfonamide

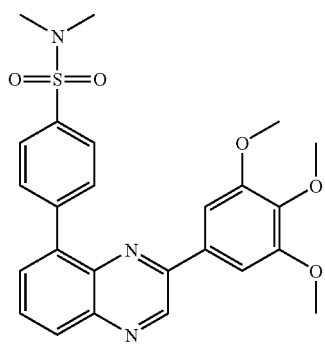

$R_t$=1.061 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 480 (M+1)$^+$.

Example 9

N-Methyl-4-[3-(3,4,5-trimethoxy-phenyl)-quinoxalin-5-yl]-benzamide

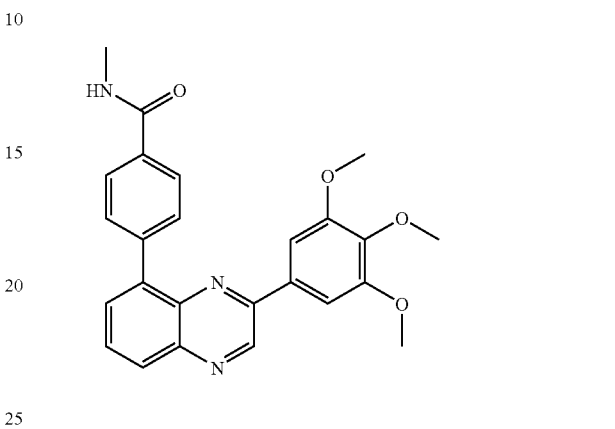

$R_t$=1.063 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 430 (M+1)$^+$.

Example 10

Morpholin-4-yl-{4-[3-(3,4,5-trimethoxy-phenyl)-quinoxalin-5-yl]-phenyl}-methanone

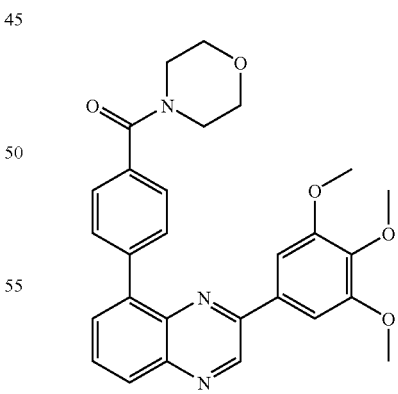

$R_t$=1.093 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 486 (M+1)$^+$.

Example 11

1-Morpholin-4-yl-2-{4-[3-(3,4,5-trimethoxy-phenyl)-quinoxalin-5-yl]-phenyl}-ethanone

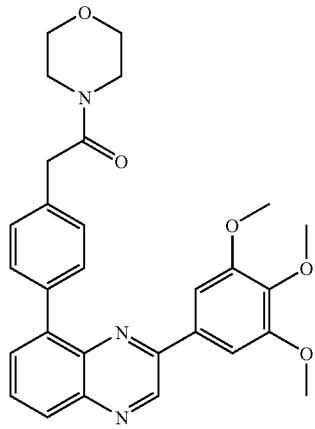

R$_t$=1.113 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 500 (M+1)$^+$.

Example 12

N-{4-[3-(3,4,5-Trimethoxy-phenyl)-quinoxalin-5-yl]-phenyl}-methanesulfonamide

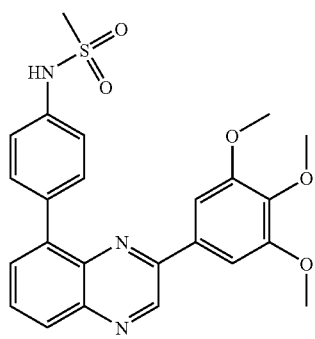

R$_t$=1.122 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 466 (M+1)$^+$.

Example 13

1-(1,1-Dioxido-thiomorpholin-4-yl)-2-{4-[3-(3,4,5-trimethoxy-phenyl)-quinoxalin-5-yl]-phenyl}-ethanone

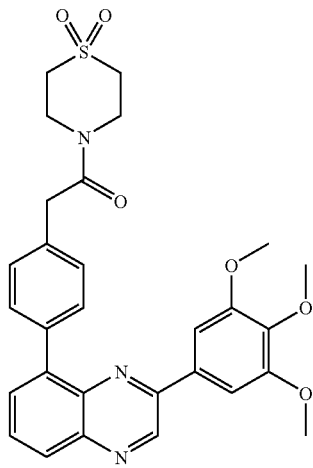

R$_t$=1.079 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 548 (M+1)$^+$.

Example 14

1-(4-Methyl-piperazin-1-yl)-2-{4-[3-(3,4,5-trimethoxy-phenyl)-quinoxalin-5-yl]-phenyl}-ethanone

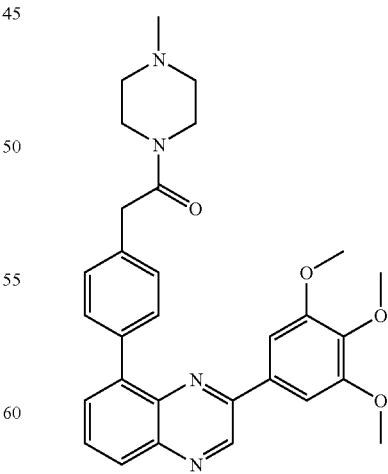

R$_t$=0.917 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 513 (M+1)$^+$.

Example 15

8-(4-Morpholin-4-ylmethyl-phenyl)-2-(3,4,5-trimethoxy-phenyl)-quinoxaline

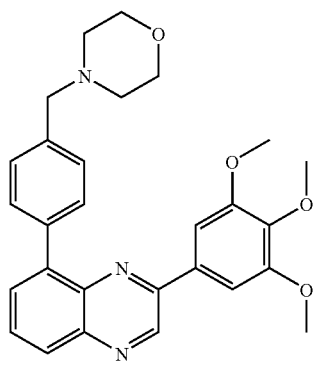

R$_t$=0.920 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 472 (M+1)$^+$.

Example 16

{2-Methyl-4-[3-(3,4,5-trimethoxy-phenyl)-quinoxalin-5-yl]-phenyl}-morpholin-4-yl-methanone

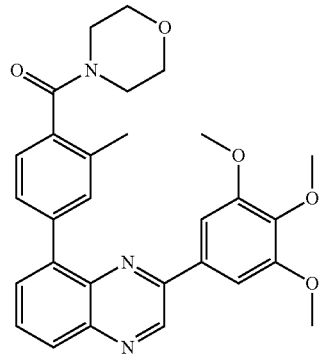

R$_t$=1.155 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 500 (M+1)$^+$.

Example 17

2-Fluoro-4-[3-(3,4,5-trimethoxy-phenyl)-quinoxalin-5-yl]-phenyl}-morpholin-4-yl-methanone

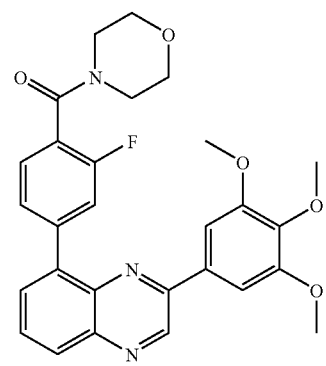

R$_t$=1.158 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 504 (M+1)$^+$.

Example 18

{2-Chloro-4-[3-(3,4,5-trimethoxy-phenyl)-quinoxalin-5-yl]-phenyl}-morpholin-4-yl-methanone

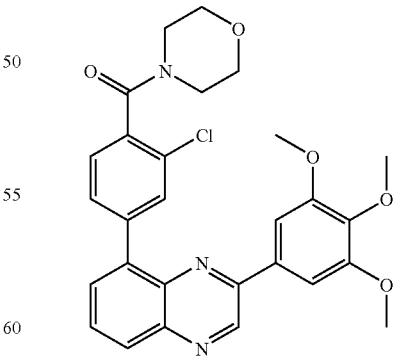

R$_t$=1.184 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 520 (M+1)$^+$.

Example 19

8-[4-(1,1-Dioxido-thiomorpholin-4-ylmethyl)-phenyl]-2-(3,4,5-trimethoxy-phenyl)-quinoxaline

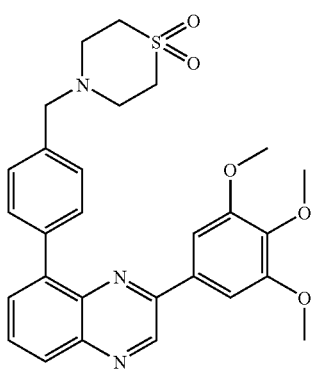

R$_t$=0.969 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 520 (M+1)$^+$.

Example 20

8-(3-Fluoro-4-morpholin-4-ylmethyl-phenyl)-2-(3,4,5-trimethoxy-phenyl)-quinoxaline

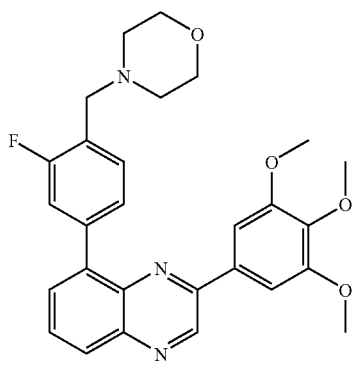

R$_t$=0.932 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 490 (M+1)$^+$.

Example 21

8-(3-Methyl-4-morpholin-4-ylmethyl-phenyl)-2-(3,4,5-trimethoxy-phenyl)-quinoxaline

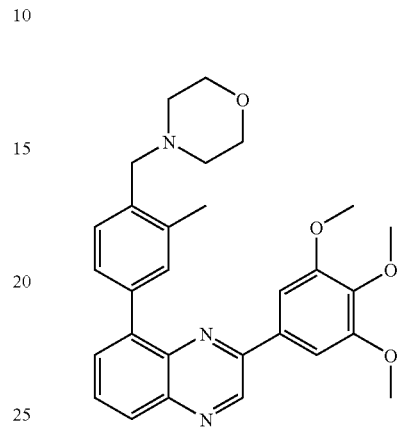

R$_t$=0.947 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 486 (M+1)$^+$.

Using the same synthetic methods as described in Example 1, but utilizing 8-Bromo-2-(3,4-dimethoxy-phenyl)-quinoxaline [prepared analogously to step 1.5 but utilizing 4,5-dimethoxyphenylboronic acid in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples

Example 22

4-[3-(3,4-Dimethoxy-phenyl)-quinoxalin-5-yl]-N-methyl-benzenesulfonamide

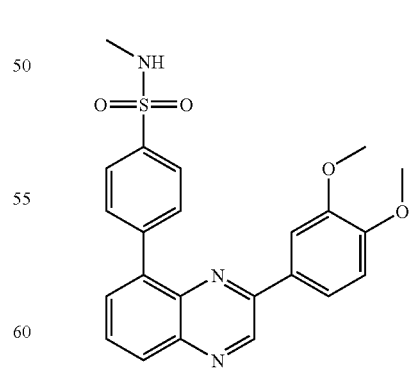

R$_t$=1.124 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 436 (M+1)$^+$.

Example 23

2-(3,4-Dimethoxy-phenyl)-8-(4-methanesulfonyl-phenyl)-quinoxaline

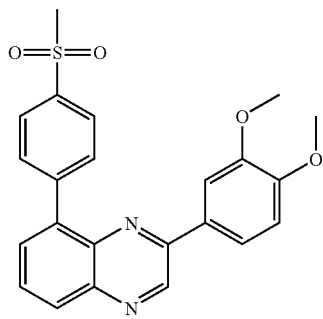

$R_t$=1.116 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+ 0.1% TFA, flow rate 1.0 ml/min); MS: 421 $(M+1)^+$.

Using the same synthetic methods as described in Example 1, but utilizing 8-Bromo-2-(3,4-diethoxy-phenyl)-quinoxaline [prepared analogously to step 1.5 but utilizing 4,5-diethoxyphenylboronic acid in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples

Example 24

2-(3,4-Diethoxy-phenyl)-8-(4-methylsulfanylmethyl-phenyl)-quinoxaline

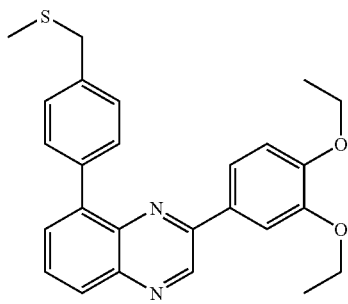

$R_t$=1.550 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+ 0.1% TFA, flow rate 1.0 ml/min); MS: 431 $(M+1)^+$.

Example 25

2-(3,4-Diethoxy-phenyl)-8-(4-methanesulfonylmethyl-phenyl)-quinoxaline

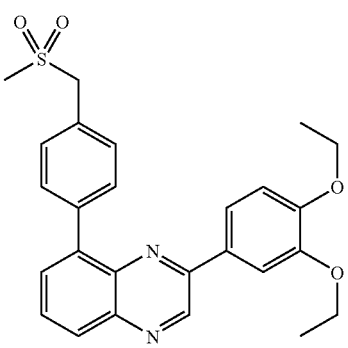

A microwave tube is charged with 23 mg (0.053 mmol) of 2-(3,4-Diethoxy-phenyl)-8-(4-methylsulfanylmethyl-phenyl)-quinoxaline, 2 ml AcOH and 20 μl (0.2 mmol) of a 30% aqueous $H_2O_2$ solution. The tube is sealed and heated to reflux for 30 min. After cooling, the reaction mixture is diluted with EtOAc and washed three time with 2M NaOH solution, once with a 10% $Na_2S_2O_3$ solution and finally with de-ionized water. The organic layers is washed dried over $Na_2SO_4$, filtered and the filtrate is concentrated in vacuo. The residue is purified by preparative HPLC ($H_2O$/MeCN with 0.05% TFA 1:0=>0:1) to afford the title compound as a yellow solid, $R_t$=1.243 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+0.1% TFA, flow rate 1.0 ml/min); MS: 463 $(M+1)^+$.

Example 26

2-{4-[3-(3,4-Diethoxy-phenyl)-quinoxalin-5-yl]-phenyl}-1-morpholin-4-yl-ethanone

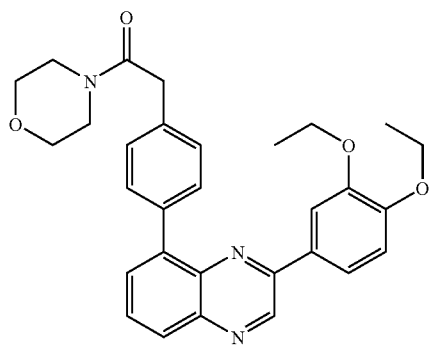

$R_t$=1.260 min (Acquity HPLC BEH C18, 2.1×50 mm, 1.7 micron, detection 215 nM, 0.1 min 2% $CH_3CN$ in $H_2O$, 2% to 100% CH$_3$CN in H$_2$O in 1.5 min, 0.4 min 100% CH$_3$CN+ 0.1% TFA, flow rate 1.0 ml/min); MS: 498 (M+1)$^+$.

Example 27

2-{4-[3-(3,4-Diethoxy-phenyl)-quinoxalin-5-yl]-phenyl}-1-(1,1-dioxido-thiomorpholin-4-yl)-ethanone

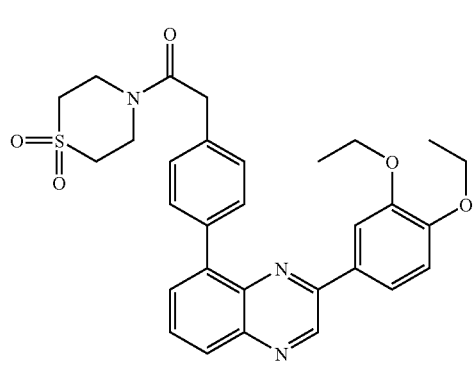

R$_t$=1.212 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 546 (M+1)$^+$.

Example 28

{4-[3-(3,4-Diethoxy-phenyl)-quinoxalin-5-yl]-2-fluoro-phenyl}-morpholin-4-yl-methanone

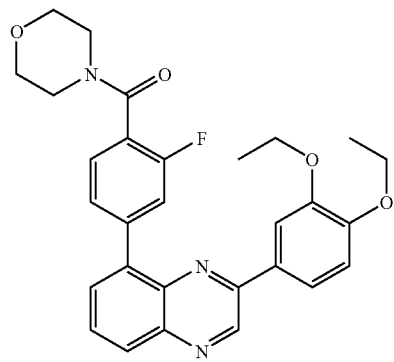

R$_t$=1.276 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 502 (M+1)$^+$.

Example 29

N-{4-[3-(3,4-Diethoxy-phenyl)-quinoxalin-5-yl]-phenyl}-methanesulfonamide

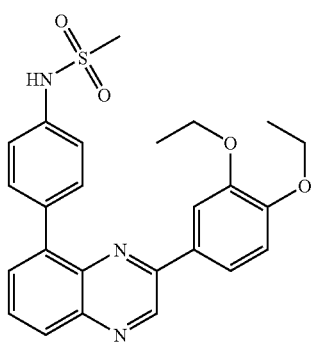

R$_t$=1.254 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 464 (M+1)$^+$.

Example 30

2-{4-[3-(3,4-Diethoxy-phenyl)-quinoxalin-5-yl]-2-fluoro-phenyl}-1-morpholin-4-yl-ethanone

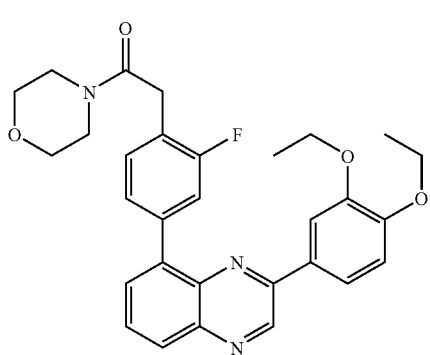

R$_t$=1.291 min (Acquity HPLC BEH C18, 2.1×50 mm, 1.7 micron, detection 215 nM, 0.1 min 2% CH$_3$CN in H$_2$O, 2% to 100% CH₃CN in H₂O in 1.5 min, 0.4 min 100% CH₃CN+ 0.1% TFA, flow rate 1.0 ml/min); MS: 516 (M+1)⁺.

Example 31

{4-[3-(3,4-Diethoxy-phenyl)-quinoxalin-5-yl]-2-fluoro-phenyl}-(1,1-dioxido-thiomorpholin-4-yl)-methanone

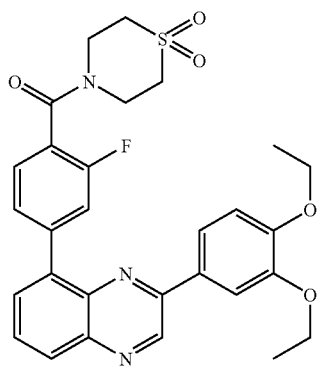

R$_t$=1.217 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 550 (M+1)⁺.

Example 32

2-(3,4-Diethoxy-phenyl)-8-[4-(1,1-dioxido-thiomorpholin-4-ylmethyl)-3-methyl-phenyl]-quinoxaline

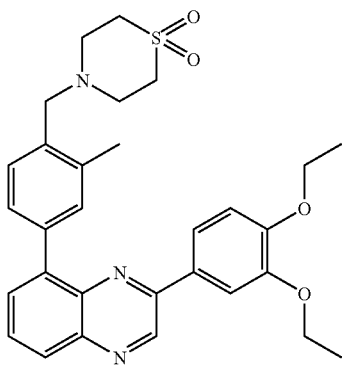

R$_t$=1.153 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 532 (M+1)⁺.

Using the same synthetic methods as described in Example 1, but utilizing 8-Bromo-2-[3-methoxy-4-(2-morpholin-4-yl-ethoxy)-phenyl]-quinoxaline [prepared analogously to step 1.5 but utilizing 4-{2-[2-Methoxy-4-(4,4,5,5-tetramethyl-[1,3,2]dioxaborolan-2-yl)-phenoxy]-ethyl}-morpholine (CAS 864754-10-9) in lieu of 3,4,5-trimethoxyphenyl-boronic acid] in lieu of 8-Bromo-2-(3,4,5-trimethoxy-phenyl)-quinoxaline and the appropriate boronic acid or ester derivative leads to the following Examples Example 33

8-(4-Ethanesulfonyl-phenyl)-2-[3-methoxy-4-(2-morpholin-4-yl-ethoxy)-phenyl]-quinoxaline

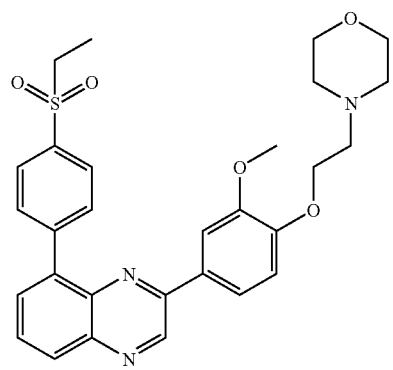

R$_t$=0.923 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 534 (M+1)⁺.

Example 34

2-(4-{3-[3-Methoxy-4-(2-morpholin-4-yl-ethoxy)-phenyl]-quinoxalin-5-yl}-phenyl)-1-morpholin-4-yl-ethanone

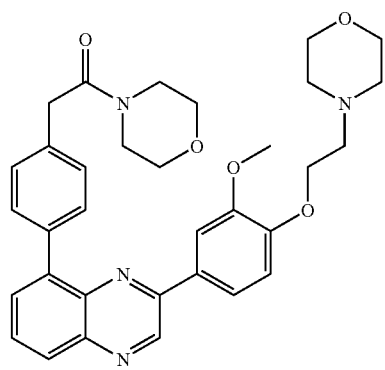

R$_t$=0.905 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 569 (M+1)⁺.

Example 35

(2-Fluoro-4-{3-[3-methoxy-4-(2-morpholin-4-yl-ethoxy)-phenyl]-quinoxalin-5-yl}-phenyl)-morpholin-4-yl-methanone

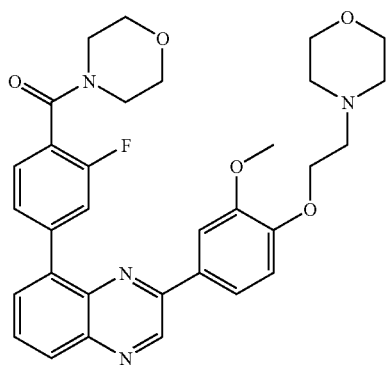

$R_t$=0.900 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 573 (M+1)$^+$.

Example 36

N-(4-{3-[3-Methoxy-4-(2-morpholin-4-yl-ethoxy)-phenyl]-quinoxalin-5-yl}-phenyl)-methanesulfonamide

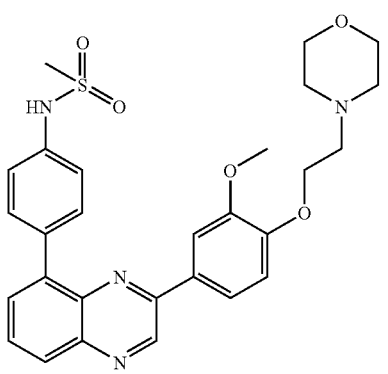

$R_t$=0.903 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 535 (M+1)$^+$.

Example 37

8-(4-Methanesulfonylmethyl-phenyl)-2-[3-methoxy-4-(2-morpholin-4-yl-ethoxy)-phenyl]-quinoxaline

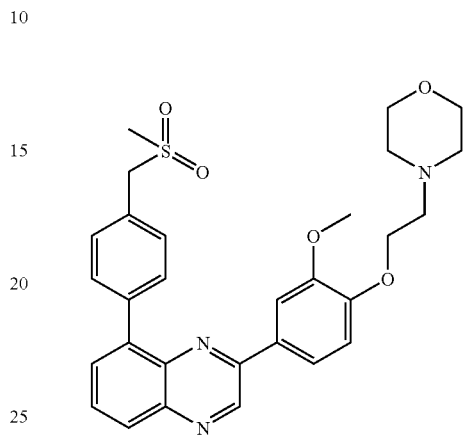

$R_t$=0.894 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 534 (M+1)$^+$.

Using the same synthetic methods as described in Example 1, but utilizing N-[3-(8-Bromo-quinoxalin-2-yl)-phenyl]-methanesulfonamide [prepared analogously to step 1.1 but utilizing [3-[(Methylsulfonyl)amino]phenyl]boronic acid in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples.

Example 38

N-(3-{8-[4-(2-Morpholin-4-yl-2-oxo-ethyl)-phenyl]-quinoxalin-2-yl}-phenyl)-methanesulfonamide

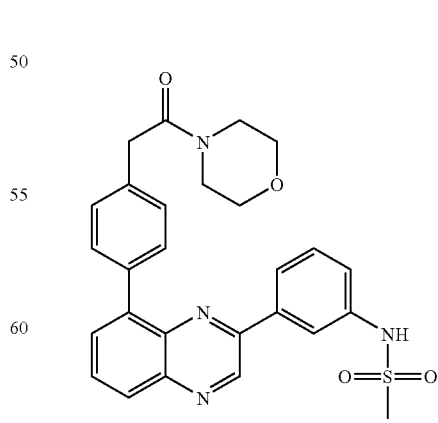

$R_t$=1.008 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 503 (M+1)$^+$.

Example 39

N-{3-[8-(4-Ethanesulfonyl-phenyl)-quinoxalin-2-yl]-phenyl}-methanesulfonamide

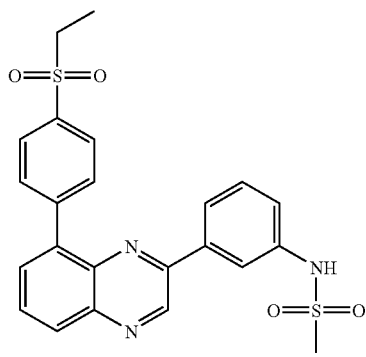

R$_t$=1.056 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 468 (M+1)$^+$.

Using the same synthetic methods as described in Example 1, but utilizing [4-(8-Bromo-quinoxalin-2-yl)-2-methyl-phenyl]-(4-methyl-piperazin-1-yl)-methanone [prepared analogously to step 1.5 but utilizing (4-Methyl-piperazin-1-yl)-[2-methyl-4-(4,4,5,5-tetramethyl-[1,3,2]dioxaborolan-2-yl)-phenyl]-methanone in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples Example 40

(4-{8-[4-(1,1-Dioxido-thiomorpholin-4-ylmethyl)-phenyl]-quinoxalin-2-yl}-2-methyl-phenyl)-(4-methyl-piperazin-1-yl)-methanone

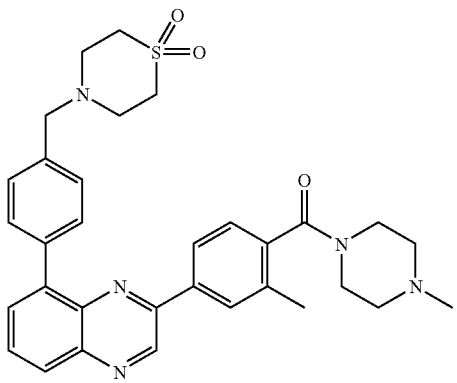

R$_t$=0.752 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 570 (M+1)$^+$.

Example 41

2-(4-{3-[3-Methyl-4-(4-methyl-piperazine-1-carbonyl)-phenyl]-quinoxalin-5-yl}-phenyl)-1-morpholin-4-yl-ethanone

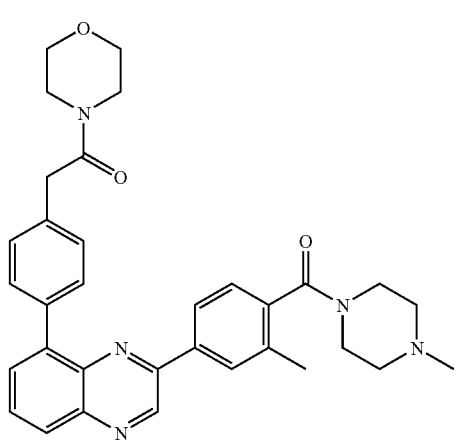

R$_t$=0.862 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 550 (M+1)$^+$.

Example 42

{4-[8-(3,5-Difluoro-4-morpholin-4-ylmethyl-phenyl)-quinoxalin-2-yl]-2-methyl-phenyl}-(4-methyl-piperazin-1-yl)-methanone

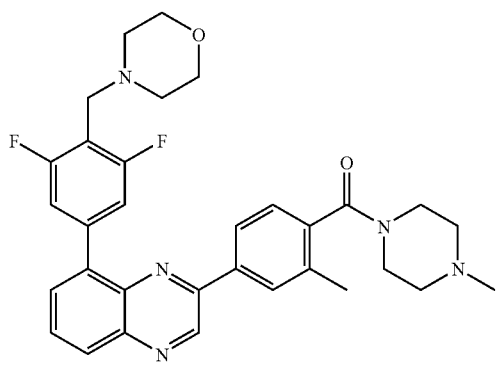

R$_t$=0.706 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 558 (M+1)$^+$.

Example 43

(4-{8-[4-(1,1-Dioxido-thiomorpholin-4-ylmethyl)-3-methyl-phenyl]-quinoxalin-2-yl}-2-methyl-phenyl)-(4-methyl-piperazin-1-yl)-methanone

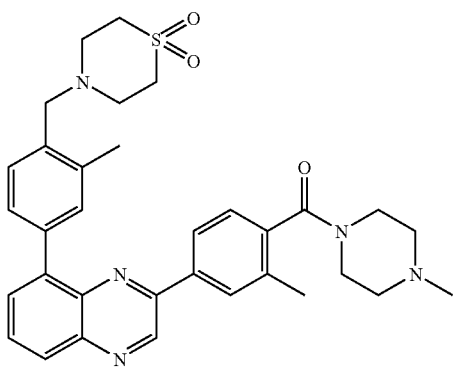

R$_t$=0.842 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 584 (M+1)$^+$.

Example 44

(4-{8-[4-(1,1-Dioxido-thiomorpholin-4-ylmethyl)-3,5-difluoro-phenyl]-quinoxalin-2-yl}-2-methyl-phenyl)-(4-methyl-piperazin-1-yl)-methanone

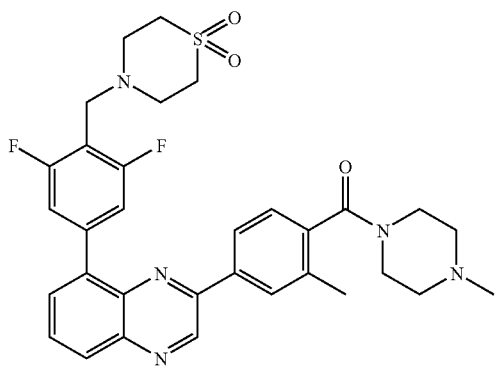

R$_t$=0.852 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 606 (M+1)$^+$ Using the same synthetic methods as described in Example 1, but utilizing 8-Bromo-2-(4-morpholin-4-yl-phenyl)-quinoxaline [prepared analogously to step 1.5 but utilizing 4-(Morpholino)phenylboronic acid in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples

Example 45

1-Morpholin-4-yl-2-{4-[3-(4-morpholin-4-yl-phenyl)-quinoxalin-5-yl]-phenyl}-ethanone

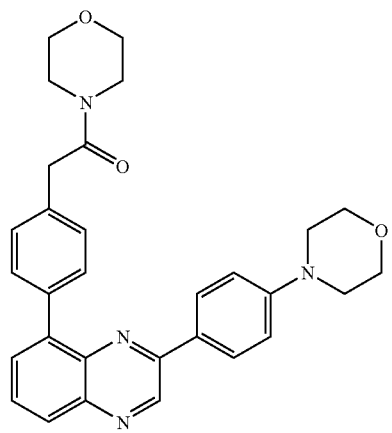

R$_t$=1.127 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 495 (M+1)$^+$.

Example 46

{2-Methyl-4-[3-(4-morpholin-4-yl-phenyl)-quinoxalin-5-yl]-phenyl}-morpholin-4-yl-methanone

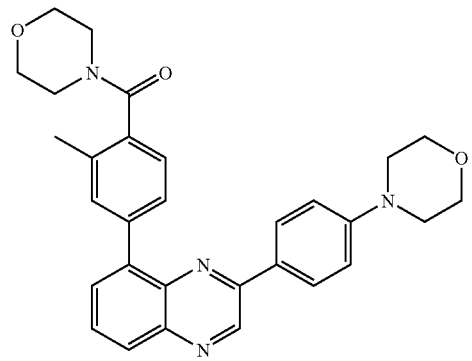

R$_t$=1.154 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 495 (M+1)$^+$.

Using the same synthetic methods as described in Example 1, but utilizing 8-Bromo-2-[3-methoxy-4-(2-methoxy-ethoxy)-phenyl]-quinoxaline [prepared analogously to step 1.5 but utilizing 2-[3-Methoxy-4-(2-methoxy-ethoxy)-phenyl]-4,4,5,5-tetramethyl-[1,3,2]dioxaborolane in lieu of 3,4,5-trimethoxyphenylboronic acid] in lieu of 8-Bromo-2-(3,4, 5-trimethoxy-phenyl)-quinoxaline and the appropriate boronic acid or ester derivative leads to the following Examples

Example 47

8-(4-Ethanesulfonyl-phenyl)-2-[3-methoxy-4-(2-methoxy-ethoxy)-phenyl]-quinoxaline

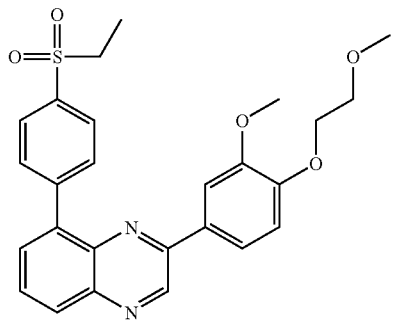

R$_t$=1.209 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 479 (M+1)$^+$.

Example 48

8-[4-(1,1-Dioxido-thiomorpholin-4-ylmethyl)-3-fluoro-phenyl]-2-[3-methoxy-4-(2-methoxy-ethoxy)-phenyl]-quinoxaline

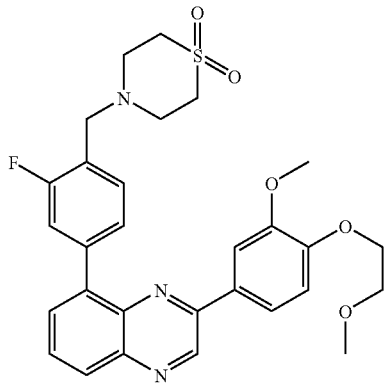

R$_t$=1.025 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 552 (M+1)$^+$.

Example 49

2-(2-Fluoro-4-{3-[3-methoxy-4-(2-methoxy-ethoxy)-phenyl]-quinoxalin-5-yl}-phenyl)-1-morpholin-4-yl-ethanone

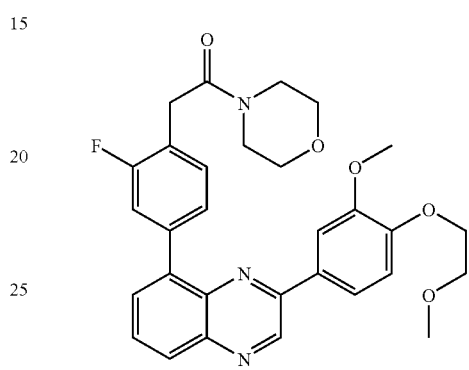

R$_t$=1.162 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 532 (M+1)$^+$

Example 50

8-(3,5-Difluoro-4-morpholin-4-ylmethyl-phenyl)-2-[3-methoxy-4-(2-methoxy-ethoxy)-phenyl]-quinoxaline

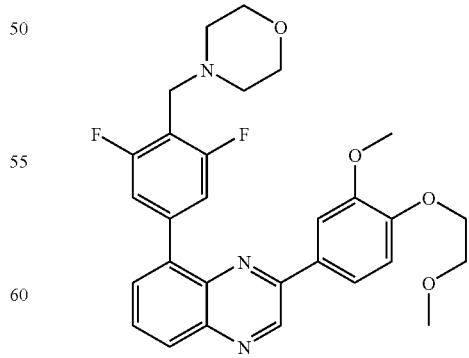

R$_t$=0.958 min (Acquity HPLC BEH C18, 2.1×50 mm, 1.7 micron, detection 215 nM, 0.1 min 2% CH$_3$CN in H$_2$O, 2% to 100% CH₃CN in H₂O in 1.5 min, 0.4 min 100% CH₃CN+ 0.1% TFA, flow rate 1.0 ml/min); MS: 522 (M+1)⁺.

Example 51

8-(3-Fluoro-4-morpholin-4-ylmethyl-phenyl)-2-[3-methoxy-4-(2-methoxy-ethoxy)-phenyl]-quinoxaline

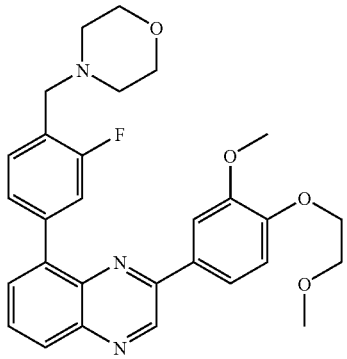

R_t=0.955 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 504 (M+1)⁺.

Example 52

8-[4-(1,1-Dioxido-thiomorpholin-4-ylmethyl)-3-methyl-phenyl]-2-[3-methoxy-4-(2-methoxy-ethoxy)-phenyl]-quinoxaline

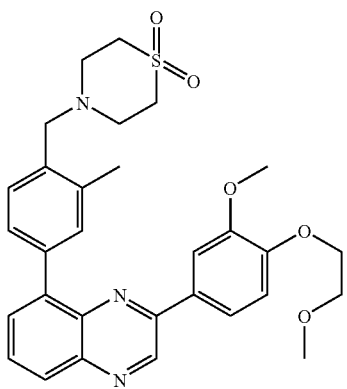

R_t=1.062 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 548 (M+1)⁺

Example 53

8-[4-(1,1-Dioxido-thiomorpholin-4-ylmethyl)-3,5-difluoro-phenyl]-2-[3-methoxy-4-(2-methoxy-ethoxy)-phenyl]-quinoxaline

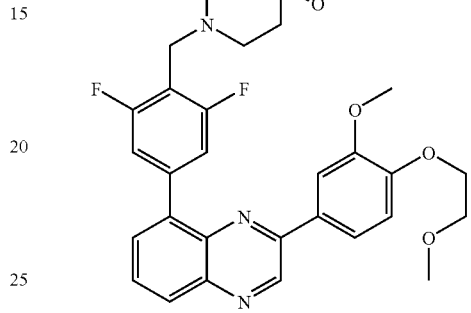

R_t=1.145 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 570 (M+1)⁺

Using the same synthetic methods as described in Example 1, but utilizing 4-(8-Bromo-quinoxalin-2-yl)-2,N,N-trimethyl-benzamide [prepared analogously to step 1.5 but utilizing 2,N,N-Trimethyl-4-(4,4,5,5-tetramethyl-[1,3,2]dioxaborolan-2-yl)-benzamide in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples Example 54

4-{8-[4-(1,1-Dioxido-thiomorpholin-4-ylmethyl)-3-fluoro-phenyl]-quinoxalin-2-yl}-2,N,N-trimethyl-benzamide

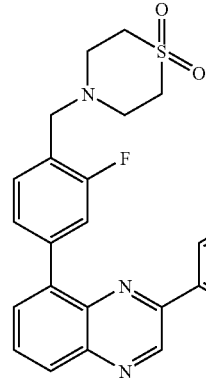

R_t=0.934 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 533 (M+1)⁺

Example 55

2,N,N-Trimethyl-4-[8-(4-morpholin-4-ylmethyl-3-trifluoromethyl-phenyl)-quinoxalin-2-yl]-benzamide

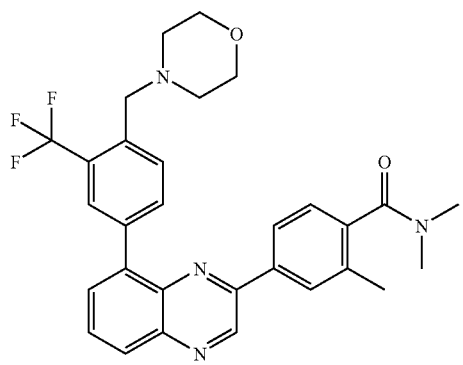

R$_t$=0.922 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 535 (M+1)⁺

Example 56

4-[8-(3-Fluoro-4-morpholin-4-ylmethyl-phenyl)-quinoxalin-2-yl]-2,N,N-trimethyl-benzamide

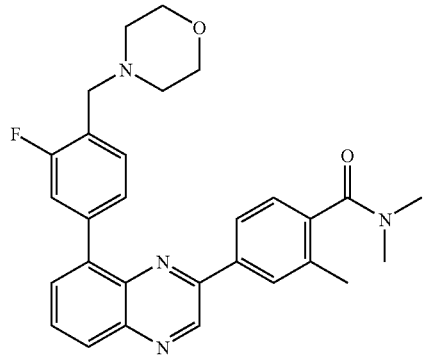

R$_t$=0.934 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 533 (M+1)⁺

Using the same synthetic methods as described in Example 1, but utilizing [4-(8-Bromo-quinoxalin-2-yl)-2-methyl-phenyl]-morpholin-4-yl-methanone [prepared analogously to step 1.5 but utilizing [2-Methyl-4-(4,4,5,5-tetramethyl-[1,3,2]dioxaborolan-2-yl)-phenyl]-morpholin-4-yl-methanone in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples Example 57

(4-{8-[4-(1,1-Dioxido-thiomorpholin-4-ylmethyl)-3-methyl-phenyl]-quinoxalin-2-yl}-2-methyl-phenyl)-morpholin-4-yl-methanone

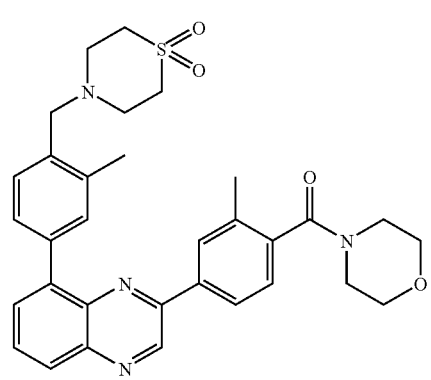

R$_t$=0.939 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 571 (M+1)⁺

Example 58

{4-[8-(3-Fluoro-4-morpholin-4-ylmethyl-phenyl)-quinoxalin-2-yl]-2-methyl-phenyl}-morpholin-4-yl-methanone

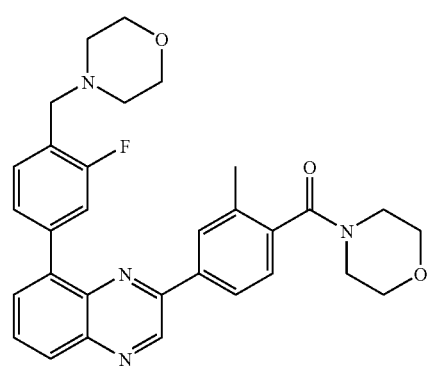

R$_t$=0.844 min (Acquity HPLC BEH C18, 2.1×50 mm, 1.7 micron, detection 215 nM, 0.1 min 2% CH₃CN in H₂O, 2% to 100% CH$_3$CN in H$_2$O in 1.5 min, 0.4 min 100% CH$_3$CN+ 0.1% TFA, flow rate 1.0 ml/min); MS: 527 (M+1)$^+$ Example 59

{4-[8-(3,5-Difluoro-4-morpholin-4-ylmethyl-phenyl)-quinoxalin-2-yl]-2-methyl-phenyl}-morpholin-4-yl-methanone

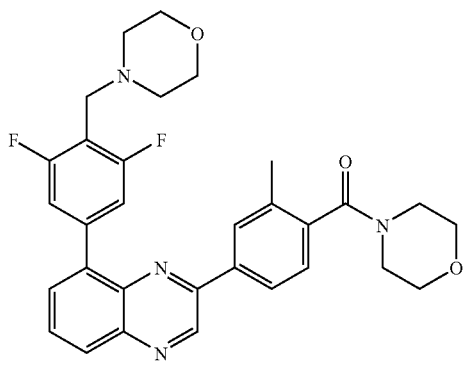

R$_t$=0.844 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 545 (M+1)$^+$ Example 60

{2-Methyl-4-[8-(3-methyl-4-morpholin-4-ylmethyl-phenyl)-quinoxalin-2-yl]-phenyl}-morpholin-4-yl-methanone

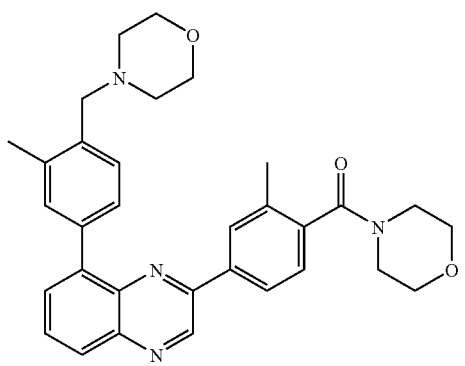

R$_t$=0.868 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 523 (M+1)$^+$ Example 61

(4-{8-[3-Chloro-4-(1,1-dioxido-thiomorpholin-4-ylmethyl)-phenyl]-quinoxalin-2-yl}-2-methyl-phenyl)-morpholin-4-yl-methanone

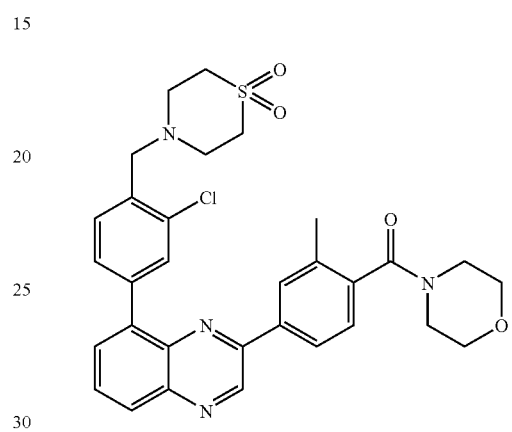

R$_t$=1.016 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 591 (M+1)$^+$ Example 62

(4-{8-[4-(1,1-Dioxido-thiomorpholin-4-ylmethyl)-3-fluoro-phenyl]-quinoxalin-2-yl}-2-methyl-phenyl)-morpholin-4-yl-methanone

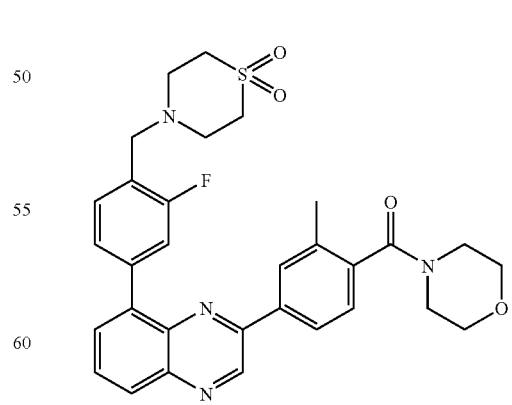

R$_t$=0.924 min (Acquity HPLC BEH C18, 2.1×50 mm, 1.7 micron, detection 215 nM, 0.1 min 2% CH$_3$CN in H$_2$O, 2% to 100% CH₃CN in H₂O in 1.5 min, 0.4 min 100% CH₃CN+ 0.1% TFA, flow rate 1.0 ml/min); MS: 575 (M+1)⁺

Example 63

(4-{8-[4-(1,1-Dioxido-thiomorpholin-4-ylmethyl)-phenyl]-quinoxalin-2-yl}-2-methyl-phenyl)-morpholin-4-yl-methanone

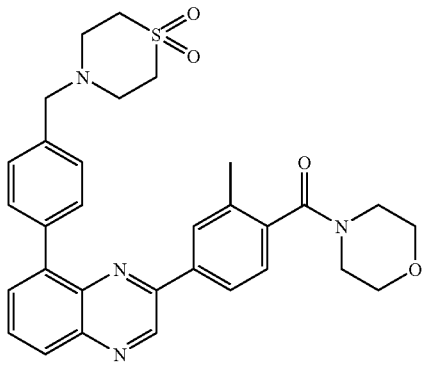

R$_t$=0.869 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 557 (M+1)⁺

Example 64

(4-{8-[4-(1,1-Dioxido-thiomorpholin-4-ylmethyl)-3,5-difluoro-phenyl]-quinoxalin-2-yl}-2-methyl-phenyl)-morpholin-4-yl-methanone

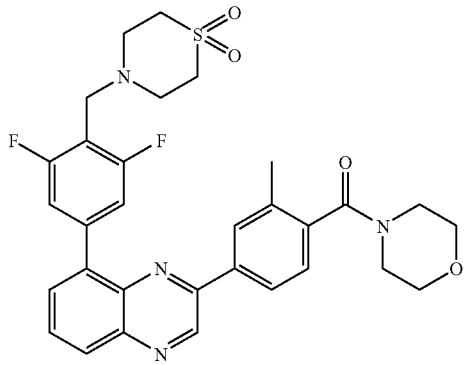

R$_t$=0.995 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 593 (M+1)⁺

Using the same synthetic methods as described in Example 1, but utilizing [4-(8-Bromo-quinoxalin-2-yl)-2-methyl-phenyl]-pyrrolidin-1-yl-methanone [prepared analogously to step 1.5 but utilizing [2-Methyl-4-(4,4,5,5-tetramethyl-[1,3,2]dioxaborolan-2-yl)-phenyl]-pyrrolidin-1-yl-methanone in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples Example 65

{4-[8-(3-Fluoro-4-morpholin-4-ylmethyl-phenyl)-quinoxalin-2-yl]-2-methyl-phenyl}-pyrrolidin-1-yl-methanone

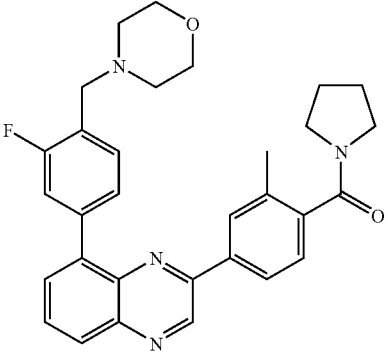

R$_t$=0.897 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 511 (M+1)⁺

Example 66

{4-[8-(3,5-Difluoro-4-morpholin-4-ylmethyl-phenyl)-quinoxalin-2-yl]-2-methyl-phenyl}-pyrrolidin-1-yl-methanone

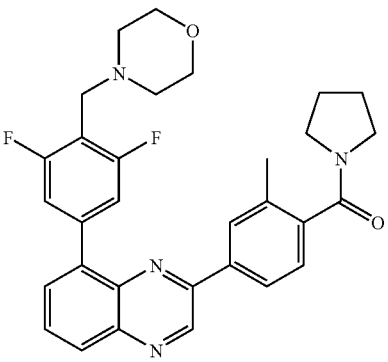

R$_t$=0.897 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 529 (M+1)⁺

Example 67

(4-{8-[3-Chloro-4-(1,1-dioxido-thiomorpholin-4-ylmethyl)-phenyl]-quinoxalin-2-yl}-2-methyl-phenyl)-pyrrolidin-1-yl-methanone

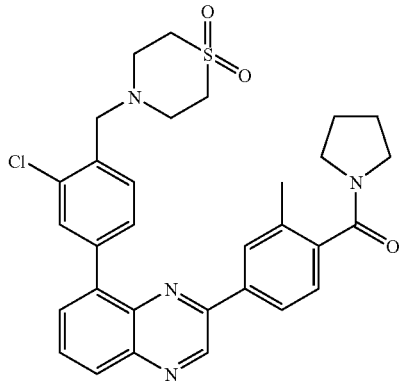

$R_t$=1.072 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 575 (M+1)⁺

Example 68

(2-Methyl-4-{3-[3-methyl-4-(pyrrolidine-1-carbonyl)-phenyl]-quinoxalin-5-yl}-phenyl)-pyrrolidin-1-yl-methanone

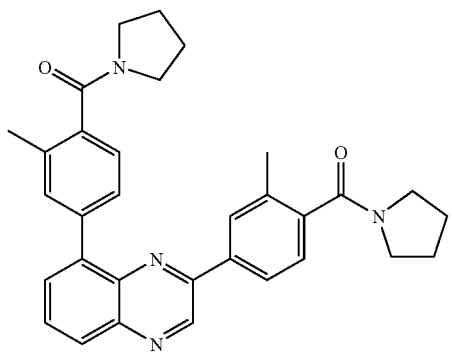

$R_t$=1.160 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 505 (M+1)⁺

Using the same synthetic methods as described in Example 1, but utilizing 8-Bromo-2-(3-methyl-4-morpholin-4-ylmethyl-phenyl)-quinoxaline [prepared analogously to step 1.5 but utilizing 4-[2-Methyl-4-(4,4,5,5-tetramethyl-[1,3,2]dioxaborolan-2-yl)-benzyl]-morpholine in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples Example 69

1-(1,1-Dioxido-thiomorpholin-4-yl)-2-{2-fluoro-4-[3-(3-methyl-4-morpholin-4-ylmethyl-phenyl)-quinoxalin-5-yl]-phenyl}-ethanone

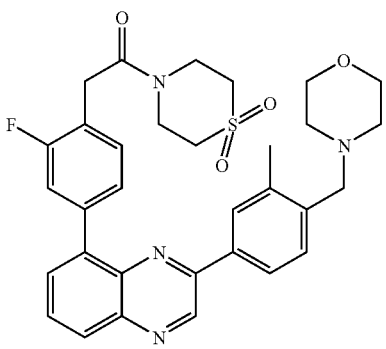

$R_t$=0.885 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 589 (M+1)⁺

Example 70

8-[4-(1,1-Dioxido-thiomorpholin-4-ylmethyl)-3-methyl-phenyl]-2-(3-methyl-4-morpholin-4-ylmethyl-phenyl)-quinoxaline

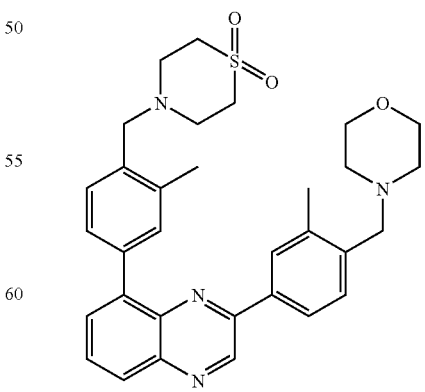

$R_t$=0.827 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 557 (M+1)⁺

Example 71

8-(3,5-Difluoro-4-morpholin-4-ylmethyl-phenyl)-2-(3-methyl-4-morpholin-4-ylmethyl-phenyl)-quinoxaline

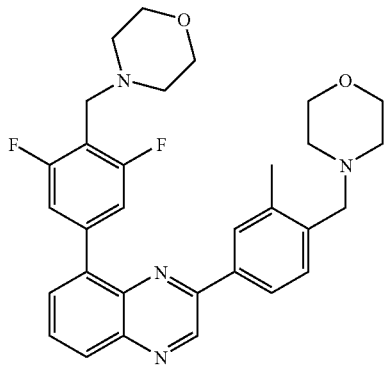

R$_t$=0.720 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 531 (M+1)⁺

Using the same synthetic methods as described in Example 1, but utilizing 8-Bromo-2-(4-imidazol-1-ylmethyl-3-methyl-phenyl)-quinoxaline [prepared analogously to step 1.5 but utilizing 142-Methyl-4-(4,4,5,5-tetramethyl-[1,3,2]dioxaborolan-2-yl)-benzyl]-1H-imidazole in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Example

Example 72

1-(1,1-Dioxido-thiomorpholin-4-yl)-2-{2-fluoro-4-[3-(4-imidazol-1-ylmethyl-3-methyl-phenyl)-quinoxalin-5-yl]-phenyl}-ethanone

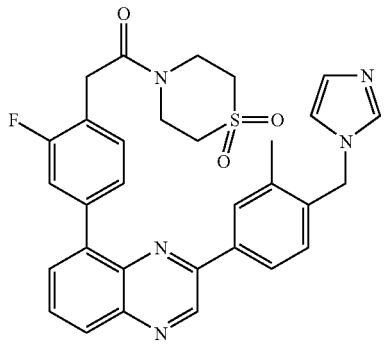

R$_t$=0.905 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 570 (M+1)⁺

Using the same synthetic methods as described in Example 1, but utilizing 8-Bromo-2-[4-(3-morpholin-4-yl-propoxy)-phenyl]-quinoxaline [prepared analogously to step 1.5 but utilizing 4-{3-[4-(4,4,5,5-Tetramethyl-[1,3,2]dioxaborolan-2-yl)-phenoxy]-propyl}-morpholine in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples

Example 73

(1,1-Dioxido-thiomorpholin-4-yl)-(2-fluoro-4-{3-[4-(3-morpholin-4-yl-propoxy)-phenyl]-quinoxalin-5-yl}-phenyl)-methanone

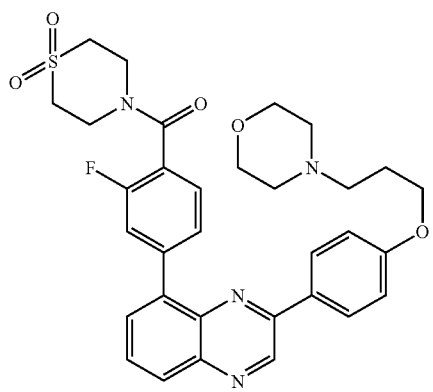

R$_t$=0.897 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 605 (M+1)⁺

Example 74

1-Morpholin-4-yl-2-(4-{3-[4-(3-morpholin-4-yl-propoxy)-phenyl]-quinoxalin-5-yl}-phenyl)-ethanone

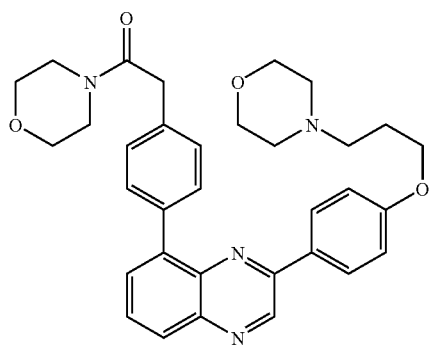

R$_t$=0.929 min (Acquity HPLC BEH C18, 2.1×50 mm, 1.7 micron, detection 215 nM, 0.1 min 2% CH₃CN in H₂O, 2% to 100% CH$_3$CN in H$_2$O in 1.5 min, 0.4 min 100% CH$_3$CN+ 0.1% TFA, flow rate 1.0 ml/min); MS: 553 (M+1)$^+$ Example 75

(2-Fluoro-4-{3-[4-(3-morpholin-4-yl-propoxy)-phenyl]-quinoxalin-5-yl}-phenyl)-morpholin-4-yl-methanone

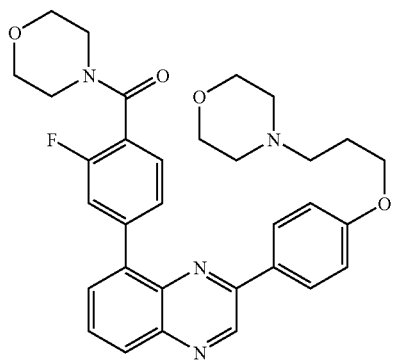

R$_t$=0.929 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 557 (M+1)$^+$ Using the same synthetic methods as described in Example 1, but utilizing 8-Bromo-2-[3-methyl-4-(3-morpholin-4-yl-propoxy)-phenyl]-quinoxaline [prepared analogously to step 1.5 but utilizing 4-{3-[2-Methyl-4-(4,4,5,5-tetramethyl-[1,3,2]dioxaborolan-2-yl)-phenoxy]-propyl}-morpholine in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples Example 76

2-(2-Fluoro-4-{3-[3-methyl-4-(3-morpholin-4-yl-propoxy)-phenyl]-quinoxalin-5-yl}-phenyl)-1-morpholin-4-yl-ethanone

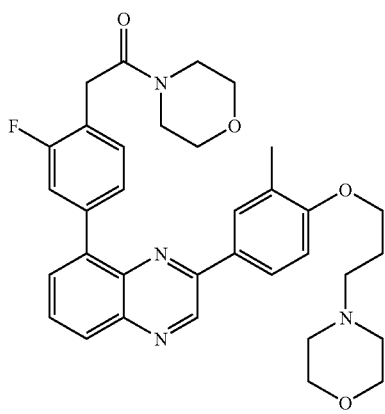

R$_t$=0.982 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 585 (M+1)$^+$ Example 77

4-[8-(4-Ethanesulfonyl-phenyl)-quinoxalin-2-yl]-2-methoxy-phenol

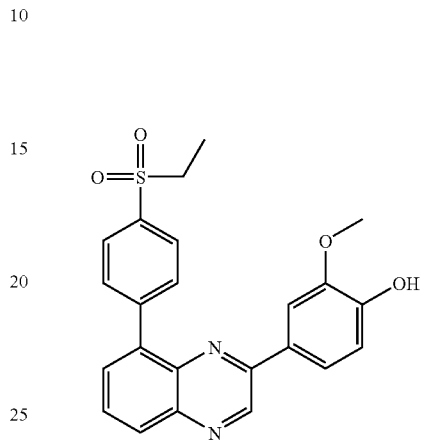

R$_t$=1.079 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 421 (M+1)$^+$.

Example 78

2-{4-[7-Fluoro-3-(3,4,5-trimethoxy-phenyl)-quinoxalin-5-yl]-phenyl}-1-morpholin-4-yl-ethanone

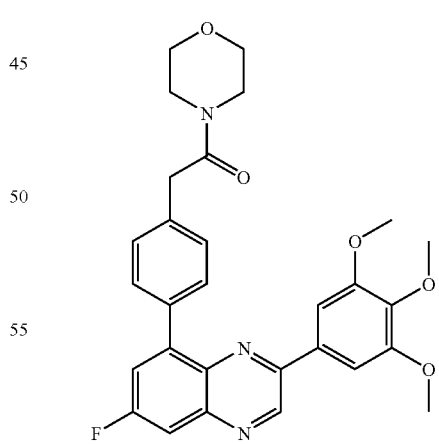

R$_t$=1.164 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 518 (M+1)$^+$.

The starting materials can be prepared as follows:

a) 8-Bromo-6-fluoro-2-(3,4,5-trimethoxy-phenyl)-quinoxaline

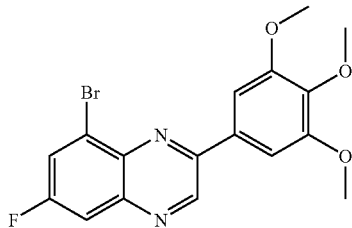

A round bottom flask is charged with 1.03 g (5 mmol) 3-Bromo-5-fluoro-benzene-1,2-diamine and solved into 30 ml EtOH. 1.15 g (5.02 mmol) 3,4,5-trimethylphenylglyoxal monohydrate is then added and the mixture is heated to 80° C. for 1 h. After cooling to 0° C., the suspension is filtered and the residue is purified by chromatography (silicagel, hexane: EtOAc 2:1) to afford the title compound as a yellow solid.

Example 79

{4-[7-Methyl-3-(3,4,5-trimethoxy-phenyl)-quinoxalin-5-yl]-phenyl}-morpholin-4-yl-methanone

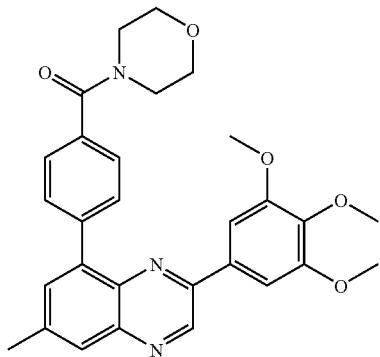

$R_t$=1.198 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+ 0.1% TFA, flow rate 1.0 ml/min); MS: 500 $(M+1)^+$.

The starting materials can be prepared as follows:

a) 8-Bromo-6-methyl-2-(3,4,5-trimethoxy-phenyl)-quinoxaline

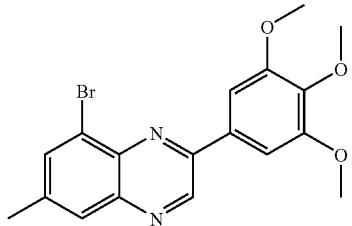

A round bottom flask is charged with 1 g (4.97 mmol) 3-Bromo-5-methyl-benzene-1,2-diamine and solved into 27 ml EtOH. 1.23 g (4.97 mmol) 3,4,5-trimethylphenylglyoxal monohydrate is then added and the mixture is heated to 60° C. for 1 h. After cooling to 0° C., the title compound is collected by filtration and used in the next step without further purification.

Example 80

(4-Ethyl-piperazin-1-yl)-(2-methyl-4-{8-[3-methyl-4-(1-methyl-1-morpholin-4-yl-ethyl)-phenyl]-quinoxalin-2-yl}-phenyl)-methanone

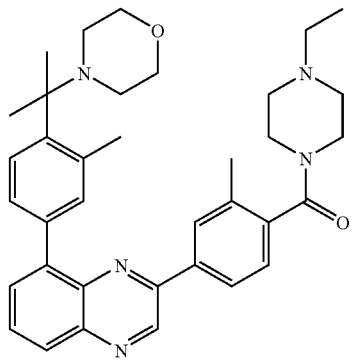

A microwave tube is charged with of [4-(8-Bromo-quinoxalin-2-yl)-2-methyl-phenyl]-(4-ethyl-piperazin-1-yl)-methanone (step 80.1, 49 mg, 0.112 mmol), 4-{1-Methyl-1-[2-methyl-4-(4,4,5,5-tetramethyl-[1,3,2]dioxaborolan-2-yl)-phenyl]-ethyl}-morpholine (40.4 mg, ca. 0.117 mmol), S-Phos (4.25 mg, 0.01 mmol), $K_3PO_4$ (72.5 mg, 0.33 mmol) and $Pd(OAc)_2$ (0.75 mg, 0.0033 mmol). After several cycles of vacuum/purge with argon, 3 ml of a mixture consisting of 28 μl deionized water in 12 ml 1,2-dimethoxy-ethane, are added. The reaction mixture is then heated to 105° C. for 5 h 30. After cooling, the reaction mixture is diluted with $CH_2Cl_2$, poured onto a saturated solution of $Na_2CO_3$ and extracted 3× with $CH_2Cl_2$. The combined organic layers are washed with water, brine, dried over $Na_2SO_4$, filtered and the filtrate is concentrated in vacuo. The residue is purified by chromatography (silicagel, $CH_2Cl_2/CH_2Cl_2$:EtOH:NH3 90:9:1 from 1:0=>0:1) to afford the title compound as a pale yellow foam, $R_t$=1.777 min (Acquity HPLC BEH C18, 2.1× 50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+0.1% TFA, flow rate 1.0 ml/min); MS: 578 $(M+1)^+$.

The starting materials can be prepared as follows:

Step 80.1

[4-(8-Bromo-quinoxalin-2-yl)-2-methyl-phenyl]-(4-ethyl-piperazin-1-yl)-methanone

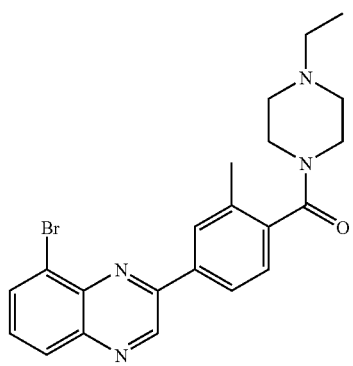

A microwave tube is charged with 8-Bromo-2-chloro-quinoxaline (Step 1.4, 298 mg, 1.226 mmol), (4-Ethyl-piperazin-1-yl)-[2-methyl-4-(4,4,5,5-tetramethyl-[1,3,2]dioxaborolan-2-yl)-phenyl]-methanone (439 mg, 1.226 mmol), $K_3PO_4$ (532 mg, 2.450 mmol) and $Pd(PPh_3)_4$ (43.8 mg, 0.0368 mmol). After several cycles of vacuum/purge with argon, 5 ml of dry DMA are added. The reaction mixture is then heated to 105° C. for 4 h. After cooling, the suspension is poured onto 70 ml de-ionized water and filtered. The cake is re-taken in EtOAc, washed with saturated brine and dried over $Na_2SO_4$. After filtration, the mixture is concentrated in vacuo. The residue is purified by chromatography (silicagel, $CH_2Cl_2/CH_2Cl_2$:EtOH:NH3 90:9:1 from 1:0=>0:1) to afford the title compound as a pale brown foam, $R_t$=0.833 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+0.1% TFA, flow rate 1.0 ml/min); MS: 439 (M+1, $^{79}Br$)$^+$.

Using the same synthetic methods as described in Example 80, reaction of [4-(8-Bromo-quinoxalin-2-yl)-2-methyl-phenyl]-(4-ethyl-piperazin-1-yl)-methanone and the appropriate boronic acid or ester derivative leads to the following Examples:

Example 81

[4-(8-{4-[1-(1,1-Dioxido-thiomorpholin-4-yl)-1-methyl-ethyl]-3-methyl-phenyl}-quinoxalin-2-yl)-2-methyl-phenyl]-(4-ethyl-piperazin-1-yl)-methanone

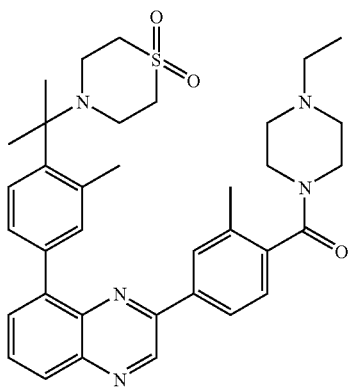

$R_t$=1.040 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+ 0.1% TFA, flow rate 1.0 ml/min); MS: 626 (M+1)$^+$.

Example 82

{4-[8-(3,5-Difluoro-4-morpholin-4-ylmethyl-phenyl)-quinoxalin-2-yl]-2-methyl-phenyl}-(4-ethyl-piperazin-1-yl)-methanone

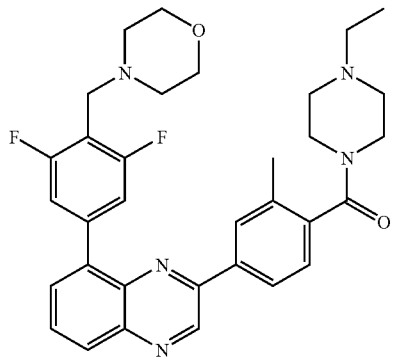

$R_t$=0.716 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+ 0.1% TFA, flow rate 1.0 ml/min); MS: 572 (M+1)$^+$.

Using the same synthetic methods as described in Example 1, but utilizing 8-Bromo-2-[3-methoxy-4-(3-morpholin-4-yl-propoxy)-phenyl]-quinoxaline [prepared analogously to step 1.5 but utilizing 4-{3-[2-Methoxy-4-(4,4,5,5-tetramethyl-[1,3,2]dioxaborolan-2-yl)-phenoxy]-propyl}-morpholine in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples

Example 83

2-(4-{3-[3-Methoxy-4-(3-morpholin-4-yl-propoxy)-phenyl]-quinoxalin-5-yl}-phenyl)-1-morpholin-4-yl-ethanone

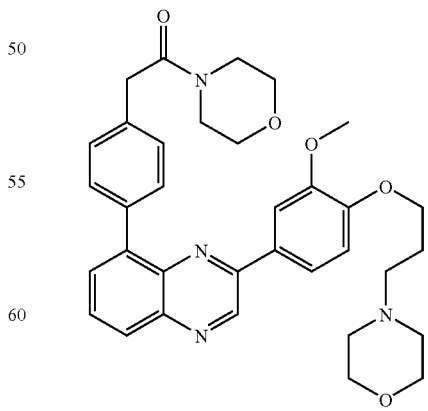

$R_t$=0.938 min (Acquity HPLC BEH C18, 2.1×50 mm, 1.7 micron, detection 215 nM, 0.1 min 2% $CH_3CN$ in $H_2O$, 2% to 100% CH$_3$CN in H$_2$O in 1.5 min, 0.4 min 100% CH$_3$CN+ 0.1% TFA, flow rate 1.0 ml/min); MS: 583 (M+1)$^+$ Example 84

8-(3,5-Difluoro-4-morpholin-4-ylmethyl-phenyl)-2-[3-methoxy-4-(3-morpholin-4-yl-propoxy)-phenyl]-quinoxaline

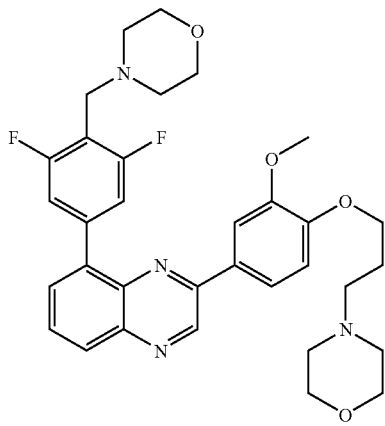

R$_t$=0.776 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 591 (M+1)$^+$ Example 85

8-[4-(1,1-Dioxido-thiomorpholin-4-ylmethyl)-3-fluoro-phenyl]-2-[3-methoxy-4-(3-morpholin-4-yl-propoxy)-phenyl]-quinoxaline

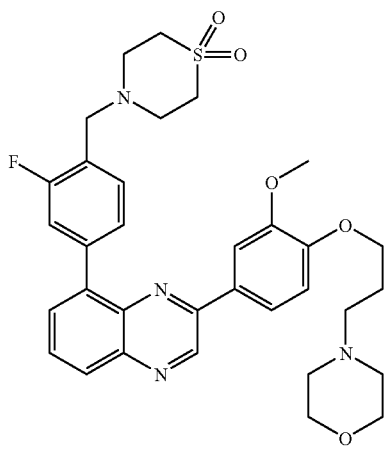

R$_t$=0.882 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 621 (M+1)$^+$ Example 86

8-[4-(1,1-Dioxido-thiomorpholin-4-ylmethyl)-3,5-difluoro-phenyl]-2-[3-methoxy-4-(3-morpholin-4-yl-propoxy)-phenyl]-quinoxaline

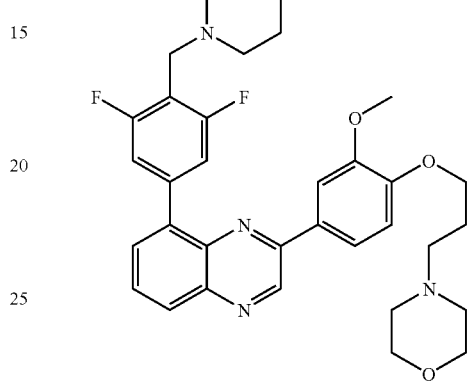

R$_t$=0.940 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 639 (M+1)$^+$ Example 87

8-(3,5-Difluoro-4-morpholin-4-ylmethyl-phenyl)-2-[4-(4-methyl-piperazin-1-yl)-phenyl]-quinoxaline

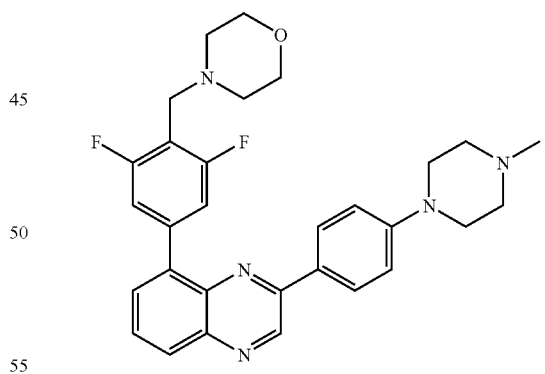

A microwave tube is charged with 8-Bromo-2-[4-(4-methyl-piperazin-1-yl)-phenyl]-quinoxaline (2.6 g, 6.783 mmol), 4-[2,6-Difluoro-4-(4,4,5,5-tetramethyl-[1,3,2]dioxaborolan-2-yl)-benzyl]-morpholine (Step 87.1, 2.68 g, 7.12 mmol), S-Phos (258 mg, 0.611 mmol), K$_3$PO$_4$ (4.41 g, 20.4 mmol) and Pd(OAc)$_2$ (45.68 mg, 0.203 mmol). After several cycles of vacuum/purge with argon, a mixture of 370 μl deionized water in 30 ml 1,2-dimethoxy-ethane is added. The reaction mixture is then heated to 105° C. for 12 h. After cooling, the reaction mixture is diluted with CH$_2$Cl$_2$, poured onto a saturated solution of NaHCO$_3$ and extracted 3× with CH$_2$Cl$_2$.

111

The combined organic layers are washed with water, brine, dried over Na$_2$SO$_4$, filtered and the filtrate is concentrated in vacuo. The residue is purified by chromatography (silicagel, CH$_2$Cl$_2$/CH$_2$Cl$_2$:EtOH:NH3 90:9:1 4:6) to afford the title compound as yellow solid, R$_t$=0.742 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 516 (M+1)$^+$.

The starting materials can be prepared as follows:

Step 87.1

8-Bromo-2-[4-(4-methyl-piperazin-1-yl)-phenyl]-quinoxaline

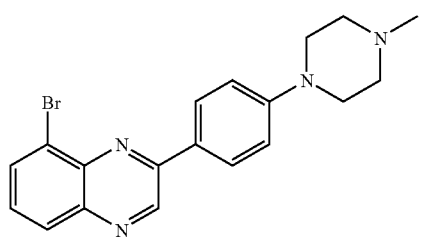

A microwave tube is charged with 8-Bromo-2-chloro-quinoxaline (Step 1.4, 2.5 g, 10.267 mmol), 1-Methyl-4-[4-(4,4,5,5-tetramethyl-[1,3,2]dioxaborolan-2-yl)-phenyl]-piperazine (2.88 g, 9.24 mmol), K$_3$PO$_4$ (6.67 g, 30.8 mmol) and PdCl$_2$(PPh$_3$)$_2$ (221 mg, 0.308 mmol). After several cycles of vacuum/purge with argon, a mixture of 21 ml of DMA and 560 µl deionized water is added. The reaction mixture is then heated to 105° C. for 4 h. After cooling, the suspension is poured onto de-ionized water and diluted with EtOAc. The phases are separated and the aqueous phase re-extracted twice with EtOAc. The combined organic phases are washed with saturated brine and dried over Na$_2$SO$_4$. After filtration, the mixture is concentrated in vacuo. The residue is purified by chromatography (silicagel, CH$_2$Cl$_2$:EtOH:NH3 95:4.5:0.5 from 1:0=>0:1) to afford the title compound as a yellow orange solid, R$_t$=0.930 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 383 (M+1, $^{79}$Br)$^+$.

Using the same synthetic methods as described in Example 87, reaction of 8-Bromo-2-[4-(4-methyl-piperazin-1-yl)-phenyl]-quinoxaline and the appropriate boronic ester derivative leads to the following Examples:

112

Example 88

2-(2-Fluoro-4-{3-[4-(4-methyl-piperazin-1-yl)-phenyl]-quinoxalin-5-yl}-phenyl)-1-morpholin-4-yl-ethanone

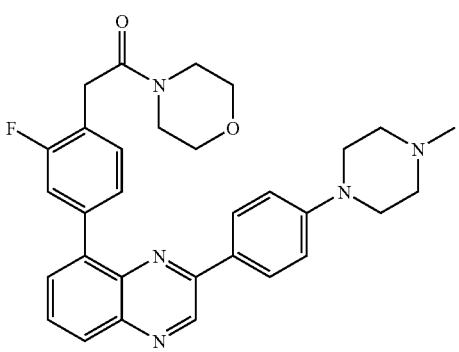

R$_t$=0.934 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 526 (M+1)$^+$ Example 89

(2,6-Difluoro-4-{3-[4-(4-methyl-piperazin-1-yl)-phenyl]-quinoxalin-5-yl}-phenyl)-morpholin-4-yl-methanone

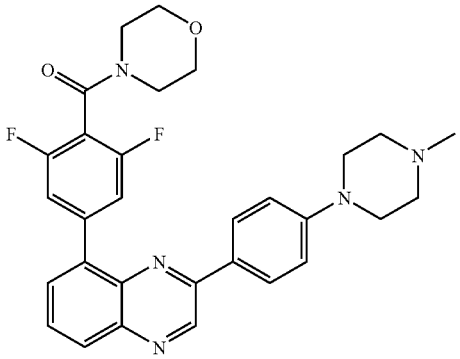

R$_t$=0.939 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 530 (M+1)$^+$

Example 90

8-[4-(1,1-Dioxido-thiomorpholin-4-ylmethyl)-3,5-difluoro-phenyl]-2-[4-(4-methyl-piperazin-1-yl)-phenyl]-quinoxaline

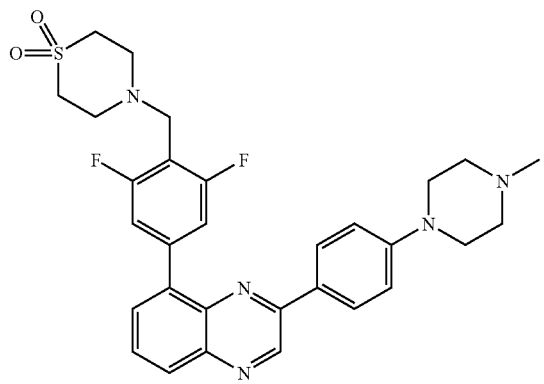

$R_t$=0.913 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 564 (M+1)$^+$

Example 91

8-[4-(1,1-Dioxido-thiomorpholin-4-ylmethyl)-phenyl]-2-[4-(4-methyl-piperazin-1-yl)-phenyl]-quinoxaline

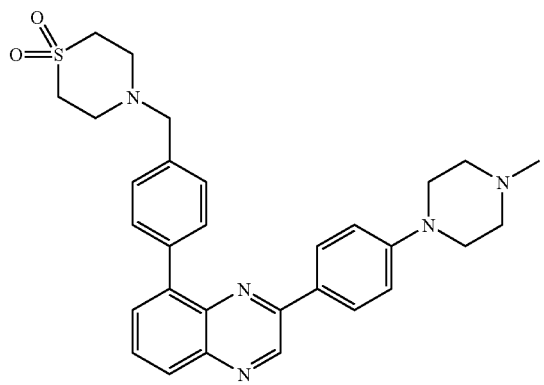

$R_t$=0.794 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 528 (M+1)$^+$ Using the same synthetic methods as described in Example 1, but utilizing 8-Bromo-2-[4-(4-ethyl-piperazin-1-ylmethyl)-3-methyl-phenyl]-quinoxaline [prepared analogously to step 1.5 but utilizing 1-Ethyl-4-[2-methyl-4-(4,4,5,5-tetramethyl-[1,3,2]dioxaborolan-2-yl)-benzyl]-piperazine in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples

Example 92

8-(3,5-Difluoro-4-morpholin-4-ylmethyl-phenyl)-2-[4-(4-ethyl-piperazin-1-ylmethyl)-3-methyl-phenyl]-quinoxaline

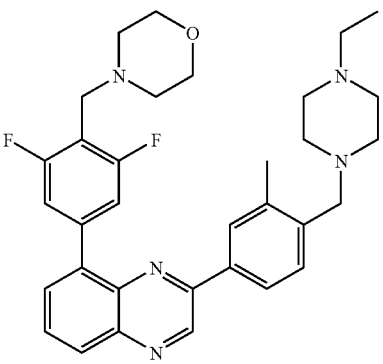

$R_t$=0.743 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 558 (M+1)$^+$

Example 93

2-[4-(4-Ethyl-piperazin-1-ylmethyl)-3-methyl-phenyl]-8-(3-fluoro-4-morpholin-4-ylmethyl-phenyl)-quinoxaline

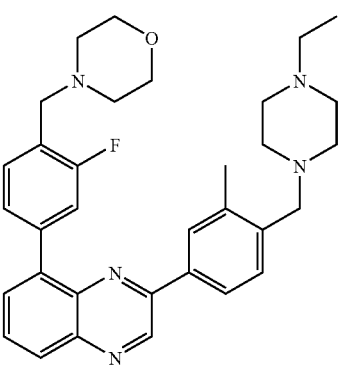

$R_t$=0.741 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 540 (M+1)$^+$ Using the same synthetic methods as described in Example 1, but utilizing 4-(8-Bromo-quinoxalin-2-yl)-N-(2-dimethylamino-ethyl)-2,N-dimethyl-benzamide [prepared analogously to step 1.5 but utilizing N-(2-Dimethylamino-ethyl)-2,N-dimethyl-4-(4,4,5,5-tetramethyl-[1,3,2]dioxaborolan-2-yl)-benzamide in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples

Example 94

4-[8-(3,5-Difluoro-4-morpholin-4-ylmethyl-phenyl)-quinoxalin-2-yl]-N-(2-dimethylamino-ethyl)-2,N-dimethyl-benzamide

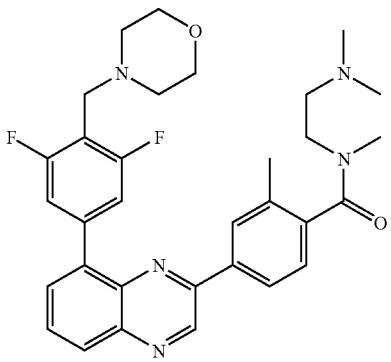

$R_t$=0.750 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 560 (M+1)$^+$

Example 95

N-(2-Dimethylamino-ethyl)-4-{8-[4-(1,1-dioxido-thiomorpholin-4-ylmethyl)-3,5-difluoro-phenyl]-quinoxalin-2-yl}-2,N-dimethyl-benzamide

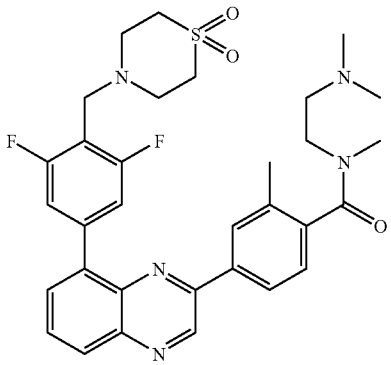

$R_t$=0.893 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 608 (M+1)$^+$ Using the same synthetic methods as described in Example 1, but utilizing 8-Bromo-2-(1-piperidin-4-yl-1H-pyrazol-4-yl)-quinoxaline [prepared in step 94.2] in lieu of 8-Bromo-2-(3,4,5-trimethoxy-phenyl)-quinoxaline and the appropriate boronic acid or ester derivative leads to the following Examples

Example 96

8-[4-(1,1-Dioxido-thiomorpholin-4-ylmethyl)-3,5-difluoro-phenyl]-2-(1-piperidin-4-yl-1H-pyrazol-4-yl)-quinoxaline

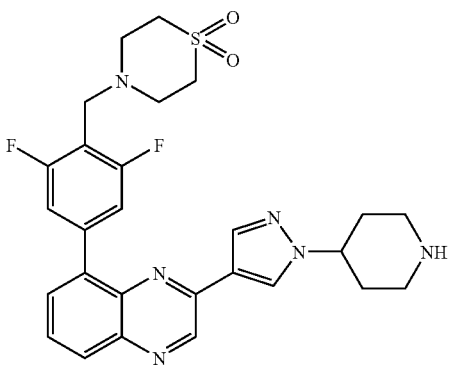

$R_t$=0.819 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 539 (M+1)$^+$ The starting materials can be prepared as follows:

Step 96.1

4-[4-(8-Bromo-quinoxalin-2-yl)-pyrazol-1-yl]-piperidine-1-carboxylic acid tert-butyl ester

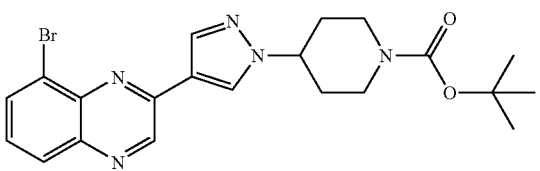

A microwave tube is charged with 8-Bromo-2-chloro-quinoxaline (Step 1.4, 1 g, 4.11 mmol), 4-[4-(4,4,5,5-Tetramethyl-[1,3,2]dioxaborolan-2-yl)-pyrazol-1-yl]-piperidine-1-carboxylic acid tert-butyl ester (1.74 g, 3.70 mmol), K$_3$PO$_4$ (2.67 g, 12.3 mmol) and of PdCl$_2$(PPh$_3$)$_2$ (88.2 mg, 0.123 mmol). After several cycles of vacuum/purge with argon, a mixture of 5 ml of DMA and 220 µl deionized water is added. The reaction mixture is then heated to 80° C. for 3 h. After cooling, the suspension is poured onto de-ionized water and diluted with EtOAc. The phases are separated and the aqueous phase re-extracted twice with EtOAc. The combined organic phases are washed with saturated brine and dried over Na$_2$SO$_4$. After filtration, the mixture is concentrated in vacuo. The residue is purified by chromatography on a 80 g silica gel column on a Combiflash Companion™ (Isco Inc.) apparatus (gradient hexanes:EtOAc from 1:0=>0:1) to afford the title compound as a yellow foam, R$_t$=1.350 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 458 (M+1, $^{79}$Br)$^+$.

Step 96.2

8-Bromo-2-(1-piperidin-4-yl-1H-pyrazol-4-yl)-quinoxaline

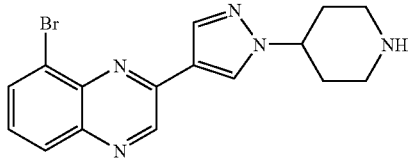

A 1.2 M solution of HCl in EtOH (60 ml, 72 mmol) is added to 4-[4-(8-Bromo-quinoxalin-2-yl)-pyrazol-1-yl]-piperidine-1-carboxylic acid tert-butyl ester (Step 94.1, 1.98 g, 4.32 mmol) and the reaction mixture is heated at 50° C. for 12 h. After cooling, the yellow suspension is concentrated under vacuo and the residue is diluted with CH$_2$Cl$_2$, poured onto a saturated solution of NaHCO$_3$ and extracted 3× with CH$_2$Cl$_2$. The combined organic layers are washed with water, brine, dried over Na$_2$SO$_4$, filtered and the filtrate is concentrated in vacuo. The residue is used without further purification in the next step, and afford the title compound as pale orange solid, R$_t$=0.802 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 358 (M+1, $^{79}$Br)$^+$ Example 97

{2,6-Difluoro-4-[3-(1-piperidin-4-yl-1H-pyrazol-4-yl)-quinoxalin-5-yl]-phenyl}-morpholin-4-yl-methanone

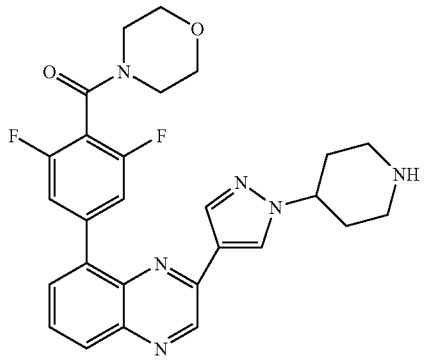

R$_t$=0.848 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 505 (M+1)$^+$ Example 98

8-(3,5-Difluoro-4-morpholin-4-ylmethyl-phenyl)-2-(1-piperidin-4-yl-1H-pyrazol-4-yl)-quinoxaline

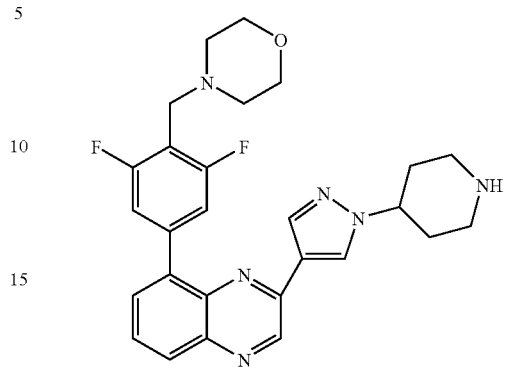

R$_t$=0.682 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 491 (M+1)$^+$ Example 99

8-(3-Fluoro-4-methanesulfonyl-phenyl)-2-(1-piperidin-4-yl-1H-pyrazol-4-yl)-quinoxaline

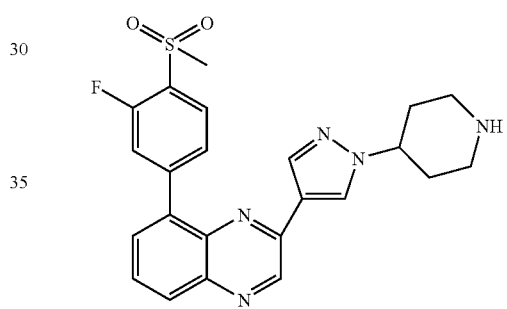

R$_t$=0.841 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 452 (M+1)$^+$ Example 100

{2-Methyl-4-[3-(1-piperidin-4-yl-1H-pyrazol-4-yl)-quinoxalin-5-yl]-phenyl}-morpholin-4-yl-methanone

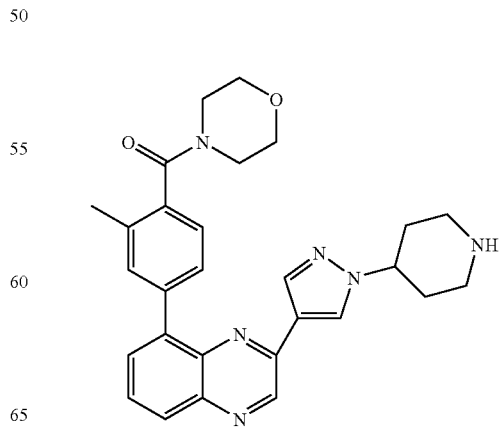

$R_t$=0.883 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+ 0.1% TFA, flow rate 1.0 ml/min); MS: 483 (M+1)$^+$ Using the same synthetic methods as described in Example 1, but utilizing 4-(8-Bromo-quinoxalin-2-yl)-2-methyl-phenyl]-(4-dimethylamino-piperidin-1-yl)-methanone [prepared analogously to step 1.5 but utilizing (4-Dimethylamino-piperidin-1-yl)-[2-methyl-4-(4,4,5,5-tetramethyl-[1,3,2]dioxaborolan-2-yl)-phenyl]-methanone in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples Example 101

{4-[8-(3,5-Difluoro-4-morpholin-4-ylmethyl-phenyl)-quinoxalin-2-yl]-2-methyl-phenyl}-(4-dimethylamino-piperidin-1-yl)-methanone

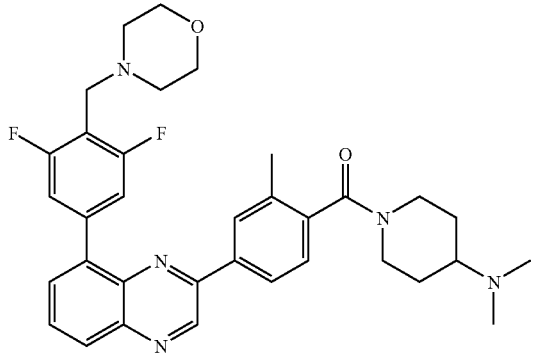

$R_t$=0.729 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+ 0.1% TFA, flow rate 1.0 ml/min); MS: 586 (M+1)$^+$ Example 102

(4-Dimethylamino-piperidin-1-yl)-(4-{8-[4-(1,1-dioxido-thiomorpholin-4-ylmethyl)-3,5-difluoro-phenyl]-quinoxalin-2-yl}-2-methyl-phenyl)-methanone

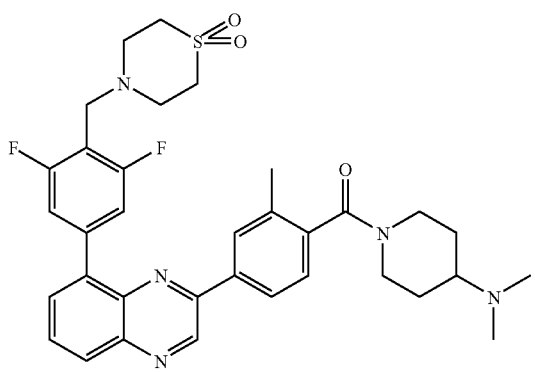

$R_t$=0.881 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+ 0.1% TFA, flow rate 1.0 ml/min); MS: 634 (M+1)$^+$ Using the same synthetic methods as described in Example 1, but utilizing 8-Bromo-2-[4-(4-ethyl-piperazin-1-yl)-3-methyl-phenyl]-quinoxaline [prepared analogously to step 1.5 but utilizing 1-Ethyl-4-[2-methyl-4-(4,4,5,5-tetramethyl-[1,3,2]dioxaborolan-2-yl)-phenyl]-piperazine in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples Example 103

8-(3,5-Difluoro-4-morpholin-4-ylmethyl-phenyl)-2-[4-(4-ethyl-piperazin-1-yl)-3-methyl-phenyl]-quinoxaline

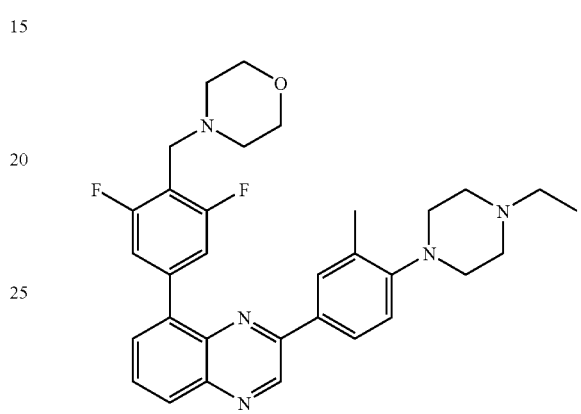

$R_t$=0.804 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+ 0.1% TFA, flow rate 1.0 ml/min); MS: 544 (M+1)$^+$ Using the same synthetic methods as described in Example 1, but utilizing 8-Bromo-2-[3-methoxy-4-(4-methyl-piperazin-1-yl)-phenyl]-quinoxaline [prepared analogously to step 1.5 but utilizing 1-[2-Methoxy-4-(4,4,5,5-tetramethyl-[1,3,2]dioxaborolan-2-yl)-phenyl]-4-methyl-piperazine in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples Example 104

8-(3,5-Difluoro-4-morpholin-4-ylmethyl-phenyl)-2-[3-methoxy-4-(4-methyl-piperazin-1-yl)-phenyl]-quinoxaline

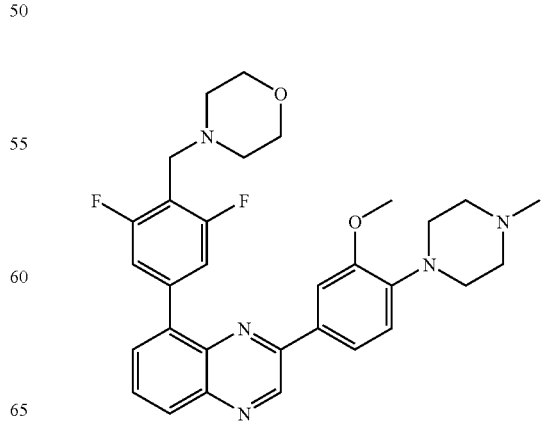

$R_t$=0.750 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 546 (M+1)$^+$ Example 105

(4-{3-[3-Methoxy-4-(4-methyl-piperazin-1-yl)-phenyl]-quinoxalin-5-yl}-2-methyl-phenyl)-morpholin-4-yl-methanone

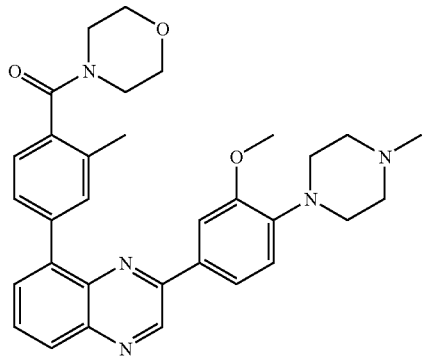

$R_t$=0.912 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 538 (M+1)$^+$ Using the same synthetic methods as described in Example 1, but utilizing 8-Bromo-2-(2-methoxy-pyridin-4-yl)-quinoxaline [prepared analogously to step 1.5 but utilizing 2-methoxy-pyridine 4-boronic acid in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples Example 106

8-[4-(1,1-Dioxido-thiomorpholin-4-ylmethyl)-3,5-difluoro-phenyl]-2-(2-methoxy-pyridin-4-yl)-quinoxaline

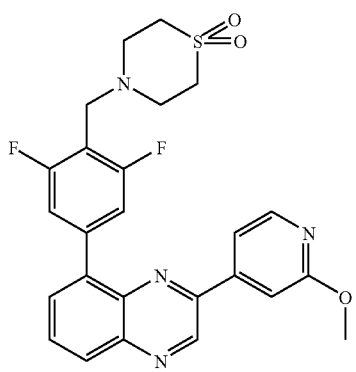

$R_t$=1.058 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 497 (M+1)$^+$ Using the same synthetic methods as described in Example 1, but utilizing 8-Bromo-2-[6-(4-methyl-piperazin-1-yl)-pyridin-3-yl]-quinoxaline [prepared analogously to step 1.5 but utilizing 1-Methyl-445-(4,4,5,5-tetramethyl-[1,3,2]dioxaborolan-2-yl)-pyridin-2-yl]-piperazine in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples Example 107

8-(3,5-Difluoro-4-morpholin-4-ylmethyl-phenyl)-2-[6-(4-methyl-piperazin-1-yl)-pyridin-3-yl]-quinoxaline

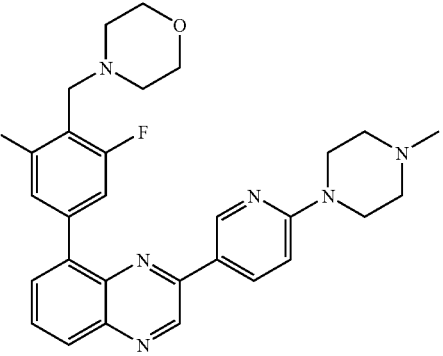

$R_t$=0.702 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 517 (M+1)$^+$ Example 108

8-[4-(1,1-Dioxido-thiomorpholin-4-ylmethyl)-3,5-difluoro-phenyl]-2-[6-(4-methyl-piperazin-1-yl)-pyridin-3-yl]-quinoxaline

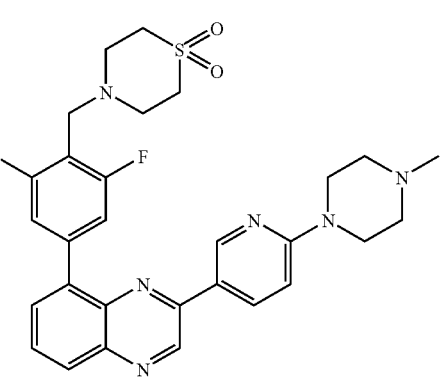

$R_t$=0.839 min (Acquity HPLC BEH C18, 2.1×50 mm, 1.7 micron, detection 215 nM, 0.1 min 2% CH$_3$CN in H$_2$O, 2% to 100% CH₃CN in H₂O in 1.5 min, 0.4 min 100% CH₃CN+ 0.1% TFA, flow rate 1.0 ml/min); MS: 565 (M+1)⁺

Example 109

8-[4-(1,1-Dioxido-thiomorpholin-4-ylmethyl)-phenyl]-2-[6-(4-methyl-piperazin-1-yl)-pyridin-3-yl]-quinoxaline

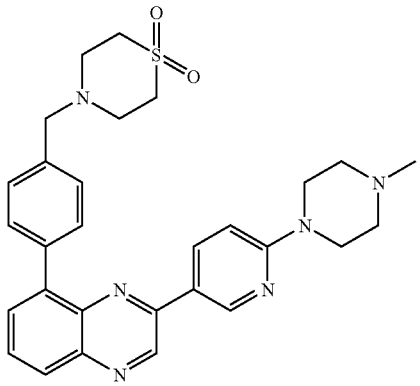

R$_t$=0.716 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 529 (M+1)⁺

Using the same synthetic methods as described in Example 1, but utilizing 5-(8-Bromo-quinoxalin-2-yl)-pyridine-2-carboxylic acid (2-dimethylamino-ethyl)-methyl-amide [prepared analogously to step 1.5 but utilizing 5-(4,4,5,5-Tetramethyl-[1,3,2]dioxaborolan-2-yl)-pyridine-2-carboxylic acid (2-dimethylamino-ethyl)-methyl-amide in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples

Example 110

5-[8-(3,5-Difluoro-4-morpholin-4-ylmethyl-phenyl)-quinoxalin-2-yl]-pyridine-2-carboxylic acid (2-dimethylamino-ethyl)-methyl-amide

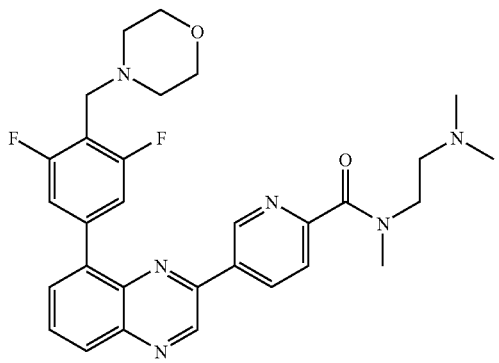

R$_t$=0.674 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 547 (M+1)⁺

Example 111

5-{8-[4-(1,1-Dioxido-thiomorpholin-4-ylmethyl)-3,5-difluoro-phenyl]-quinoxalin-2-yl}-pyridine-2-carboxylic acid (2-dimethylamino-ethyl)-methyl-amide

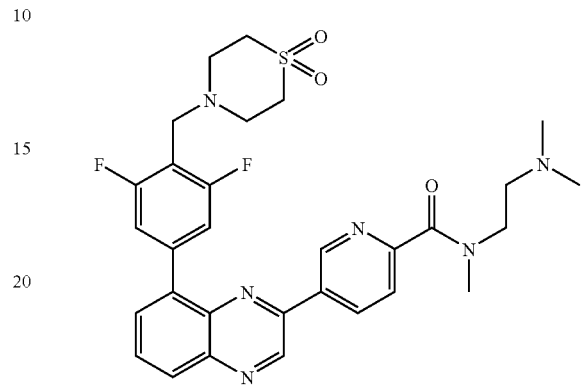

R$_t$=0.809 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 595 (M+1)⁺

Using the same synthetic methods as described in Example 1, but utilizing 5-(8-Bromo-quinoxalin-2-yl)-3-methyl-pyridine-2-carboxylic acid (2-dimethylamino-ethyl)-methyl-amide [prepared analogously to step 1.5 but utilizing 3-Methyl-5-(4,4,5,5-tetramethyl-[1,3,2]dioxaborolan-2-yl)-pyridine-2-carboxylic acid (2-dimethylamino-ethyl)-methyl-amide in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples

Example 112

5-[8-(3,5-Difluoro-4-morpholin-4-ylmethyl-phenyl)-quinoxalin-2-yl]-3-methyl-pyridine-2-carboxylic acid (2-dimethylamino-ethyl)-methyl-amide

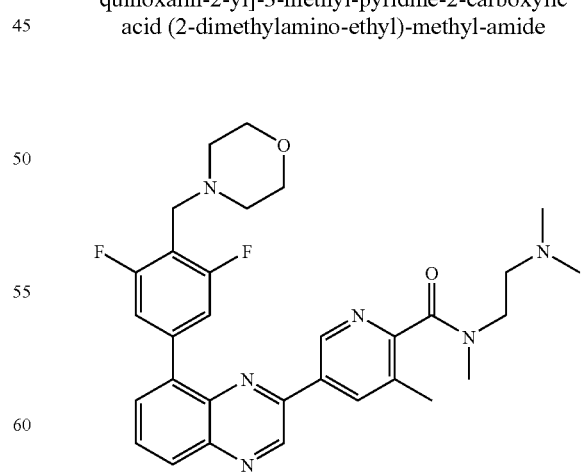

R$_t$=0.697 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 561 (M+1)⁺

Example 113

5-{8-[4-(1,1-Dioxido-thiomorpholin-4-ylmethyl)-3,5-difluoro-phenyl]-quinoxalin-2-yl}-3-methyl-pyridine-2-carboxylic acid (2-dimethylamino-ethyl)-methyl-amide

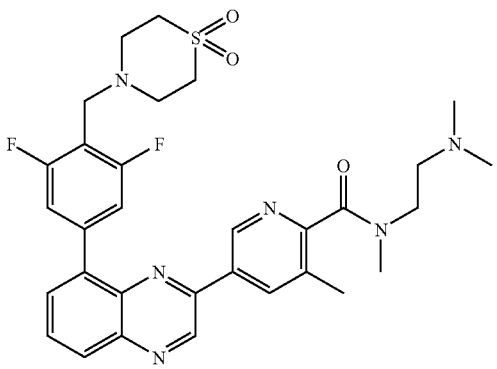

$R_t$=0.832 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 609 (M+1)$^+$ Using the same synthetic methods as described in Example 1, but utilizing 8-Bromo-2-[1-(3-morpholin-4-yl-propyl)-1H-pyrazol-4-yl]-quinoxaline [prepared analogously to step 1.5 but utilizing 4-{3-[4-(4,4,5,5-Tetramethyl-[1,3,2]dioxaborolan-2-yl)-pyrazol-1-yl]-propyl}-morpholine in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Example

Example 114

(2-Methyl-4-{3-[1-(3-morpholin-4-yl-propyl)-1H-pyrazol-4-yl]-quinoxalin-5-yl}-phenyl)-morpholin-4-yl-methanone

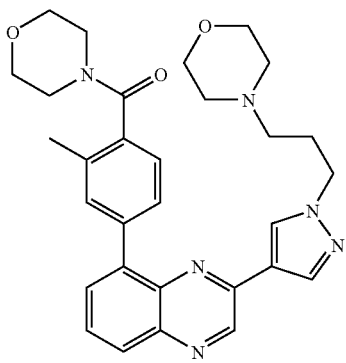

$R_t$=0.838 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 527 (M+1)$^+$ Using the same synthetic methods as described in Example 1, but utilizing 8-Bromo-2-[1-(2-methoxy-ethyl)-1H-pyrazol-4-yl]-quinoxaline [prepared analogously to step 1.5 but utilizing 1-(2-Methoxy-ethyl)-4-(4,4,5,5-tetramethyl-[1,3,2]dioxaborolan-2-yl)-1H-pyrazole in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Example

Example 115

8-(3,5-Difluoro-4-morpholin-4-ylmethyl-phenyl)-2-[1-(2-methoxy-ethyl)-1H-pyrazol-4-yl]-quinoxaline

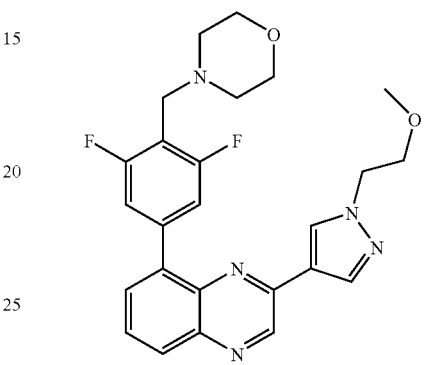

$R_t$=0.805 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 466 (M+1)$^+$ Using the same synthetic methods as described in Example 1, but utilizing 2-(1-Azetidin-3-yl-1H-pyrazol-4-yl)-8-bromo-quinoxaline [prepared analogously to the steps 94.1 and 94.2, but using 3-[4-(4,4,5,5-Tetramethyl-[1,3,2]dioxaborolan-2-yl)-pyrazol-1-yl]-azetidine-1-carboxylic acid tert-butyl ester] in lieu of 8-Bromo-2-(3,4,5-trimethoxy-phenyl)-quinoxaline and the appropriate boronic acid or ester derivative leads to the following Examples

Example 116

2-(1-Azetidin-3-yl-1H-pyrazol-4-yl)-8-(3,5-difluoro-4-morpholin-4-ylmethyl-phenyl)-quinoxaline

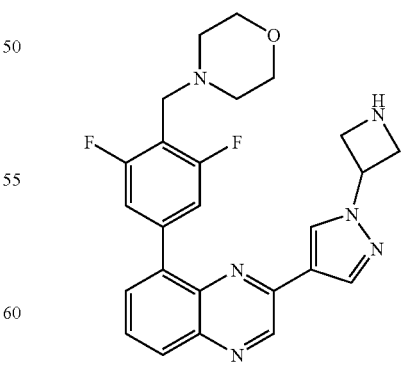

$R_t$=0.664 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 463 (M+1)$^+$ Using the same synthetic methods as described in Example 1, but utilizing 8-Bromo-2-[1-(tetrahydro-pyran-4-yl)-1H-pyrazol-4-yl]-quinoxaline [prepared analogously to step 1.5 but utilizing 1-(Tetrahydro-pyran-4-yl)-4-(4,4,5,5-tetramethyl-[1,3,2]dioxaborolan-2-yl)-1H-pyrazole in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples Example 117

8-(3,5-Difluoro-4-morpholin-4-ylmethyl-phenyl)-2-[1-(tetrahydro-pyran-4-yl)-1H-pyrazol-4-yl]-quinoxaline

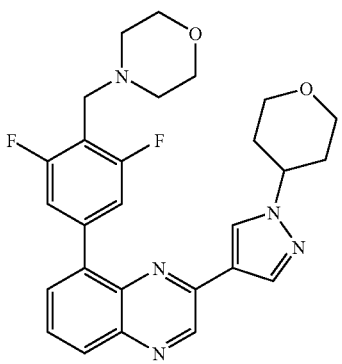

$R_t$=0.823 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 492 (M+1)$^+$ Example 118

4-(2,6-Difluoro-4-{3-[1-(tetrahydro-pyran-4-yl)-1H-pyrazol-4-yl]-quinoxalin-5-yl}-benzyl)-piperazin-2-one

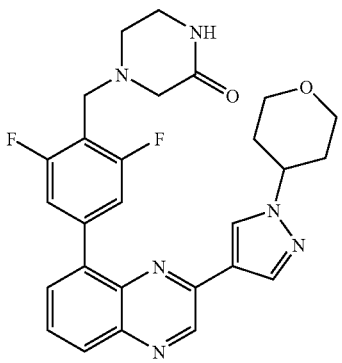

$R_t$=0.795 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 505 (M+1)$^+$ Example 119

(2,6-Difluoro-4-{3-[1-(tetrahydro-pyran-4-yl)-1H-pyrazol-4-yl]-quinoxalin-5-yl}-phenyl)-morpholin-4-yl-methanone

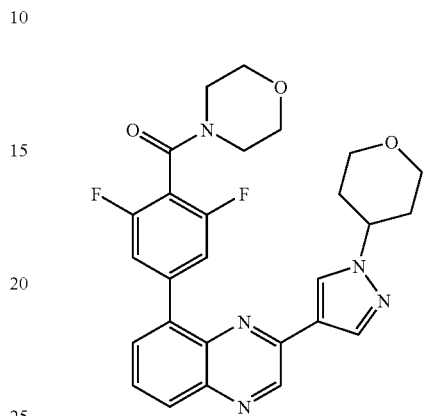

$R_t$=1.042 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 506 (M+1)$^+$ Using the same synthetic methods as described in Example 1, but utilizing 4-(8-Bromo-quinoxalin-2-yl)-N-(2-hydroxy-ethyl)-2-methyl-benzamide [prepared analogously to step 1.5 but utilizing N-(2-Hydroxy-ethyl)-2-methyl-4-(4,4,5,5-tetramethyl-[1,3,2]dioxaborolan-2-yl)-benzamide in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Example Example 120

4-[8-(3,5-Difluoro-4-morpholin-4-ylmethyl-phenyl)-quinoxalin-2-yl]-N-(2-hydroxy-ethyl)-2-methyl-benzamide

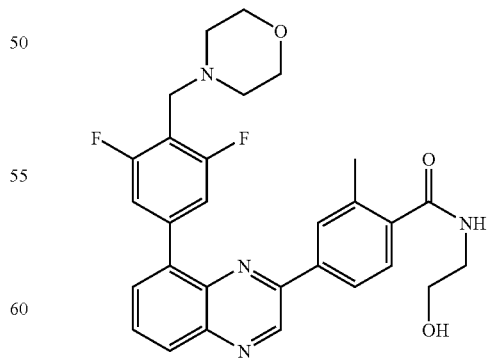

$R_t$=0.769 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 519 (M+1)$^+$ Using the same synthetic methods as described in Example 1, but utilizing 1-{4-[4-(8-Bromo-quinoxalin-2-yl)-pyrazol-1-yl]-piperidin-1-yl}-ethanone [prepared analogously to step 1.5 but utilizing 1-{4-[4-(4,4,5,5-Tetramethyl-[1,3,2]diox-aborolan-2-yl)-pyrazol-1-yl]-piperidin-1-yl]-ethanone in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Example

Example 121

1-(4-{4-[8-(3,5-Difluoro-4-morpholin-4-ylmethyl-phenyl)-quinoxalin-2-yl]-pyrazol-1-yl}-piperidin-1-yl)-ethanone

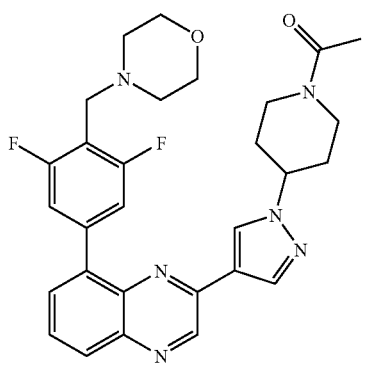

$R_t$=0.792 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+ 0.1% TFA, flow rate 1.0 ml/min); MS: 533 $(M+1)^+$ 2-chloroethylmethyl ether (13.5 µl, 0.143 mmol) is added dropwise to a solution of 8-(3,5-Difluoro-4-morpholin-4-yl-methyl-phenyl)-2-(1-piperidin-4-yl-1H-pyrazol-4-yl)-quinoxaline (as obtained in example 98, 67 mg, 0.137 mmol), $Cs_2CO_3$ (24 mg, 0.075 mmol) in DMF (0.5 ml). The resulting mixture is heated under Ar at 95° C. for 17 h. Two products are formed in a ratio 1:1, as identified by example 122 and example 123. The reaction is quenched with water and extracted with EtOAc several times. The combined organic layers are washed with brine, dried over $Na_2SO_4$, filtered and the filtrate is concentrated in vacuo. The residue is purified by chromatography on a 40 g silica gel column on a Combiflash Companion™ (Isco Inc.) apparatus (gradient $CH_2Cl_2$/($CH_2Cl_2$:EtOH:$NH_3$ 90:9:1) from 1:0=>0:1) to afford example 122 and example 123.

Example 122

4-{4-[8-(3,5-Difluoro-4-morpholin-4-ylmethyl-phenyl)-quinoxalin-2-yl]-pyrazol-1-yl}-piperidine-1-carboxylic acid 2-methoxy-ethyl ester

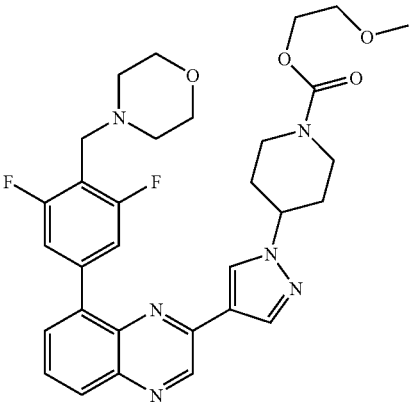

$R_t$=0.871 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+ 0.1% TFA, flow rate 1.0 ml/min); MS: 593 $(M+1)^+$

Example 123

8-(3,5-Difluoro-4-morpholin-4-ylmethyl-phenyl)-2-{1-[1-(2-methoxy-ethyl)-piperidin-4-yl]-1H-pyrazol-4-yl}-quinoxaline

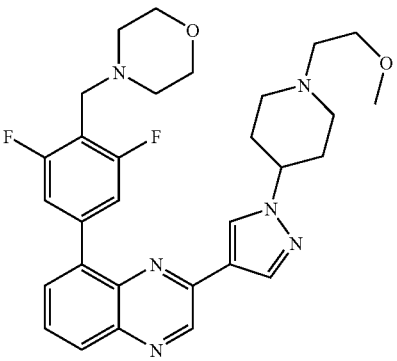

$R_t$=0.702 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+ 0.1% TFA, flow rate 1.0 ml/min); MS: 549 $(M+1)^+$

Example 124

4-{4-[8-(3,5-Difluoro-4-morpholin-4-ylmethyl-phenyl)-quinoxalin-2-yl]-5-methyl-pyrazol-1-yl}-piperidine-1-carboxylic acid tert-butyl ester

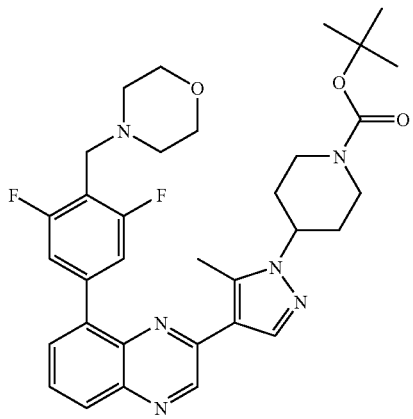

The title compound is prepared using the same synthetic methods as described in Example 1, but utilizing 4-[4-(8-Bromo-quinoxalin-2-yl)-5-methyl-pyrazol-1-yl]-piperidine-1-carboxylic acid tert-butyl ester [prepared analogously to step 96.1 but utilizing 445-Methyl-4-(4,4,5,5-tetramethyl-[1,3,2]dioxaborolan-2-yl)-pyrazol-1-yl]-piperidine-1-carboxylic acid tert-butyl ester] in lieu of 8-Bromo-2-(3,4,5-trimethoxy-phenyl)-quinoxaline and the appropriate boronic acid or ester.

$R_f$=1.037 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+0.1% TFA, flow rate 1.0 ml/min); MS: 605 $(M+1)^+$

Example 125

8-(3,5-Difluoro-4-morpholin-4-ylmethyl-phenyl)-2-(5-methyl-1-piperidin-4-yl-1H-pyrazol-4-yl)-quinoxaline

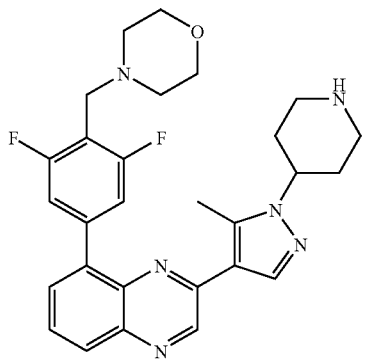

A 1.25 M solution of HCl in EtOH (5 ml, 6.26 mmol) is added to 4-{4-[8-(3,5-Difluoro-4-morpholin-4-ylmethyl-phenyl)-quinoxalin-2-yl]-5-methyl-pyrazol-1-yl}-piperidine-1-carboxylic acid tert-butyl ester (Example 121, 239 mg, 0.368 mmol) and the reaction mixture is heated at 60° C. for 4 h. After cooling, the yellow suspension is concentrated under vacuo and the residue is diluted with EtOAc, poured onto a saturated solution of $NaHCO_3$ and extracted 3× with EtOAc. The combined organic layers are washed with $NaHCO_3$, brine, dried over $Na_2SO_4$, filtered and the filtrate is concentrated in vacuo. The residue is dissolved in $CH_2Cl_2$ and purified by chromatography on a 40 g silica gel column on a Combiflash Companion™ (Isco Inc.) apparatus (gradient $CH_2Cl_2/(CH_2Cl_2$:EtOH:$NH_3$ 85:13.5:1.5) from 1:0=>1:9) to afford the title compound as a pale orange foam. $R_f$=0.703 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+0.1% TFA, flow rate 1.0 ml/min); MS: 505 $(M+1)^+$

Example 126

4-{4-[8-(3,5-Difluoro-4-morpholin-4-ylmethyl-phenyl)-quinoxalin-2-yl]-3-methyl-pyrazol-1-yl}-piperidine-1-carboxylic acid tert-butyl ester

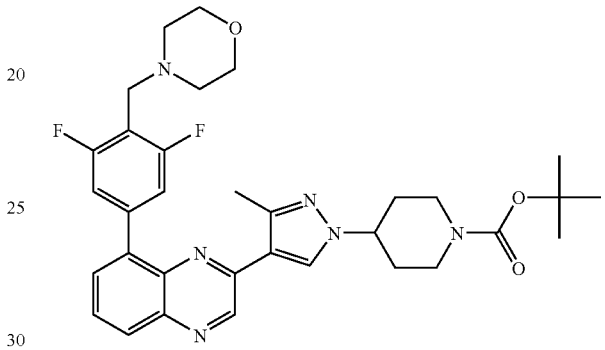

The title compound is obtained analogously to example 124 but using 4-[4-(8-Bromo-quinoxalin-2-yl)-3-methyl-pyrazol-1-yl]-piperidine-1-carboxylic acid tert-butyl ester. $R_f$=1.030 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+0.1% TFA, flow rate 1.0 ml/min); MS: 605 $(M+1)^+$

Example 127

8-(3,5-Difluoro-4-morpholin-4-ylmethyl-phenyl)-2-(3-methyl-1-piperidin-4-yl-1H-pyrazol-4-yl)-quinoxaline

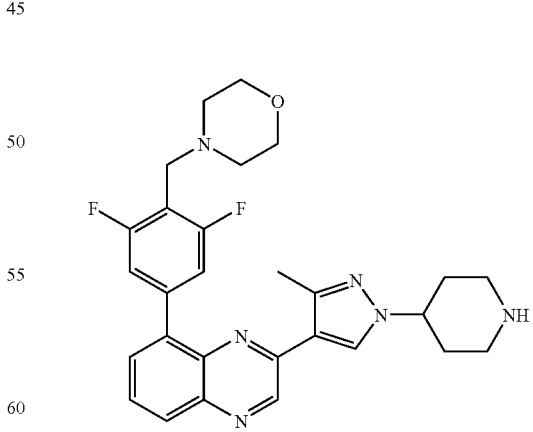

The title compound is obtained analogously to example 125 but using 4-{4-[8-(3,5-Difluoro-4-morpholin-4-ylmethyl-phenyl)-quinoxalin-2-yl]-3-methyl-pyrazol-1-yl}-piperidine-1-carboxylic acid tert-butyl ester (as obtained in example 126). $R_f$=0.690 min (Acquity HPLC BEH C18, 2.1×

50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 505 (M+1)$^+$ Example 128

2-[1-(1-Cyclopropyl-piperidin-4-yl)-1H-pyrazol-4-yl]-8-(3,5-difluoro-4-morpholin-4-ylmethyl-phenyl)-quinoxaline

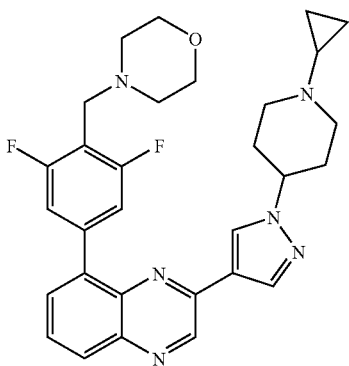

The title compound is obtained using the same synthetic methods as described in Example 1, but utilizing 8-Bromo-2-[1-(1-cyclopropyl-piperidin-4-yl)-1H-pyrazol-4-yl]-quinoxaline in lieu of 8-Bromo-2-(3,4,5-trimethoxy-phenyl)-quinoxaline and the appropriate boronic acid or ester. R$_t$=0.968 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 531 (M+1)$^+$ Example 129

Cyclopropyl-(4-{4-[8-(3,5-difluoro-4-morpholin-4-ylmethyl-phenyl)-quinoxalin-2-yl]-pyrazol-1-yl}-piperidin-1-yl)-methanone

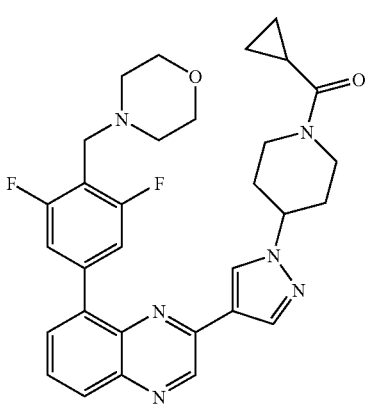

Cyclopropanecarbonyl chloride (23 μl, 0.245 mmol) is added dropwise, under stirring at 0° C., to a solution of 8-(3,5-Difluoro-4-morpholin-4-ylmethyl-phenyl)-2-(1-piperidin-4-yl-1H-pyrazol-4-yl)-quinoxaline (as obtained in example 98, 120 mg, 0.245 mmol), Et$_3$N (103 μl, 0.734 mmol) in CH$_2$Cl$_2$. The cooling bath is then removed and the reaction mixture stirred at RT for an additional 30 min. The mixture is then diluted with de-ionized water and the phases are separated. The organic phase is washed several times with de-ionized water and the aqueous layer re-extracted with CH$_2$Cl$_2$. The combined organic layers are washed with brine, dried over Na$_2$SO$_4$, filtered and the filtrate is concentrated in vacuo. The residue is dissolved in CH$_2$Cl$_2$ and purified by chromatography on a 12 g silica gel column on a Combiflash Companion™ (Isco Inc.) apparatus (gradient CH$_2$Cl$_2$/(CH$_2$Cl$_2$:EtOH:NH$_3$ 90:9:1.1) from 1:0 =>1:9) to afford the title compound as a pale yellow foam. R$_t$=0.852 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 559 (M+1)$^+$ Example 130

4-{4-[8-(3,5-Difluoro-4-morpholin-4-ylmethyl-phenyl)-quinoxalin-2-yl]-pyrazol-1-yl}-piperidine-1-carboxylic acid methyl ester

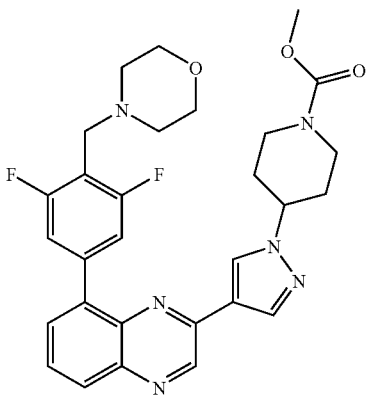

Dimethyldicarbonate (27 μl, 0.245 mmol) is added dropwise, under stirring at 0° C., to a solution of 8-(3,5-Difluoro-4-morpholin-4-ylmethyl-phenyl)-2-(1-piperidin-4-yl-1H-pyrazol-4-yl)-quinoxaline (as obtained in example 98, 120 mg, 0.245 mmol) in THF. The cooling bath is then removed and the reaction mixture stirred at RT for an additional 30 min. The mixture is then diluted with de-ionized water and the phases are separated. The organic phase is washed several times with de-ionized water and the aqueous layer re-extracted with CH$_2$Cl$_2$. The combined organic layers are washed with brine, dried over Na$_2$SO$_4$, filtered and the filtrate is concentrated in vacuo. The residue is dissolved in CH$_2$Cl$_2$ and purified by chromatography on a 12 g silica gel column on a Combiflash Companion™ (Isco Inc.) apparatus (gradient CH$_2$Cl$_2$/(CH$_2$Cl$_2$: EtOH: NH$_3$ 90:9:1.1) from 1:0=>1:9) to afford the title compound as a pale yellow foam. R$_t$=0.865 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 549 (M+1)$^+$

Example 131

1-(4-{4-[8-(3,5-Difluoro-4-morpholin-4-ylmethyl-phenyl)-quinoxalin-2-yl]-3-methyl-pyrazol-1-yl}-piperidin-1-yl)-2-methyl-propan-1-one

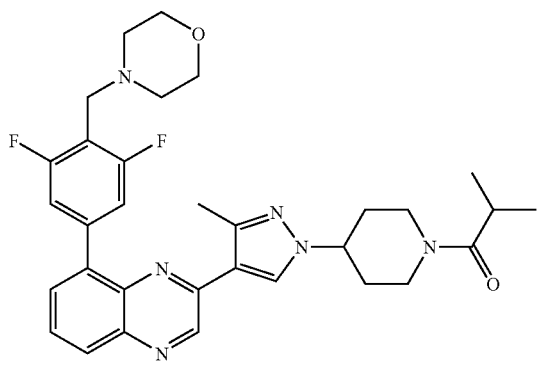

The title compound is obtained analogously to example 129, but using 8-(3,5-Difluoro-4-morpholin-4-ylmethyl-phenyl)-2-(3-methyl-1-piperidin-4-yl-1H-pyrazol-4-yl)-quinoxaline (as obtained in example 127) and isobutyryl chloride, $R_t$=0.885 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+0.1% TFA, flow rate 1.0 ml/min); MS: 575 $(M+1)^+$

Example 132

4-{4-[8-(3,5-Difluoro-4-morpholin-4-ylmethyl-phenyl)-quinoxalin-2-yl]-pyrazol-1-ylmethyl}-piperidine-1-carboxylic acid tert-butyl ester

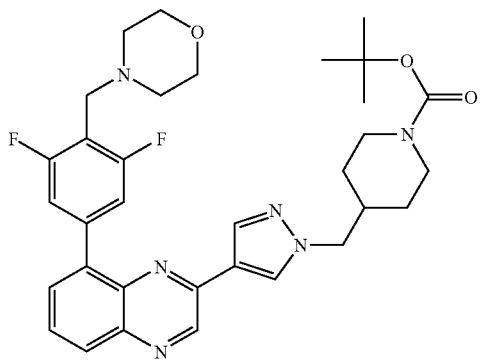

The title compound is prepared using the same synthetic methods as described in Example 1, but utilizing 4-[4-(8-Bromo-quinoxalin-2-yl)-pyrazol-1-ylmethyl]-piperidine-1-carboxylic acid tert-butyl ester [prepared analogously to step 96.1 but utilizing 4-[4-(4,4,5,5-Tetramethyl-[1,3,2]dioxaborolan-2-yl)-pyrazol-1-ylmethyl]-piperidine-1-carboxylic acid tert-butyl ester, as obtained in preparation 101] in lieu of 8-Bromo-2-(3,4,5-trimethoxy-phenyl)-quinoxaline and the appropriate boronic acid or ester.

$R_t$=1.020 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+0.1% TFA, flow rate 1.0 ml/min); MS: 605 $(M+1)^+$

Example 133

8-(3,5-Difluoro-4-morpholin-4-ylmethyl-phenyl)-2-(1-piperidin-4-ylmethyl-1H-pyrazol-4-yl)-quinoxaline

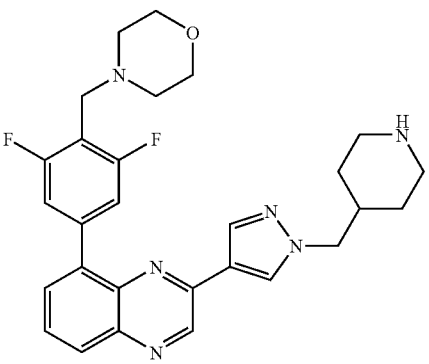

The title compound is obtained analogously to example 125 but using 4-{4-[8-(3,5-Difluoro-4-morpholin-4-ylmethyl-phenyl)-quinoxalin-2-yl]-pyrazol-1-ylmethyl}-piperidine-1-carboxylic acid tert-butyl ester (as obtained in example 132). $R_t$=0.681 min (Acquity HPLC BEH C18, 2.1×50 mm, 1.7 micron, detection 215 nM, 0.1 min 2% $CH_3CN$ in $H_2O$, 2% to 100% $CH_3CN$ in $H_2O$ in 1.5 min, 0.4 min 100% $CH_3CN$+0.1% TFA, flow rate 1.0 ml/min); MS: 505 $(M+1)^+$

Example 134

(rac)-3-{4-[8-(3,5-Difluoro-4-morpholin-4-ylmethyl-phenyl)-quinoxalin-2-yl]-pyrazol-1-ylmethyl}-piperidine-1-carboxylic acid tert-butyl ester

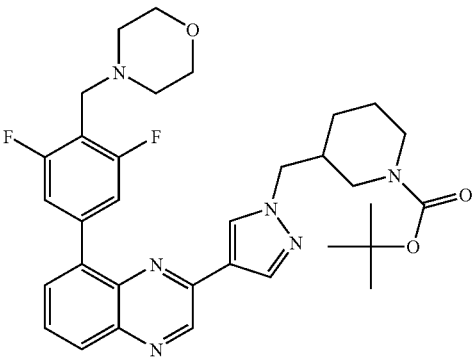

The title compound is prepared using the same synthetic methods as described in Example 1, but utilizing (rac)-3-[4-(8-Bromo-quinoxalin-2-yl)-pyrazol-1-ylmethyl]-piperidine-1-carboxylic acid tert-butyl ester [prepared analogously to step 96.1 but utilizing (rac)-3-[4-(4,4,5,5-Tetramethyl-[1,3,2]dioxaborolan-2-yl)-pyrazol-1-ylmethyl]-piperidine-1-carboxylic acid tert-butyl ester, as obtained in preparation 100] in lieu of 8-Bromo-2-(3,4,5-trimethoxy-phenyl)-quinoxaline and the appropriate boronic acid or ester.

$R_t$=1.015 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 605 (M+1)$^+$ Example 135

(rac)-8-(3,5-Difluoro-4-morpholin-4-ylmethyl-phenyl)-2-(1-piperidin-3-ylmethyl-1H-pyrazol-4-yl)-quinoxaline

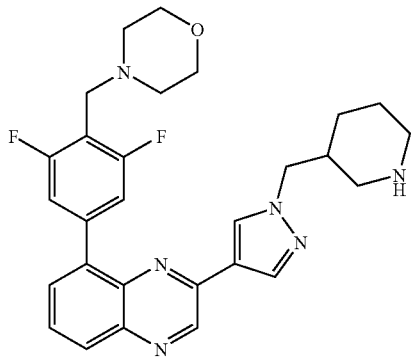

The title compound is obtained analogously to example 125 but using (rac)-3-{4-[8-(3,5-Difluoro-4-morpholin-4-ylmethyl-phenyl)-quinoxalin-2-yl]-pyrazol-1-ylmethyl}-piperidine-1-carboxylic acid tert-butyl ester (as obtained in example 134). $R_t$=0.685 min (Acquity HPLC BEH C18, 2.1× 50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 505 (M+1)$^+$ Using 4-[4-(8-Bromo-quinoxalin-2-yl)-pyrazol-1-yl]-piperidine-1-carboxylic acid tert-butyl ester (as obtained in step 96.1) and the appropriate boronic acid or ester derivative the following Examples are prepared Example 136

4-{4-[8-(3,5-Difluoro-4-morpholin-4-ylmethyl-phenyl)-quinoxalin-2-yl]-pyrazol-1-yl}-piperidine-1-carboxylic acid tert-butyl ester

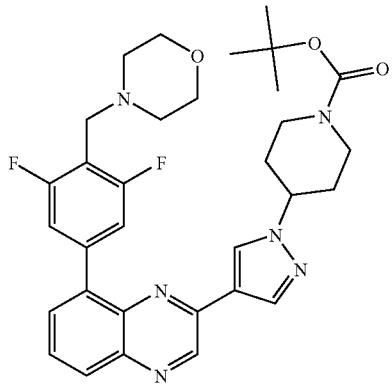

$R_t$=1.014 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 591 (M+1)$^+$ Example 137

4-{4-[8-(4-Methanesulfonyl-phenyl)-quinoxalin-2-yl]-pyrazol-1-yl}-piperidine-1-carboxylic acid tert-butyl ester

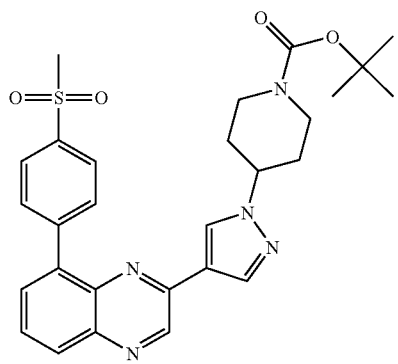

$R_t$=1.216 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 534 (M+1)$^+$ Example 138

4-{4-[8-(3-Fluoro-4-morpholin-4-ylmethyl-phenyl)-quinoxalin-2-yl]-pyrazol-1-yl}-piperidine-1-carboxylic acid tert-butyl ester

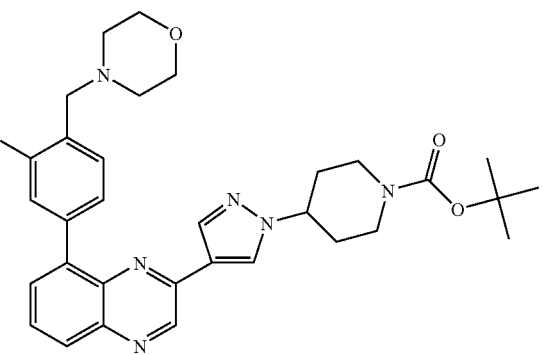

$R_t$=1.004 min (Acquity HPLC BEH C18, 2.1×50 mm, 1.7 micron, detection 215 nM, 0.1 min 2% CH$_3$CN in H$_2$O, 2% to 100% CH₃CN in H₂O in 1.5 min, 0.4 min 100% CH₃CN+ 0.1% TFA, flow rate 1.0 ml/min); MS: 573 (M+1)⁺

Example 139

4-{4-[8-(3-Methyl-4-morpholin-4-ylmethyl-phenyl)-quinoxalin-2-yl]-pyrazol-1-yl}-piperidine-1-carboxylic acid tert-butyl ester

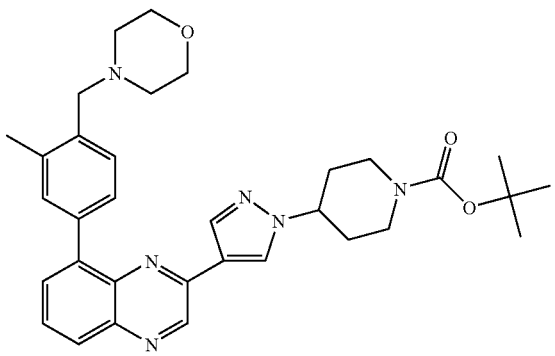

R$_t$=1.024 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 569 (M+1)⁺

Example 140

4-{4-[8-(2-Methyl-4-morpholin-4-ylmethyl-phenyl)-quinoxalin-2-yl]-pyrazol-1-yl}-piperidine-1-carboxylic acid tert-butyl ester

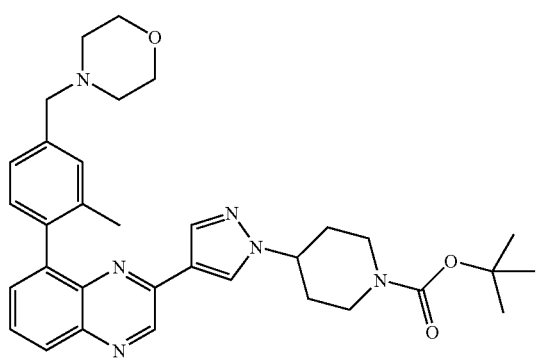

R$_t$=1.021 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 569 (M+1)⁺

Example 141

4-(4-{8-[4-(1,1-Dioxido-thiomorpholin-4-ylmethyl)-phenyl]-quinoxalin-2-yl}-pyrazol-1-yl)-piperidine-1-carboxylic acid tert-butyl ester

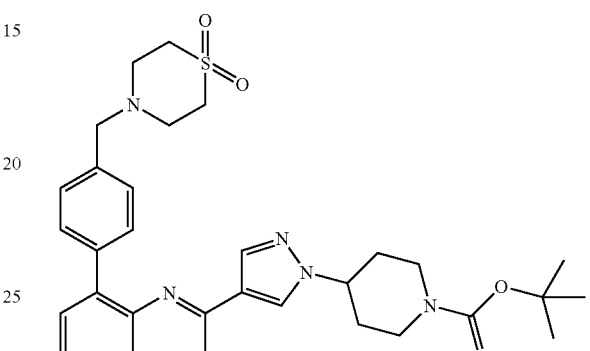

R$_t$=1.026 min (Acquity HPLC BEH C18, 2.1×50 mm, 1.7 micron, detection 215 nM, 0.1 min 2% CH₃CN in H₂O, 2% to 100% CH₃CN in H₂O in 1.5 min, 0.4 min 100% CH₃CN+ 0.1% TFA, flow rate 1.0 ml/min); MS: 603 (M+1)⁺

Example 142

4-(4-{8-[4-(1,1-Dioxido-thiomorpholin-4-ylmethyl)-2-methyl-phenyl]-quinoxalin-2-yl}-pyrazol-1-yl)-piperidine-1-carboxylic acid tert-butyl ester

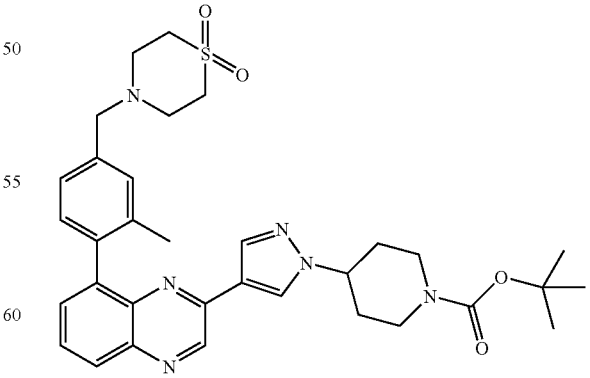

R$_t$=1.044 min (Acquity HPLC BEH C18, 2.1×50 mm, 1.7 micron, detection 215 nM, 0.1 min 2% CH₃CN in H₂O, 2% to 100% CH$_3$CN in H$_2$O in 1.5 min, 0.4 min 100% CH$_3$CN+ 0.1% TFA, flow rate 1.0 ml/min); MS: 617 (M+1)$^+$ Example 143

4-{4-[8-(4-Morpholin-4-ylmethyl-phenyl)-quinoxalin-2-yl]-pyrazol-1-yl}-piperidine-1-carboxylic acid tert-butyl ester

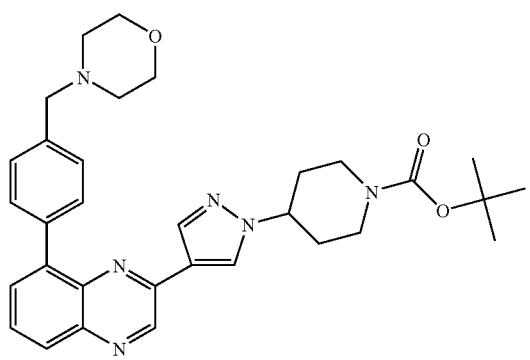

R$_t$=0.994 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 555 (M+1)$^+$ The following compounds are obtained analogously to example 125 but using the appropriate starting material from examples 137 to 143:

Example 144

8-(4-Methanesulfonyl-phenyl)-2-(1-piperidin-4-yl-1H-pyrazol-4-yl)-quinoxaline

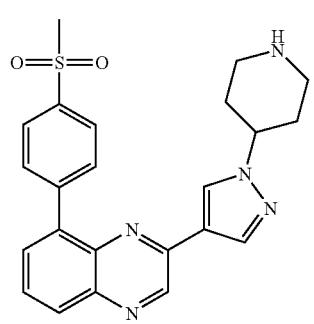

R$_t$=0.807 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 434 (M+1)$^+$ Example 145

8-(3-Fluoro-4-morpholin-4-ylmethyl-phenyl)-2-(1-piperidin-4-yl-1H-pyrazol-4-yl)-quinoxaline

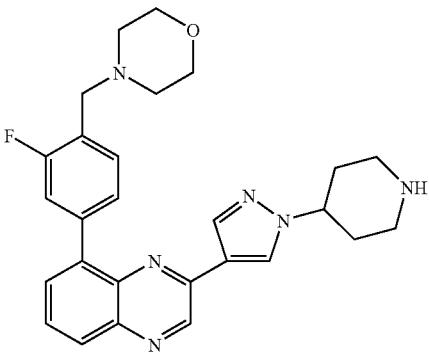

R$_t$=0.676 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 473 (M+1)$^+$ Example 146

8-(3-Methyl-4-morpholin-4-ylmethyl-phenyl)-2-(1-piperidin-4-yl-1H-pyrazol-4-yl)-quinoxaline

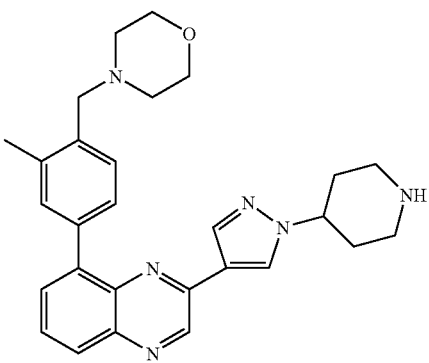

R$_t$=0.699 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 469 (M+1)$^+$ Example 147

8-(2-Methyl-4-morpholin-4-ylmethyl-phenyl)-2-(1-piperidin-4-yl-1H-pyrazol-4-yl)-quinoxaline

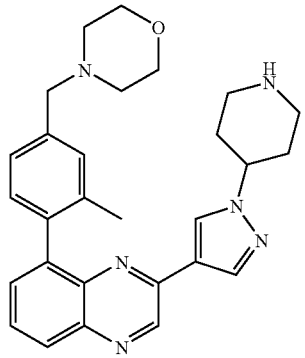

R$_t$=0.726 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 469 (M+1)$^+$ Example 148

8-[4-(1,1-Dioxido-thiomorpholin-4-ylmethyl)-phenyl]-2-(1-piperidin-4-yl-1H-pyrazol-4-yl)-quinoxaline

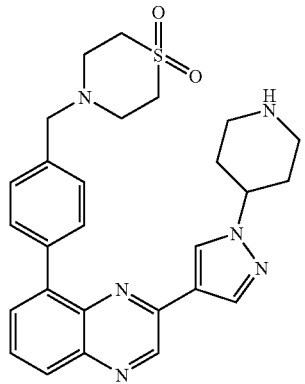

R$_t$=0.700 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 503 (M+1)$^+$ Example 149

8-[4-(1,1-Dioxido-thiomorpholin-4-ylmethyl)-2-methyl-phenyl]-2-(1-piperidin-4-yl-1H-pyrazol-4-yl)-quinoxaline

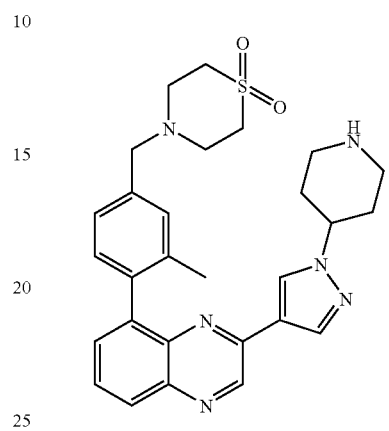

R$_t$=0.724 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 517 (M+1)$^+$ Example 150

8-(4-Morpholin-4-ylmethyl-phenyl)-2-(1-piperidin-4-yl-1H-pyrazol-4-yl)-quinoxaline

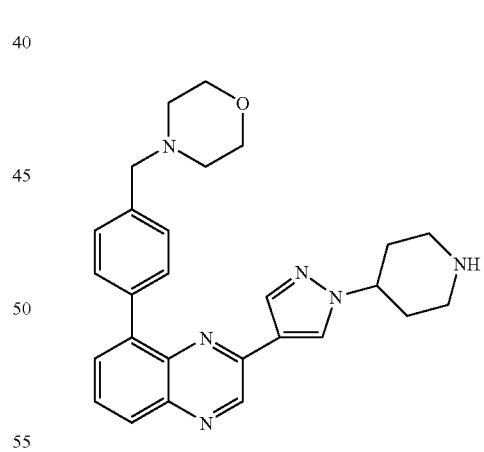

R$_t$=0.670 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 455 (M+1)$^+$ Using 4-[4-(8-Bromo-quinoxalin-2-yl)-3,5-dimethyl-pyrazol-1-yl]-piperidine-1-carboxylic acid tert-butyl ester [prepared analogously to step 96.1 but utilizing 4-[3,5-Dimethyl-4-(4,4,5,5-tetramethyl-[1,3,2]dioxaborolan-2-yl)-pyrazol-1-yl]-piperidine-1-carboxylic acid tert-butyl ester] and the appropriate boronic acid or ester derivative the following Examples are prepared

Example 151

4-{4-[8-(3,5-Difluoro-4-morpholin-4-ylmethyl-phenyl)-quinoxalin-2-yl]-3,5-dimethyl-pyrazol-1-yl}-piperidine-1-carboxylic acid tert-butyl ester

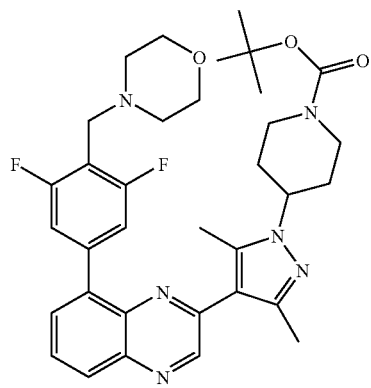

$R_t$=1.072 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 619 (M+1)$^+$

Example 152

4-{3,5-Dimethyl-4-[8-(4-morpholin-4-ylmethyl-phenyl)-quinoxalin-2-yl]-pyrazol-1-yl}-piperidine-1-carboxylic acid tert-butyl ester

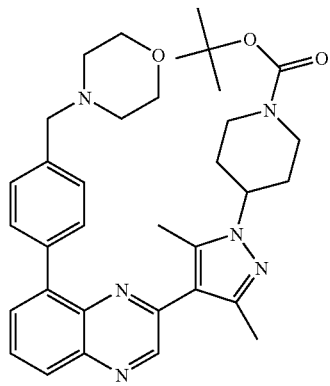

$R_t$=1.053 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 583 (M+1)$^+$

Example 153

4-(4-{8-[4-(1,1-Dioxido-thiomorpholin-4-ylmethyl)-phenyl]-quinoxalin-2-yl}-3,5-dimethyl-pyrazol-1-yl)-piperidine-1-carboxylic acid tert-butyl ester

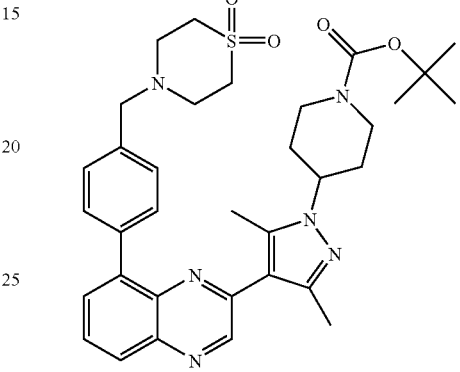

$R_t$=1.095 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 631 (M+1)$^+$

Example 154

4-{3,5-Dimethyl-4-[8-(3-methyl-4-morpholin-4-ylmethyl-phenyl)-quinoxalin-2-yl]-pyrazol-1-yl}-piperidine-1-carboxylic acid tert-butyl ester

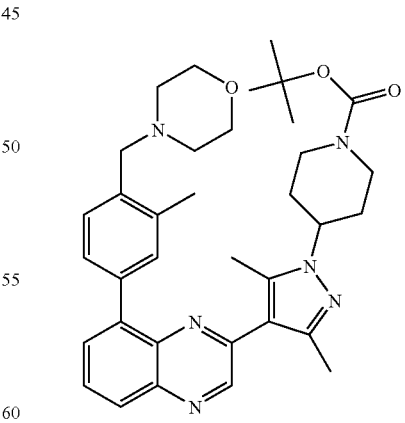

$R_t$=1.083 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 597 (M+1)$^+$ The following compounds are obtained analogously to example 125 but using the appropriate starting material from examples 151 to 154:

Example 155

8-(3,5-Difluoro-4-morpholin-4-ylmethyl-phenyl)-2-(3,5-dimethyl-1-piperidin-4-yl-1H-pyrazol-4-yl)-quinoxaline

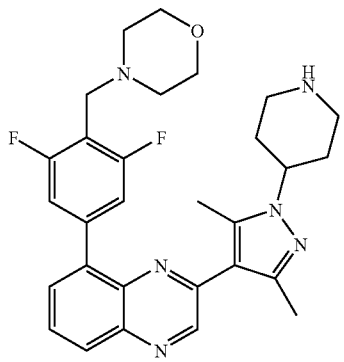

$R_t$=0.725 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 519 (M+1)$^+$

Example 156

2-(3,5-Dimethyl-1-piperidin-4-yl-1H-pyrazol-4-yl)-8-(4-morpholin-4-ylmethyl-phenyl)-quinoxaline

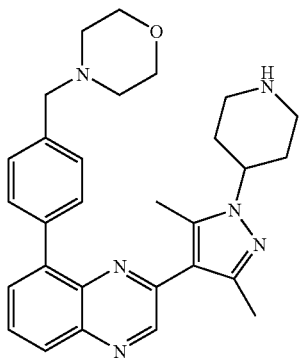

$R_t$=0.728 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 483 (M+1)$^+$

Example 157

2-(3,5-Dimethyl-1-piperidin-4-yl-1H-pyrazol-4-yl)-8-[4-(1,1-dioxido-thiomorpholin-4-ylmethyl)-phenyl]-quinoxaline

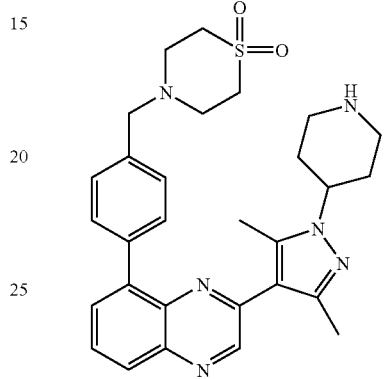

$R_t$=0.766 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 531 (M+1)$^+$

Example 158

2-(3,5-Dimethyl-1-piperidin-4-yl-1H-pyrazol-4-yl)-8-(3-methyl-4-morpholin-4-ylmethyl-phenyl)-quinoxaline

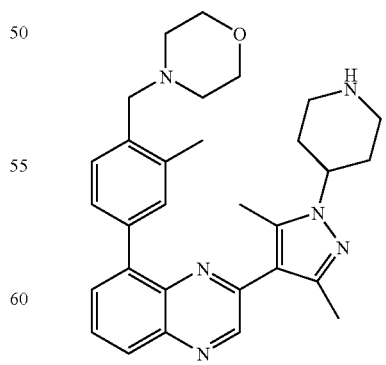

$R_t$=0.751 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 497 (M+1)$^+$ Example 159

(rac)-3-{4-[8-(3,5-Difluoro-4-morpholin-4-ylmethyl-phenyl)-quinoxalin-2-yl]-pyrazol-1-yl}-piperidine-1-carboxylic acid tert-butyl ester

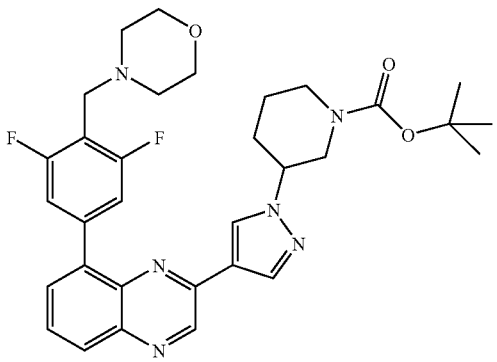

The title compound is prepared using the same synthetic methods as described in Example 1, but utilizing (rac)-3-[4-(8-Bromo-quinoxalin-2-yl)-pyrazol-1-yl]-piperidine-1-carboxylic acid tert-butyl ester [prepared analogously to step 96.1 but utilizing (rac)-3-[4-(4,4,5,5-Tetramethyl-[1,3,2]dioxaborolan-2-yl)-pyrazol-1-yl]-piperidine-1-carboxylic acid tert-butyl ester, as obtained in preparation 103] in lieu of 8-Bromo-2-(3,4,5-trimethoxy-phenyl)-quinoxaline and the appropriate boronic acid or ester.

R$_t$=1.046 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+ 0.1% TFA, flow rate 1.0 ml/min); MS: 591 (M+1)$^+$ Example 160

(rac)-8-(3,5-Difluoro-4-morpholin-4-ylmethyl-phenyl)-2-(1-piperidin-3-yl-1H-pyrazol-4-yl)-quinoxaline

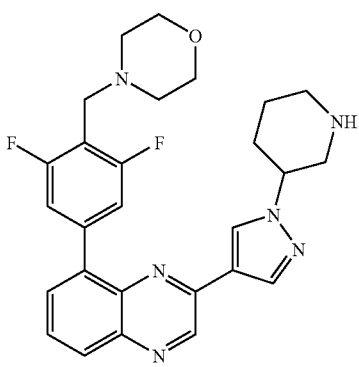

The title compound is obtained analogously to example 125 but using (rac)-3-{4-[8-(3,5-Difluoro-4-morpholin-4-ylmethyl-phenyl)-quinoxalin-2-yl]-pyrazol-1-yl}-piperidine-1-carboxylic acid tert-butyl ester (as obtained in example 159). R$_t$=0.697 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 491 (M+1)$^+$ Using the same synthetic methods as described in Example 1, but utilizing 8-Bromo-2-[4-methoxy-3-(4-methyl-piperazin-1-yl)-phenyl]-quinoxaline [prepared analogously to step 1.5 but utilizing 1-[2-Methoxy-5-(4,4,5,5-tetramethyl-[1,3,2]dioxaborolan-2-yl)-phenyl]-4-methyl-piperazine in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples Example 161

8-[4-(1,1-Dioxido-thiomorpholin-4-ylmethyl)-phenyl]-2-[4-methoxy-3-(4-methyl-piperazin-1-yl)-phenyl]-quinoxaline

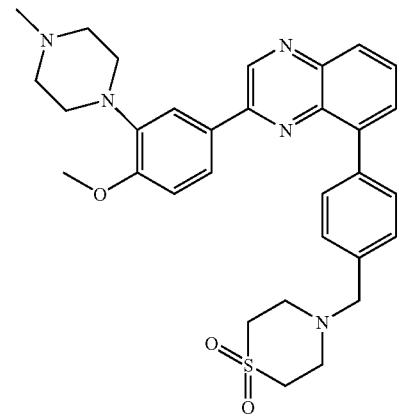

R$_t$=4.81 min (HPLC conditions B); MS: 558 (M+1)$^+$

Example 162

8-(3,5-Difluoro-4-morpholin-4-ylmethyl-phenyl)-2-[4-methoxy-3-(4-methyl-piperazin-1-yl)-phenyl]-quinoxaline

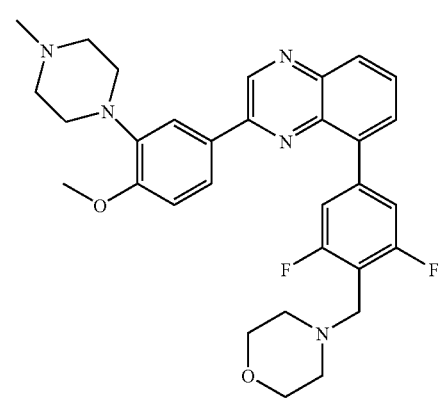

R$_t$=4.68 min (HPLC conditions B); MS: 546 (M+1)$^+$

Example 163

8-[4-(1,1-Dioxido-thiomorpholin-4-ylmethyl)-3,5-difluoro-phenyl]-2-[4-methoxy-3-(4-methyl-piperazin-1-yl)-phenyl]-quinoxaline

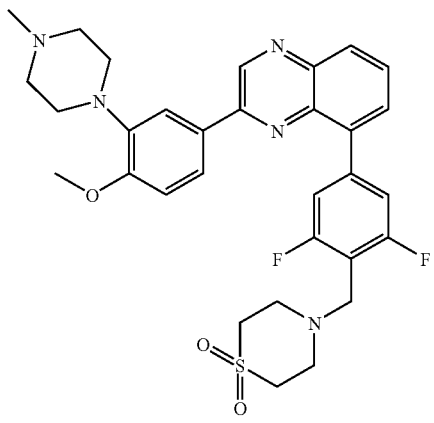

$R_t$=5.31 min (HPLC conditions B); MS: 594 (M+1)$^+$

Using the same synthetic methods as described in Example 1, but utilizing [3-(8-Bromo-quinoxalin-2-yl)-phenyl]-(4-methyl-piperazin-1-yl)-methanone [prepared analogously to step 1.5 but utilizing (4-Methyl-piperazin-1-yl)-[3-(4,4,5,5-tetramethyl-[1,3,2]dioxaborolan-2-yl)-phenyl]-methanone in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Examples

Example 164

{3-[8-(3,5-Difluoro-4-morpholin-4-ylmethyl-phenyl)-quinoxalin-2-yl]-phenyl}-(4-methyl-piperazin-1-yl)-methanone

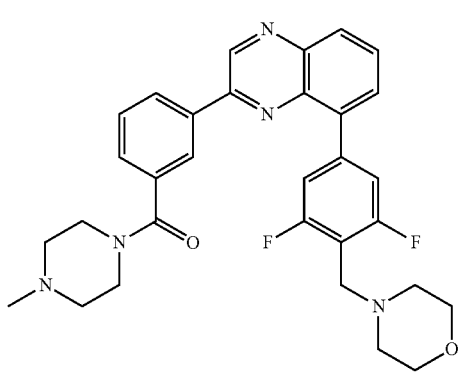

$R_t$=0.55 min (HPLC conditions A); MS: 544 (M+1)$^+$

Example 165

(3-{8-[4-(1,1-Dioxido-thiomorpholin-4-ylmethyl)-phenyl]-quinoxalin-2-yl}-phenyl)-(4-methyl-piperazin-1-yl)-methanone

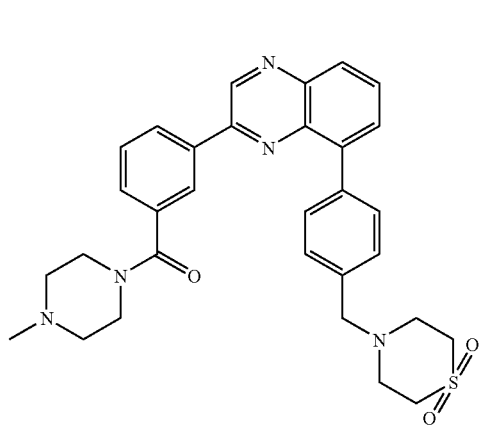

$R_t$=0.72 min (HPLC conditions A); MS: 556 (M+1)$^+$

Example 166

(3-{8-[4-(1,1-Dioxido-thiomorpholin-4-ylmethyl)-3,5-difluoro-phenyl]-quinoxalin-2-yl}-phenyl)-(4-methyl-piperazin-1-yl)-methanone

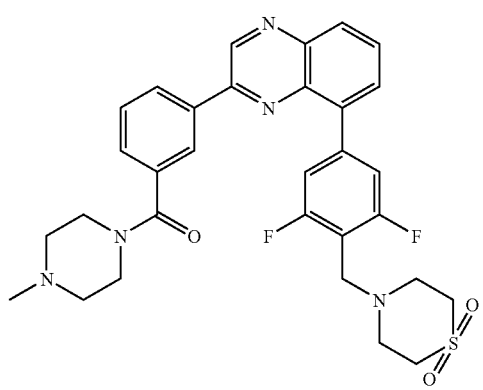

$R_t$=0.87 min (HPLC conditions A); MS: 592 (M+1)$^+$

Using the same synthetic methods as described in Example 1, but utilizing [4-(8-Bromo-quinoxalin-2-yl)-1-methyl-1H-pyrrol-2-yl]-(4-methyl-piperazin-1-yl)-methanone [prepared analogously to step 1.5 but utilizing (4-Methyl-piperazin-1-yl)-[1-methyl-4-(4,4,5,5-tetramethyl-[1,3,2]dioxaborolan-2-yl)-1H-pyrrol-2-yl]-methanone in lieu of 3,4,5-trimethoxyphenylboronic acid] in lieu of 8-Bromo-2-

(3,4,5-trimethoxy-phenyl)-quinoxaline and the appropriate boronic acid or ester derivative leads to the following Examples

Example 167

{4-[8-(3,5-Difluoro-4-morpholin-4-ylmethyl-phenyl)-quinoxalin-2-yl]-1-methyl-1H-pyrrol-2-yl}-(4-methyl-piperazin-1-yl)-methanone

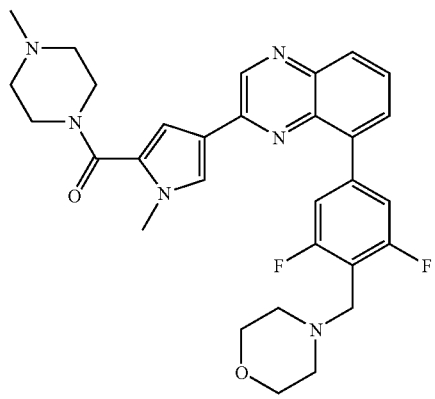

$R_t$=4.42 min (HPLC conditions B); MS: 547 (M+1)$^+$

Example 168

(4-{8-[4-(1,1-Dioxido-thiomorpholin-4-ylmethyl)-3,5-difluoro-phenyl]-quinoxalin-2-yl}-1-methyl-1H-pyrrol-2-yl)-(4-methyl-piperazin-1-yl)-methanone

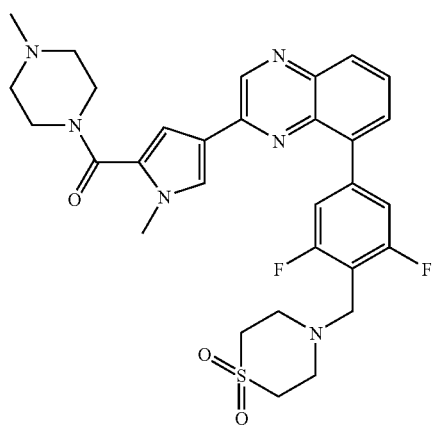

$R_t$=4.98 min (HPLC conditions B); MS: 595 (M+1)$^+$

Using the same synthetic methods as described in Example 1, but utilizing 4-[3-(8-Bromo-quinoxalin-2-yl)-phenyl]-piperazine-1-carboxylic acid tert-butyl este [prepared analogously to step 1.5 but utilizing 4-[3-(4,4,5,5-Tetramethyl-[1,3,2]dioxaborolan-2-yl)-phenyl]-piperazine-1-carboxylic acid tert-butyl ester in lieu of 3,4,5-trimethoxyphenylboronic acid] in lieu of 8-Bromo-2-(3,4,5-trimethoxy-phenyl)-quinoxaline and the appropriate boronic acid or ester derivative leads to the following Example

Example 169

8-[4-(1,1-Dioxido-thiomorpholin-4-ylmethyl)-3,5-difluoro-phenyl]-2-(3-piperazin-1-yl-phenyl)-quinoxaline

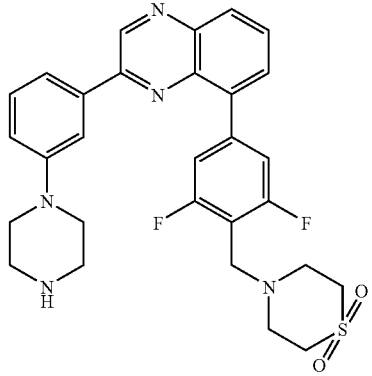

The title compound is obtained after deprotection of 4-(3-{8-[4-(1,1-Dioxido-thiomorpholin-4-ylmethyl)-3,5-difluoro-phenyl]-quinoxalin-2-yl}-phenyl)-piperazine-1-carboxylic acid tert-butyl ester with TFA in CH$_2$Cl$_2$ at RT.
$R_t$=0.95 min (HPLC conditions A); MS: 550 (M+1)$^+$

Example 170

8-[4-(1,1-Dioxido-thiomorpholin-4-ylmethyl)-3,5-difluoro-phenyl]-2-[3-(4-methyl-piperazin-1-yl)-phenyl]-quinoxaline

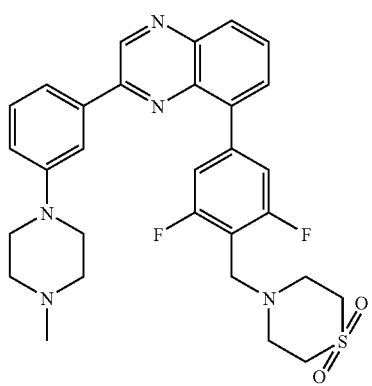

A solution of 8-[4-(1,1-Dioxido-thiomorpholin-4-ylmethyl)-3,5-difluoro-phenyl]-2-(3-piperazin-1-yl-phenyl)-quinoxaline (as obtained in example 169, 79 mg, 0.137 mmol) in MeOH (3 ml) and CH$_2$Cl$_2$ (1.5 ml) is treated with HCHO (41 µl, 0.550 mmol, 37% in H$_2$O/MeOH 9:1) and NaBH$_3$CN (35 mg, 0.546 mmol) at RT for 2 h. The reaction mixture is concentrated under reduced pressure. The residue is purified by reverse phase prep-HPLC (Waters) to afford the title compound as a yellow solid.
$R_t$=0.94 min (HPLC conditions A); MS: 564 (M+1)$^+$

Example 171

4-{8-[4-(1,1-Dioxido-thiomorpholin-4-ylmethyl)-3,5-difluoro-phenyl]-quinoxalin-2-yl}-2-methyl-but-3-yn-2-ol

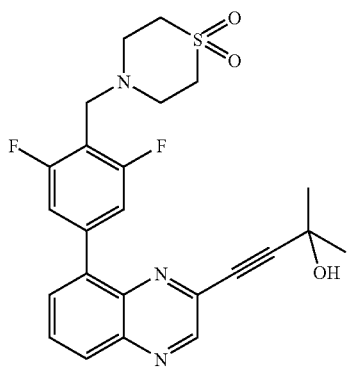

The title compound is prepared using the same synthetic methods as described in Example 1, but utilizing 4-(8-Bromo-quinoxalin-2-yl)-2-methyl-but-3-yn-2-ol (as obtained in step 171.1) in lieu of 8-Bromo-2-(3,4,5-trimethoxy-phenyl)-quinoxaline and the appropriate boronic acid or ester.

$R_f$=0.945 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 472 (M+1)$^+$

Step 171.1

4-(8-Bromo-quinoxalin-2-yl)-2-methyl-but-3-yn-2-ol

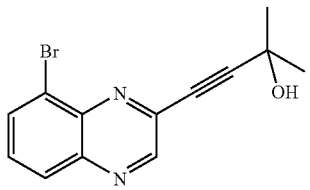

A microwave tube is charged with 200 mg (0.821 mmol) of 8-Bromo-2-chloro-quinoxaline, 159 µl (1.64 mmol) of 2-Methyl-but-3-yn-2-ol, 231 µl (1.64 mmol) of Et$_3$N, 6.26 mg (0.0329 mmol) of CuI and 11.8 mg (0.0164 mmol) of Pd(PPh$_3$)$_2$Cl$_2$. After several cycles of vacuum/purge with argon, 5 ml of n-BuOH are added. The reaction mixture is then stirred at RT for 30 min. The reaction mixture is poured onto a solution of NaHCO$_3$ and diluted with EtOAc and the phases are separated. The organic phase is washed several times with de-ionized water and the aqueous layer re-extracted with EtOAc. The combined organic layers are washed with brine, dried over Na$_2$SO$_4$, filtered and the filtrate is concentrated in vacuo. The residue is dissolved in CH$_2$Cl$_2$ and purified by chromatography (silicagel, hexane:EtOAc=1:1) to afford the title compound as a brown oil, $R_f$=1.026 min (Acquity HPLC BEH C18, 2.1×50 mm, 1.7 micron, detection 215 nM, 0.1 min 2% CH$_3$CN in H$_2$O, 2% to 100% CH$_3$CN in H$_2$O in 1.5 min, 0.4 min 100% CH$_3$CN+0.1% TFA, flow rate 1.0 ml/min); MS: 291 (M+1, $^{79}$Br)$^+$.

Example 172

Further Example compounds can be obtained in accordance with the procedures described herein by substitution at the 2-position of 8-bromo-2-chloro-quinoxaline by one of the following boronic acid or ester derivatives:

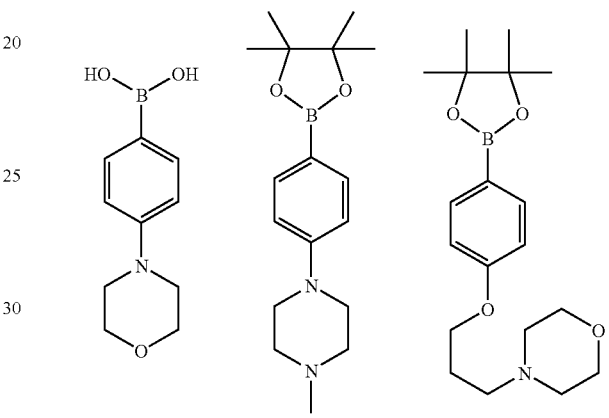

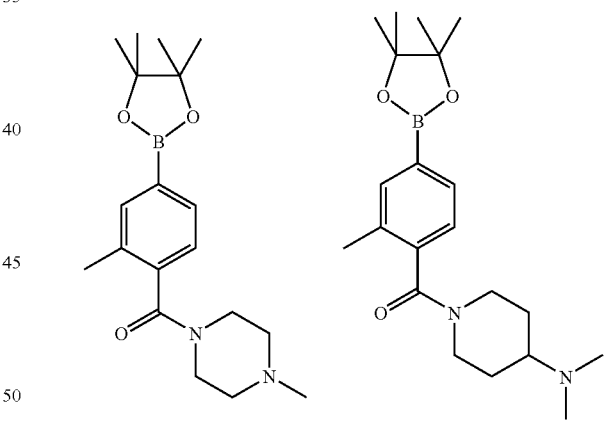

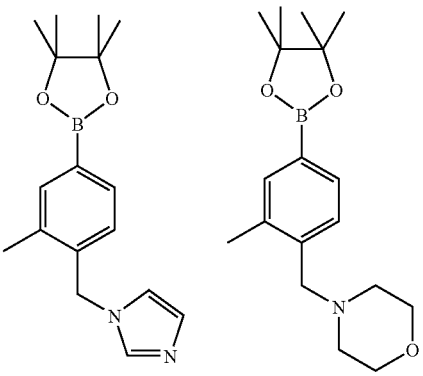

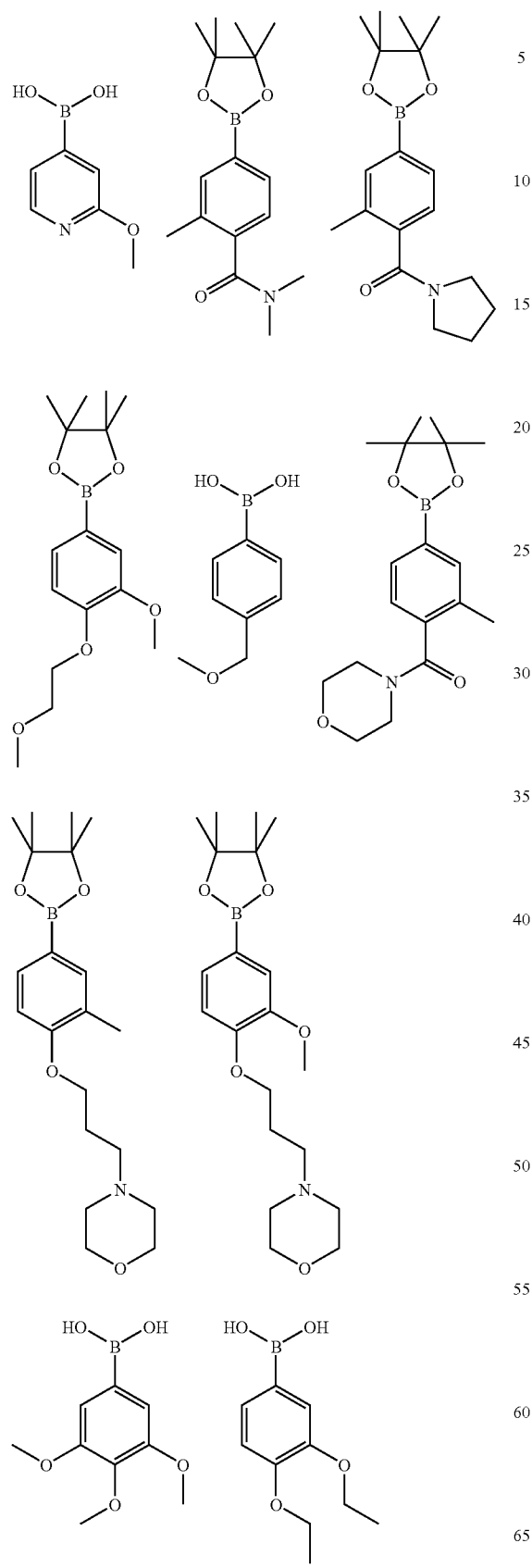
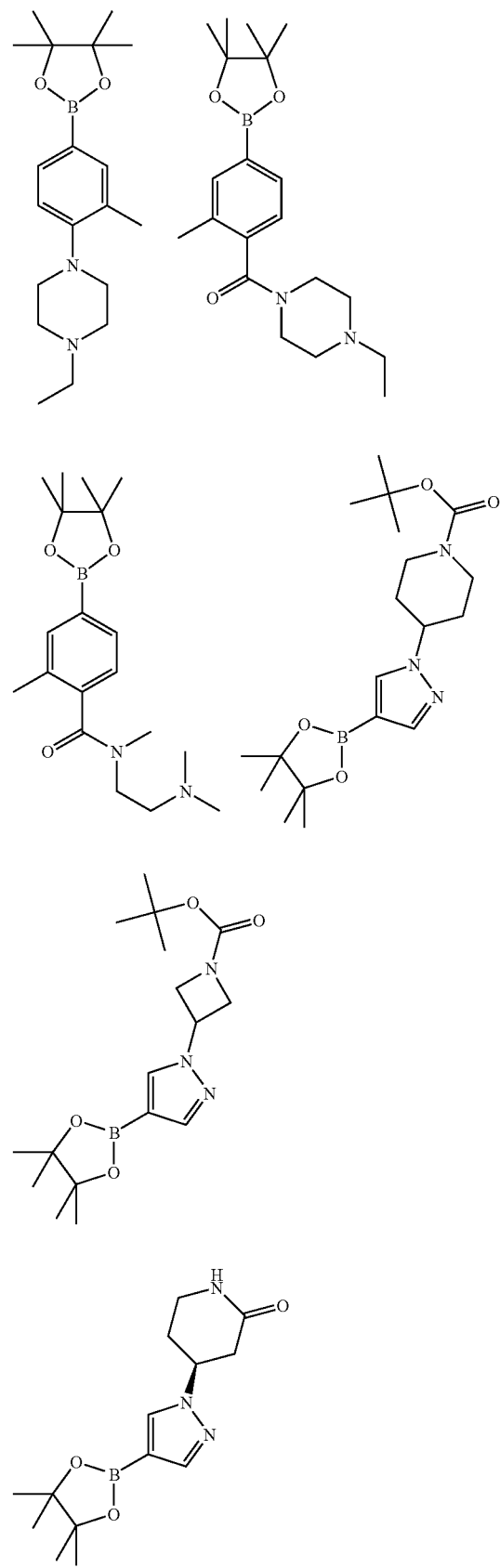

159
-continued
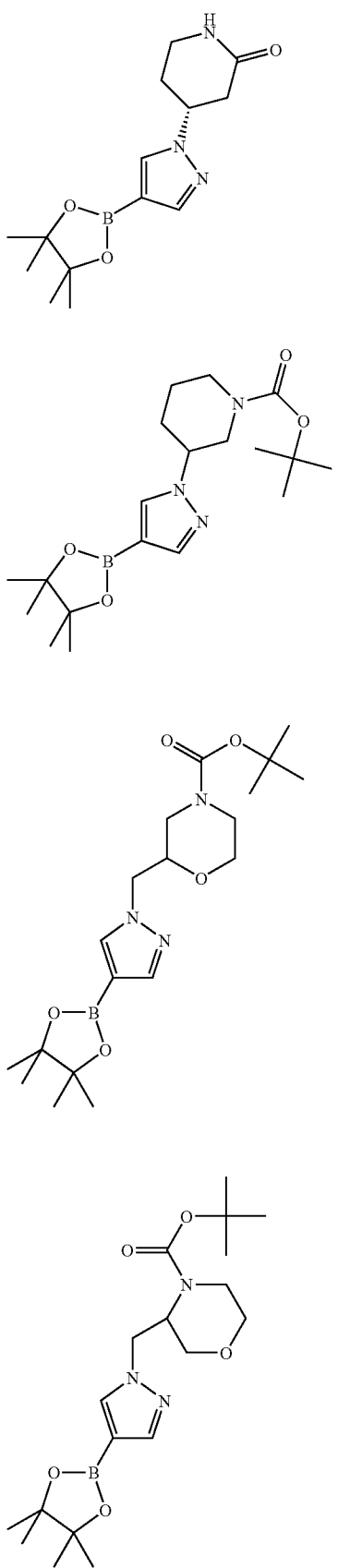
160
-continued
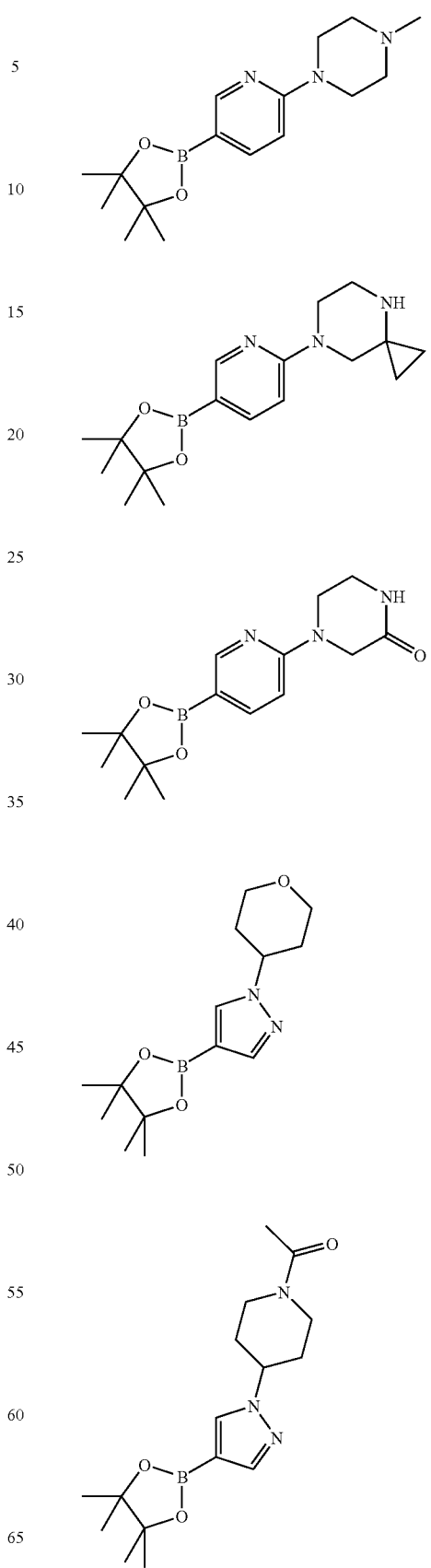

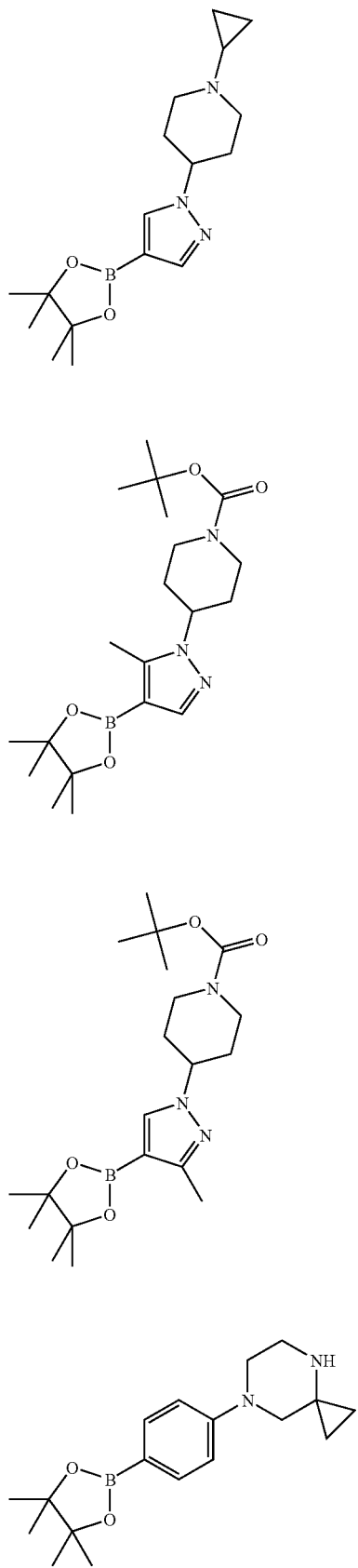
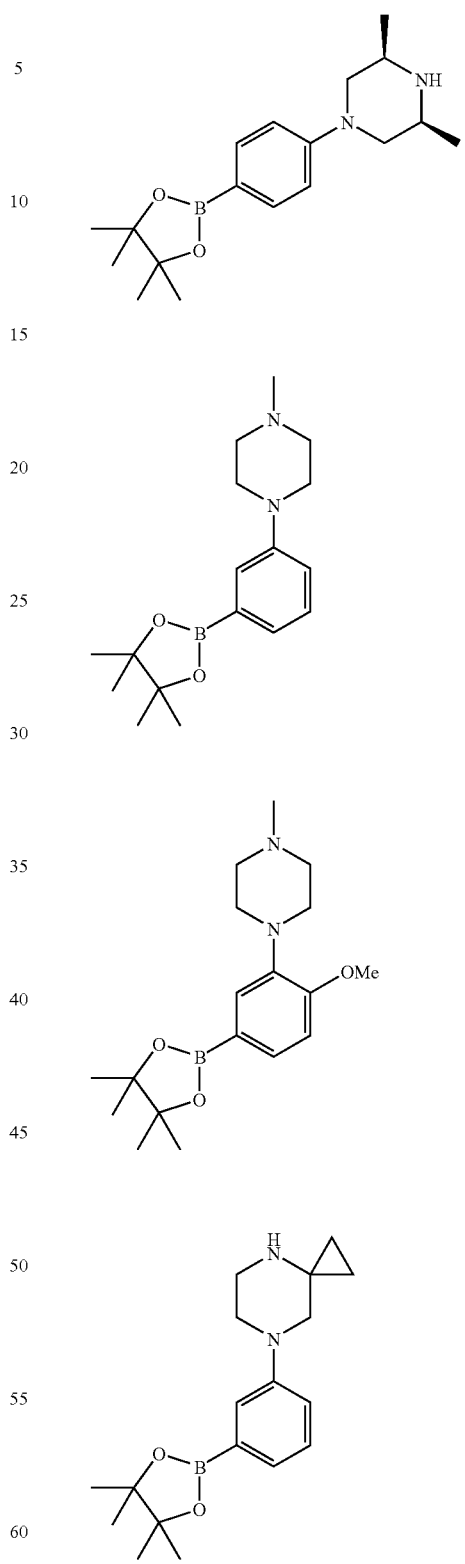
followed by substitution at the 8-position by one of the following boronic acid or ester derivatives:

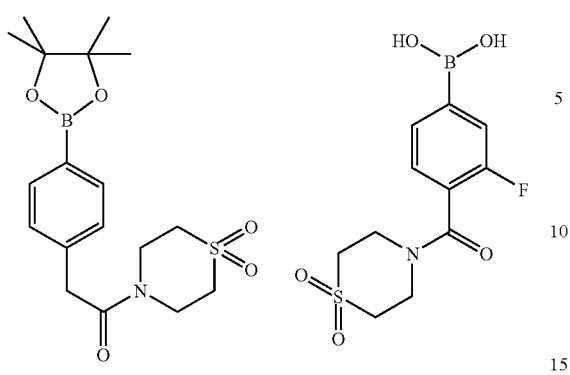
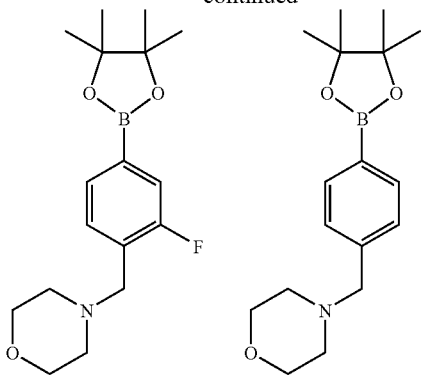
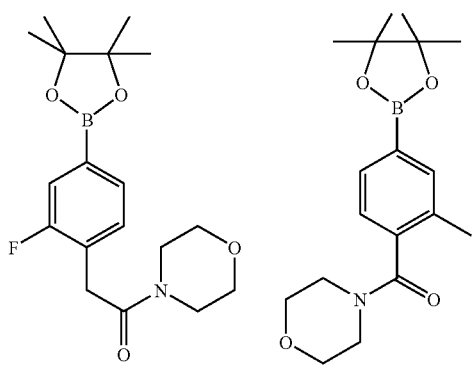
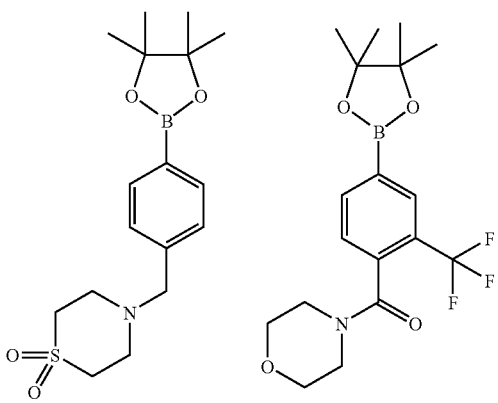
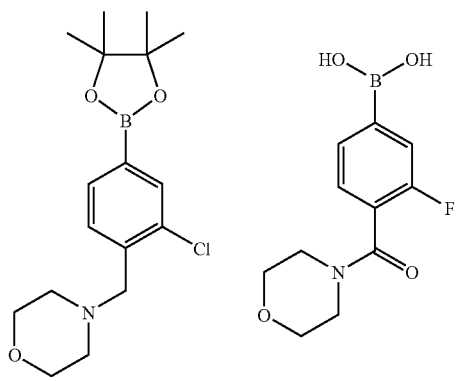
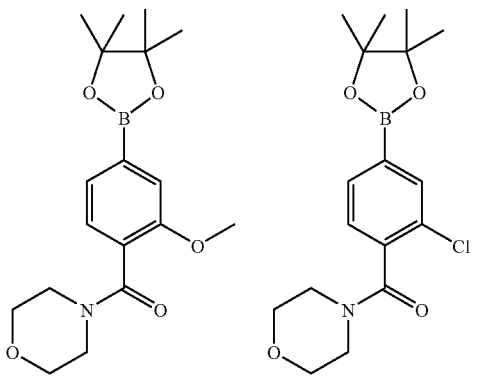
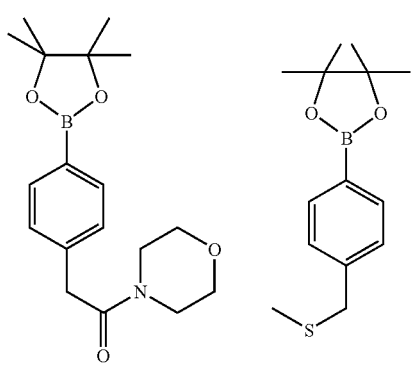
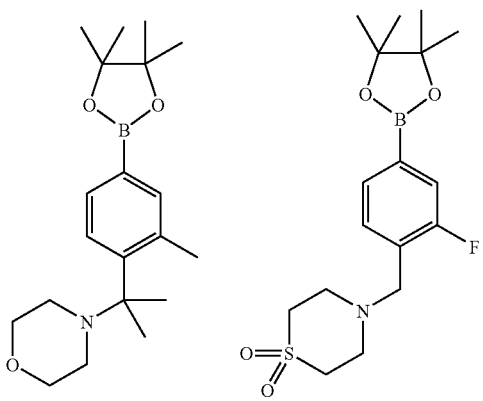

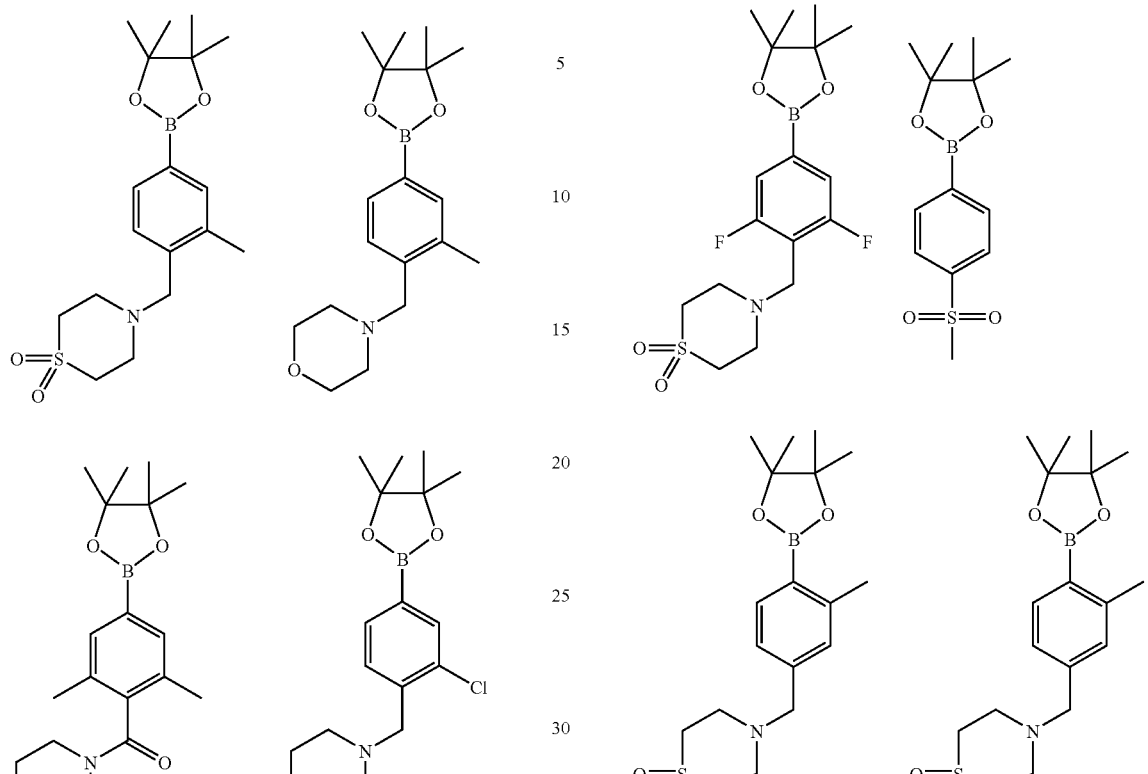

Example 173

EPK JAK-Family Kinases Profiling Assays

The efficacy of the compounds of the invention as inhibitors of JAK-family kinases: JAK1-3 and TYK kinase activity can be demonstrated as follows:

All four kinases of the JAK-family kinases were used as purified recombinant GST-fusion proteins, containing the active kinase domains. GST-JAK1(866-1154), GST-JAK3 (811-1124), and GST-TYK2(888-1187) were expressed and purified by affinity chromatography at the EPK biology unit. GST-JAK2(808-1132) was purchased from Invitrogen (Carlsbad, USA, #4288).

The kinase assays were based on the Caliper mobility shift assay using the LabChip 3000 systems. This technology is similar to capillary electrophoresis and uses charge driven separation of substrate and product in a microfluidic chip.

All kinase reactions were performed in 384 well microtiter plates in a total reaction volume of 18 μl. The assay plates were prepared with 0.1 μl per well of test compound in the appropriate test concentration, as described under the section "preparation of compound dilutions". The reactions were started by combining 9 μl of substrate mix (consisting of peptide and ATP) with 9 μl of kinase dilution. The reactions were incubated for 60 minutes at 30° C. and stopped by adding 70 μl of stop buffer (100 mM Hepes, 5% DMSO, 0.1% Coating reagent, 10 mM EDTA, 0.015% Brij 35).

Fluorescently labeled synthetic peptides were used as substrates in all reactions. A peptide derived from the sequence of IRS-1 (IRS-1 peptide, FITC-Ahx-KKSRGDYMTMQIG-NH2 (SEQ ID NO: 1)) was used for JAK1 and TYK2 and a peptide named JAK3tide (FITC-GGEEEEYFELVKKKK-NH2 (SEQ ID NO: 2)) for JAK2 and JAK3. Specific assay conditions are described in Table 1:

TABLE 1

Assay conditions of individual kinase assays

| Kinase | JAK1 | JAK2 | JAK3 | TYK2 |
| --- | --- | --- | --- | --- |
| Buffer | 50 mM Hepes pH 7.5, 0.02% Tween 20, 1 mM DTT, 0.02% BSA, 12 mM MgCl2 | 50 mM Hepes pH 7.5, 0.02% Tween 20, 1 mM DTT, 0.02% BSA, 9 mM MgCl2 | 50 mM Hepes pH 7.5, 0.02% Tween 20, 1 mM DTT, 0.02% BSA, 1.5 mM MgCl$_2$ | 50 mM Hepes pH 7.5, 0.02% Tween 20, 1 mM DTT, 0.02% BSA, 9 mM MgCl2 |
| DMSO | 0.6% | 0.6% | 0.6% | 0.6% |
| Kinase conc. | 50 nM | 1.8 nM | 6 nM | 40 nM |
| Substrate peptide conc. | 5 μM | 2 μM | 2 μM | 5 μM |
| ATP conc. | 40 μM | 20 μM | 80 μM | 30 μM |

The terminated reactions were transferred to the Caliper LabChip 3000 reader and the turnover of each reaction was measured by determining the substrate/product ratio.

Preparation of Compound Dilutions

Test compounds were dissolved in DMSO (10 mM) and transferred into 1.4 mL flat bottom or V-shaped Matrix tubes carrying a unique 2D matrix chip by individual compound hubs. The numbers of these chips were distinctively linked to the individual compound identification numbers. The stock solutions were stored at −20° C. if not used immediately. For the test procedure the vials were defrosted and identified by a scanner whereby a working sheet was generated that guided the subsequent working steps.

Compound dilutions were made in 96 well plates. This format enabled the assay of maximally 40 individual test compounds at 8 concentrations (single points) including 4 reference compounds. The dilution protocol included the production of pre-dilution plates, master plates and assay plates:

Pre-dilution plates: 96 polypropylene well plates were used as pre-dilution plates. A total of 4 pre-dilution plates were prepared including 10 test compounds each on the plate positions A1-A10, one standard compound at A11 and one DMSO control at A12. All dilution steps were done on a HamiltonSTAR robot.

Master plates: 100 μL of individual compound dilutions including standard compound and controls of the 4 "pre-dilution plates" were transferred into a 384 "master plate" including the following concentrations 1'820, 564, 182, 54.6, 18.2, 5.46, 1.82 and 0.546 μM, respectively in 90% of DMSO.

Assay plates: Identical assay plates were then prepared by pipetting 100 nL each of compound dilutions of the master plates into 384-well "assay plates". In the following the compounds were mixed with 9 μL of assays components plus 9 μL enzyme corresponding to a 1:181 dilution steps enabling the final concentration of 10, 3.0, 1.0, 0.3, 0.1, 0.03, 0.01 and 0.003 μM, respectively. The preparation of the master plates were handled by the Matrix PlateMate Plus robot and replication of assay plates by the HummingBird robot.

IC$_{50}$ values in the range of from about 3 nM to about 10 μM, e.g. from about 3 nM to about 5 μM, can be found with compounds of the invention according to formula (I).

Exemplified compounds show inhibitory activities with respect to the JAK family kinases with IC$_{50}$ values shown in Table 2.

On the basis of these studies, a compound of the invention may be used with therapeutic efficacy especially against disorders dependent on protein kinase, especially proliferative diseases mediated by JAK-family kinase activity.

Example 174

Inhibition of the JAK/STAT Pathway

The activity of the compounds of the invention as inhibitors of the JAK/STAT pathway can be demonstrated as follows:

The medium-throughput (96-well format), robust and reproducible cellular assay can be routinely used to assess the functional activation of Janus Kinases (JAKs), based on the nuclear translocation of their substrate, Signal Transducer and Activator of Transcription (STAT). Nuclear translocation can be monitored in HT1080 fibrosarcoma cells stably transfected with STAT1 fused to Green Fluorescence Protein (GFP). Stimulation with interferon-γ (IFN-γ) results in JAK1/JAK2-dependent nuclear translocation of STAT1-GFP that can be quantified using the Cellomics Cyto/NucTrans software package. This assay may be used to provide an assessment of the nuclear-cytoplasmic differential (NCD) of GFP-STAT1 using Hoechst dye to define the boundaries of the nucleus.

Cloning of STAT1 into pEGFP-N2:

STAT1 cDNA (GenBank Accession No. NM_007315) can be cloned in-frame with the Green Fluorescence Protein in pEGFP-N2 (Genebank Accession No. U57608, Clontech Cat. No. 6081-1) to obtain the final plasmid pEGFP-N2 STAT1 with an in/frame fusion of GFP at the carboxy-terminus of STAT1.

Generation of HT1080 Fibrosarcoma Cells Stably Expressing GFP-STAT1:

HT1080 fibrosarcoma cells may be obtained from ATCC (Cat. No. CCL-121) and can be cultured in alpha Modified Eagle Medium (Gibco Cat. No. 41061-029) with 10% FCS (Fetalclone II, Gibco, Cat. No. SH60066.03). Cells can be transfected with pEGFP-N2 STAT1 using Fugene 6 Transfection Reagent (Roche Diagnostics, Cat. No. 1 815 091) following the manufacturers protocol (3 µl of Fugene: 1 µg of DNA). 24 hours after transfection the medium can be replaced and selected in 1 mg/ml Geneticin (Gibco, Cat. No. 1031-019).

Preparation of Compound Stocks:

Compounds can be dissolved in DMSO to a final stock concentration of 10 mM and stored as aliquots at 4° C. Compounds may be pre-diluted in 100% DMSO at 10 mM, 3 mM 1 mM, 0.3 mM, 0.1 mM, 0.03 mM, 0.01 mM and 0.003 mM. Subsequently, compounds may be diluted in medium and added in 50 µl to the cells. The final compound concentrations tested may be 10 µM, 3 µM 1 µM, 0.3 µM, 0.1 µM, 0.03 µM, 0.01 µM and 0.003 µM and the final DMSO concentration can be 0.1%.

Cellomics Analysis of Nuclear Translocation of STAT-1-GFP Cell Stimulation and Staining for Cellomics Analysis:

HT1080 fibrosarcoma cells may be cultured in alpha Modified Eagle Medium (Gibco Cat. No. 41061-029) with 10% FCS (Fetalclone II, Gibco, Cat. No. SH60066.03), and 400 µg/ml G418 (Gibco, Cat. No. 10131-027).

HT1080 STAT1-GFP cells may be plated at a density of 10,000 cells per well in clear-bottom black 96-well Packard View-Plates™ (Cat. No. 6005182). 16-24 hours later, the cells can be treated for 2 hours with 100 ng/ml IFN-γ (R&D Systems Cat. No. 285-IF), washed twice in pre-warmed PBS and fixed in 200 µl of pre-warmed fixation solution (PBS, 3.7% Formaldehyde (Sigma, Cat. No. F-1635)) for 10 minutes. The plates may be washed twice in 200 µl PBS and incubated, protected from light, in 100 µl of DNA-staining solution (PBS, 0.5 µg/ml Hoechst-33342 (Sigma, Cat. No. B-2261)) for 1 minute. The plates may then be washed once in PBS, and 200 µl PBS finally added per well. The plates, being finally covered with a black adhesive, may be either read directly or stored at 4° C. for later imaging. Where appropriate, the compounds may be added 30 min before stimulation with IFN-γ.

STAT1-GFP Nuclear Translocation Measurement by Cellomics Automated Fluorescence Microcopy Imaging and Analysis:

The plates can be read on a Cellomics® ArrayscanII automated fluorescence microscope plate reader equipped with a Mercury-Xenon white light illumination source and a Zeiss Axiovert inverted microscope, using the XF100 dichroic/emission filter cube and matching excitation filters, 10× magnification, and a 0.3 numerical aperture objective. Image acquisition and analysis can be performed using a customized protocol based on the 'NuclearTranslocation' Bioapplication (for details, see Appendices). For each well, multiple images (fields) can be acquired until a minimum of 1000 cells are counted using two 2 channels: Channel 1 (Hoechst)=focus+ nuclear mask, Channel 2 (GFP)=signal quantification in mask areas as outlined below.

Nuclei may be first identified based on the Hoechst staining and a mask generated for each nucleus that then serves as a template to generate a circle (eroded inwards by 1 pixel) and a 3 pixel-wide collar-like ring (off-set outwards by 1 pixel), in which the nuclear and cytoplasmic intensity of GFP, respectively, are quantified in the corresponding channel. High content analysis yields numerous measurements per cell and the GPF intensity differential between the nuclear and the cytoplasmic masks may be chosen as a measure of sub-cellular GFP-STAT1 relocation. The resulting values may be averaged for all cells in the well to return a single measurement plus standard deviation.

To generate $IC_{50}$ values, the nuclear-cytoplasmic GFP-STAT1 differential of untreated cells may be used as a baseline and the following equation used to determine the percentage increase in nuclear translocation:

Percentage=100*(NCD Compound pre-treated INF-γ-stimulated−NCD Untreated)/(NCD DMSO-pre-treated IFN-γ stimulated−NCD Untreated).

TABLE 2

JAK1-3 and TYK kinase inhibitory activities and JAK/STAT pathway inhibitory activities

| Ex n° | JAK1 $IC_{50}$ [umol l$^{-1}$] | JAK $IC_{50}$ [umol l$^{-1}$] | JAK3 $IC_{50}$ [umol l$^{-1}$] | TYK2 $IC_{50}$ [umol l$^{-1}$] | STAT1translo $IC_{50}$ [umol l$^{-1}$] |
|---|---|---|---|---|---|
| 1 | N.D. | 0.082 | 4.4 | N.D. | N.D. |
| 2 | N.D. | 0.12 | 5.4 | N.D. | N.D. |
| 3 | N.D. | 0.085 | 9.4 | N.D. | 10.802 |
| 4 | N.D. | 0.22 | >10 | N.D. | N.D. |
| 5 | N.D. | 0.11 | >10 | N.D. | N.D. |
| 6 | N.D. | 0.067 | 4.5 | N.D. | 5.366 |
| 7 | N.D. | 0.095 | 8.422 | N.D. | N.D. |
| 8 | N.D. | 0.11 | >10 | N.D. | N.D. |
| 9 | N.D. | 0.17 | >10 | N.D. | N.D. |
| 10 | N.D. | 0.093 | >10 | N.D. | N.D. |
| 11 | 0.039 | 0.0090 | 0.81 | 0.26 | 0.7025 |
| 12 | 0.18 | 0.0525 | >10 | N.D. | N.D. |
| 13 | 0.027 | 0.0051 | 0.33 | 0.235 | 0.47 |
| 14 | N.D. | 0.08 | 4.3 | N.D. | 5.095 |
| 15 | N.D. | 0.081 | >10 | N.D. | N.D. |
| 16 | N.D. | 0.019 | 1.5 | N.D. | N.D. |
| 17 | N.D. | 0.013 | 1.3 | N.D. | 1.345 |
| 18 | 0.23 | 0.038 | 2.3 | N.D. | 0.3395 |
| 19 | 0.059 | 0.018 | 0.8 | N.D. | 1.84 |
| 20 | 0.16 | 0.024 | 1.2 | N.D. | 5.775 |
| 21 | 1.8 | 0.21 | 5.2 | N.D. | >10 |
| 22 | N.D. | 0.073 | >10 | N.D. | 8.195 |
| 23 | N.D. | 0.2 | >10 | N.D. | N.D. |
| 25 | N.D. | 0.042 | >10 | N.D. | >10 |
| 26 | N.D. | 0.022 | 0.7 | N.D. | 0.7725 |
| 27 | N.D. | 0.034 | 1.7 | N.D. | 0.198 |
| 28 | N.D. | 0.012 | >10 | N.D. | 2.18 |
| 29 | N.D. | 0.1 | >10 | N.D. | 11.35 |
| 30 | N.D. | 0.011 | 1.5 | N.D. | 3.805 |
| 31 | N.D. | 0.0073 | 1.1 | N.D. | 3.515 |
| 32 | 0.57 | 0.084 | 2.7 | N.D. | 7.788 |
| 33 | N.D. | 0.032 | 3.1 | N.D. | 9.885 |
| 34 | 0.027 | 0.0041 | 0.49 | 0.088 | 0.338 |
| 35 | 0.094 | 0.0119 | 1.863 | 0.52 | 1.72 |
| 36 | 0.041 | 0.017 | 0.94 | N.D. | 3.86 |

TABLE 2-continued

JAK1-3 and TYK kinase inhibitory activities and JAK/STAT pathway inhibitory activities

| Ex n° | JAK1 IC$_{50}$ [umol l$^{-1}$] | JAK IC$_{50}$ [umol l$^{-1}$] | JAK3 IC$_{50}$ [umol l$^{-1}$] | TYK2 IC$_{50}$ [umol l$^{-1}$] | STAT1translo IC$_{50}$ [umol l$^{-1}$] |
|---|---|---|---|---|---|
| 37 | 0.068 | 0.014 | 0.78 | N.D. | 3.075 |
| 38 | N.D. | 0.023 | 4.2 | N.D. | N.D. |
| 39 | N.D. | 0.19 | >10 | N.D. | N.D. |
| 40 | 0.0784 | 0.0073 | 0.627 | 0.29 | 0.160 |
| 41 | 0.13 | 0.0063 | 0.64 | N.D. | 0.3455 |
| 42 | 0.715 | 0.018 | 2.15 | 1.45 | 0.857 |
| 43 | 0.42 | 0.027 | 0.87 | 0.715 | 1.127 |
| 44 | 0.15 | 0.00655 | 0.405 | 0.24 | 0.049 |
| 45 | 0.19 | 0.03 | 2.2 | N.D. | 2.4015 |
| 46 | 0.11 | 0.02 | 1.6 | N.D. | 2.8155 |
| 47 | N.D. | 0.038 | >10 | N.D. | |
| 48 | 0.0099 | <0.003 | 0.077 | N.D. | 0.15 |
| 49 | 0.26 | 0.038 | 4.4 | N.D. | 1.225 |
| 50 | 0.038 | 0.00705 | >10 | 1.6 | 1.65 |
| 51 | 0.12 | 0.0315 | >10 | >10 | 2.045 |
| 52 | 0.0975 | 0.032 | 1.1 | 0.985 | 2.95 |
| 53 | 0.012 | <0.003 | 0.215 | 0.0935 | 0.15 |
| 54 | 0.017 | <0.003 | 0.065 | N.D. | 0.14 |
| 55 | 1.7 | 0.09 | 4.2 | N.D. | 3.144 |
| 56 | 0.15 | 0.012 | 0.57 | N.D. | 0.471 |
| 57 | 0.08 | <0.003 | 0.17 | N.D. | 0.163 |
| 58 | 0.09 | 0.011 | 0.32 | N.D. | 0.2205 |
| 59 | 0.52 | 0.02 | 1.95 | N.D. | 0.635 |
| 60 | 1.6 | 0.11 | 3.8 | N.D. | 4.75 |
| 61 | 0.165 | 0.015 | 1.4 | N.D. | 0.235 |
| 62 | 0.0445 | 0.0057 | 0.33 | N.D. | 0.082 |
| 63 | 0.37 | 0.0775 | 4.3 | 1.45 | 0.9865 |
| 64 | 0.068 | 0.00495 | 0.29 | 0.165 | 0.0465 |
| 65 | 0.24 | 0.0155 | 0.86 | N.D. | 2.185 |
| 66 | 0.14 | 0.00605 | 0.25 | N.D. | 1 |
| 67 | 0.0965 | <0.003 | 0.405 | N.D. | 0.475 |
| 68 | 2.3 | 0.109 | 6.85 | N.D. | 4.89 |
| 69 | 0.075 | 0.0067 | 0.89 | N.D. | 0.53 |
| 70 | 0.36 | 0.0305 | 1.75 | 1.35 | 0.5635 |
| 71 | 0.16 | 0.0081 | 0.79 | 0.51 | 2.4795 |
| 72 | 0.11 | 0.0057 | 0.67 | N.D. | 1.115 |
| 73 | 0.19 | 0.028 | 0.37 | N.D. | >10 |
| 74 | 0.31 | 0.025 | 1.3 | N.D. | 2.6095 |
| 75 | 0.41 | 0.034 | 1.7 | N.D. | >10 |
| 76 | 0.69 | 0.0595 | 4.1 | N.D. | 5.99 |
| 77 | N.D. | 0.13 | 9.8 | N.D. | |
| 78 | N.D. | 0.15 | >10 | N.D. | 9.69 |
| 79 | N.D. | 0.52 | >10 | N.D. | |
| 80 | 3.8 | 0.075 | 4.55 | N.D. | 1.549 |
| 81 | 1.15 | 0.0165 | 0.78 | N.D. | 0.389 |
| 82 | 0.49 | 0.014 | 1.25 | N.D. | 0.9455 |
| 83 | 0.0335 | 0.00625 | 0.89 | 0.27 | 2.08 |
| 84 | 0.0585 | 0.0055 | 0.975 | 0.27 | 1.46 |
| 85 | 0.0125 | 0.00325 | 0.22 | 0.115 | 0.24 |
| 86 | 0.00665 | <0.003 | 0.11 | 0.038 | 0.093 |
| 87 | 0.225 | 0.0335 | 3.5 | 0.72 | 1.32 |
| 88 | 0.027 | 0.00655 | 0.84 | 0.113 | 0.7 |
| 89 | 0.135 | 0.034 | 3.95 | 0.45 | 1.336 |
| 92 | 1.385 | 0.043 | 4.9 | 3.65 | 2.135 |
| 93 | 0.185 | 0.022 | 1.25 | 0.67 | 3.01 |
| 94 | 0.455 | 0.027 | 2.15 | 0.985 | 1.53 |
| 95 | 0.018 | <0.003 | 0.0735 | 0.04 | 0.105 |
| 96 | 0.053 | <0.003 | 0.26 | 0.0505 | 0.0355 |
| 97 | 0.72 | 0.0195 | 9.15 | 0.51 | 0.495 |
| 98 | 0.3898 | 0.011 | 5.4 | 0.5434 | 0.2025 |
| 99 | 0.87 | 0.022 | 4.85 | 0.805 | 1.36 |
| 100 | 1.4 | 0.13 | N.D. | 1.2 | 12.6 |
| 101 | 0.575 | 0.014 | 1.025 | 1.45 | N.D. |
| 102 | 1.216 | 0.074 | 5.333 | 2.7275 | 0.0315 |
| 103 | 1.15 | 0.0305 | 3.6 | 1.2 | 0.824 |
| 104 | 0.052 | <0.003 | 0.39 | 0.13 | 0.42 |
| 105 | 0.81 | 0.032 | 1.8 | 0.985 | 0.895 |
| 106 | 0.365 | 0.082 | 0.195 | 1.9725 | 0.2015 |
| 107 | 1.35 | 0.0955 | 9.8 | 2.95 | 2.4665 |
| 108 | 0.254 | 0.0245 | 2.4 | 0.417 | 0.15 |
| 109 | 0.15 | 0.024 | N.D. | 0.36 | 3.065 |
| 110 | 5.55 | 0.575 | >10 | 9.3 | 1.588 |
| 111 | 0.92 | 0.1045 | 9.3 | 1.7 | 1.232 |
| 112 | 5.35 | 0.32 | >10 | >10 | 13.6 |
| 113 | 0.615 | 0.0285 | 3.3 | 1.15 | 1.935 |
| 114 | 0.25 | 0.0115 | 1.65 | 0.345 | 6.385 |
| 115 | 0.0725 | 0.0093 | 1.6 | 0.48 | 1.44 |
| 116 | 0.243 | 0.008 | 2.9 | 0.437 | N.D. |
| 117 | 0.0765 | <0.003 | 1.035 | 0.125 | 0.06 |
| 118 | 0.47 | 0.025 | >10 | 0.955 | 0.36 |
| 119 | 0.25 | 0.00985 | 6.4 | 0.28 | 0.34 |
| 120 | 0.13 | 0.013 | N.D. | 0.35 | 1.73 |
| 121 | 0.2 | 0.0038 | N.D. | 0.23 | N.D. |
| 122 | 0.475 | 0.00935 | 3.25 | 0.54 | N.D. |
| 123 | 0.135 | 0.005 | 1.95 | 0.17 | 0.18 |
| 125 | 0.31 | <0.003 | N.D. | 0.21 | 0.369 |
| 127 | 0.066 | <0.003 | N.D. | 0.038 | 0.086 |
| 128 | 0.13 | <0.003 | N.D. | 0.16 | 0.196 |
| 129 | 0.078 | <0.003 | N.D. | 0.096 | 0.162 |
| 130 | 0.15 | 0.0034 | N.D. | 0.2 | 0.163 |
| 131 | 0.05 | <0.003 | N.D. | 0.033 | 0.09 |
| 133 | 0.55 | 0.0054 | N.D. | 0.75 | 0.84 |
| 135 | 0.24 | 0.0061 | N.D. | 0.51 | 1.35 |
| 136 | 0.29 | 0.0046 | N.D. | 0.26 | 0.532 |
| 144 | 0.96 | 0.025 | N.D. | 0.97 | 7.655 |
| 145 | 0.25 | 0.01 | N.D. | 0.3 | 0.685 |
| 146 | 0.84 | 0.0092 | N.D | 0.57 | 3.39 |
| 147 | 1.5 | 0.097 | N.D | 1 | N.D. |
| 148 | 0.073 | 0.0034 | N.D | 0.11 | 0.73 |
| 149 | 0.65 | 0.051 | N.D | 0.9 | 9.56 |
| 150 | 0.83 | 0.03 | N.D | 0.83 | 4.275 |
| 155 | 3.4 | 0.063 | N.D | 7.6 | N.D |
| 156 | >10 | 0.95 | N.D | >10 | N.D |
| 157 | 3.6 | 0.14 | N.D | 6.4 | N.D |
| 158 | >10 | 0.65 | N.D | >10 | N.D |
| 160 | 0.36 | 0.0064 | N.D | 0.4 | N.D |
| 161 | 0.11 | <0.003 | N.D | 0.48 | N.D |
| 162 | 0.069 | 0.0057 | N.D | 0.36 | N.D |
| 163 | 0.077 | <0.003 | N.D | 0.088 | N.D |
| 164 | 0.3 | 0.05 | N.D | 2 | N.D |
| 165 | 0.16 | 0.074 | N.D | 1.2 | N.D |
| 166 | 0.07 | 0.011 | N.D | 0.27 | N.D |
| 167 | 0.053 | 0.0081 | N.D | 0.18 | N.D |
| 168 | 0.016 | <0.003 | N.D | 0.03 | N.D |
| 169 | 0.017 | <0.003 | N.D | 0.026 | N.D |
| 170 | 0.021 | 0.004 | N.D | 0.14 | 0.296 |
| 171 | 0.44 | 0.07 | N.D | 2 | N.D |

N.D. = not determined.

Example 175

Soft Capsules 5000 soft gelatin capsules, each comprising as active ingredient 0.05 g of one of the compounds of formula I mentioned in the preceding Examples, are prepared as follows: 250 g pulverized active ingredient is suspended in 2 L Lauroglykol® (propylene glycol laurate, Gattefossé S.A., Saint Priest, France) and ground in a wet pulverizer. 0.419 g portions of the mixture are then introduced into soft gelatin capsules using a capsule-filling machine.

The invention claimed is:

1. A compound of formula (II)

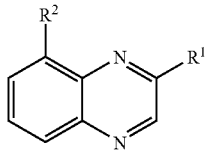

wherein
$R^1$ is aryl or heteroaryl, either of which is substituted with 1, 2 or 3 $R^7$;
$R^2$ is phenyl substituted with 1, 2 or 3 $R^8$;
wherein each $R^7$ is —W—$R^{10}$, wherein:
W is a bond or a linker comprising 1 to 20 in-chain atoms, comprising one or more linkages selected from —O—, —C(O)—, —S(O)$_1$—, —N($R^{11}$)—, hydrocarbylene optionally substituted with 1, 2, 3, 4 or 5 $R^{13}$, and heterocyclylene optionally substituted with 1, 2, 3, 4 or 5 $R^{13}$;
$R^{10}$ is selected from hydrogen, except when W is a bond; hydrocarbyl optionally substituted with 1, 2, 3, 4 or 5 $R^{13}$; and —(CH$_2$)$_k$-heterocyclyl optionally substituted with 1, 2, 3, 4 or 5 $R^{13}$;
$R^{11}$ is selected from $R^{12}$, —O$R^{12}$, —C(O)$R^{12}$, —C(O)O$R^{12}$ and —S(O)$_l R^{12}$;
$R^{12}$ is selected from hydrogen; hydrocarbyl optionally substituted with 1, 2, 3, 4 or 5 $R^{13}$; and —(CH$_2$)$_k$-heterocyclyl optionally substituted with 1, 2, 3, 4 or 5 $R^{13}$;
$R^{13}$ is selected from $R^{14}$; hydrocarbyl optionally substituted with 1, 2, 3, 4 or 5 $R^{14}$; and —(CH$_2$)$_k$-heterocyclyl optionally substituted with 1, 2, 3, 4 or 5 $R^{14}$;
$R^{14}$ is independently selected from halogen, trifluoromethyl, cyano, nitro, oxo, =N$R^{15}$, —O$R^{15}$, —C(O)$R^{15}$, —C(O)N($R^{15}$)$R^{16}$, —C(O)O$R^{15}$, —OC(O)$R^{15}$, —C(N$R^{15}$)N($R^{15}$)$R^{16}$, —S(O)$_l R^{15}$, —S(O)$_1$N($R^{15}$) $R^{16}$, —N($R^{15}$)$R^{16}$, —N($R^{15}$)N($R^{15}$)$R^{16}$, —N($R^{15}$)C(O)$R^{16}$ and —N($R^{15}$)S(O)$_l R^{16}$;
$R^{15}$ and $R^{16}$ are each independently hydrogen or selected from hydrocarbyl and —(CH$_2$)$_k$-heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy;
k is 0, 1, 2, 3, 4, 5 or 6; and
l is 0, 1, or 2, and wherein,
at least one $R^8$ is Y—$R^{17}$, wherein,
Y is a bond or a linker comprising 1, 2, 3 or 4 linkages independently selected from —O—, —C(O)—, —S(O)$_1$—, —N($R^{11}$)— and $C_{1-6}$ alkylene optionally substituted with 1, 2, 3, 4 or 5 $R^{13}$, and
$R^{17}$ is heterocyclyl optionally substituted with 1, 2, 3, 4 or 5 $R^{13}$,
and wherein $R^2$ optionally comprises one or more further $R^8$ substituents wherein said further $R^8$ are each independently selected from, $C_{1-6}$ alkyl, $C_{1-6}$ alkoxy and halogen, or a pharmaceutically acceptable salt thereof.

2. A compound of formula (II) according to claim 1 wherein $R^{10}$ is hydrocarbyl, optionally substituted with 1, 2, 3, 4 or 5 $R^{13}$ or $R^{10}$ is heterocyclyl optionally substituted with 1, 2, 3, 4 or 5 $R^{13}$; or a pharmaceutically acceptable salt thereof.

3. A compound of formula (II) according to claim 2, wherein $R^{10}$ is $C_{1-6}$ alkyl, optionally substituted with 1, 2, 3, 4 or 5 $R^{13}$ or piperidyl, piperazinyl or morpholinyl, optionally substituted with 1, 2, 3, 4 or 5 $R^{13}$; or a pharmaceutically acceptable salt thereof.

4. A compound of formula (II) as defined in claim 1, wherein $R^1$ is phenyl, pyridinyl or pyrazolyl; or a pharmaceutically acceptable salt thereof.

5. A compound of formula (II) according to claim 1, wherein $R^1$ is substituted with 1, 2 or 3 $R^7$, wherein at least one $R^7$ is selected from hydroxy,
$C_{1-6}$ alkyl optionally substituted with 1, 2, 3, 4 or 5 $R^{13}$,
$C_{1-6}$ alkoxy optionally substituted with 1, 2, 3, 4 or 5 $R^{13}$,
$C_{1-6}$ alkoxyalkyl optionally substituted with 1, 2, 3, 4 or 5 $R^{13}$,
—S(O)$_l R^{15}$,
—S(O)$_1$N($R^{15}$)$R^{16}$ and
—N($R^{15}$)S(O)$_l R^{16}$,
wherein $R^{15}$ and $R^{16}$ are each hydrogen or $C_{1-6}$ alkyl optionally substituted with 1, 2, 3, 4 or 5 $R^{13}$; or a pharmaceutically acceptable salt thereof.

6. A compound of formula (II) according claim 1 wherein Y is selected from —C(O)—, —$C_{1-6}$ alkylene-, —C(O)—$C_{1-6}$ alkylene- and —$C_{1-6}$ alkylene-C(O)—, wherein the $C_{1-6}$ alkylene moieties are optionally substituted with 1, 2, 3, 4 or 5 $R^{13}$; or a pharmaceutically acceptable salt thereof.

7. A compound of formula (II) according to claim 1 wherein $R^{17}$ is morpholinyl, thiomorpholinyl or piperazinyl, optionally substituted with 1, 2, 3, 4 or 5 $R^{13}$; or a pharmaceutically acceptable salt thereof.

8. A compound of formula (II) as defined in claim 1, wherein the compound is of the formula (IV):

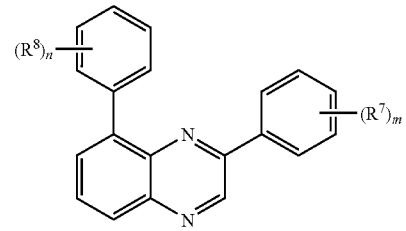

wherein m and n are each independently 1, 2, or 3; or a pharmaceutically acceptable salt thereof.

9. A pharmaceutical formulation comprising a compound of formula (II) as defined in claim 1, or a pharmaceutically acceptable salt thereof and a pharmaceutically acceptable carrier or excipient.

10. A compound selected from:
{3-Fluoro-4-[3-(3,4,5-trimethoxy-phenyl)-quinoxalin-5-yl]-phenyl}-morpholin-4-yl-methanone,
8-(4-Methanesulfonyl-phenyl)-2-(3,4,5-trimethoxy-phenyl)-quinoxaline,
8-(4-Ethanesulfonyl-phenyl)-2-(3,4,5-trimethoxy-phenyl)-quinoxaline,
8-[4-(Propane-2-sulfonyl)-phenyl]-2-(3,4,5-trimethoxy-phenyl)-quinoxaline,
4-[3-(3,4,5-Trimethoxy-phenyl)-quinoxalin-5-yl]-benzenesulfonamide,
N-Methyl-4-[3-(3,4,5-trimethoxy-phenyl)-quinoxalin-5-yl]-benzenesulfonamide,
N-Ethyl-4-[3-(3,4,5-trimethoxy-phenyl)-quinoxalin-5-yl]-benzenesulfonamide,
N,N-Dimethyl-4-[3-(3,4,5-trimethoxy-phenyl)-quinoxalin-5-yl]-benzenesulfonamide, N-Methyl-4-[3-(3,4,5-trimethoxy-phenyl)-quinoxalin-5-yl]-benzamide,
Morpholin-4-yl-{4-[3-(3,4,5-trimethoxy-phenyl)-quinoxalin-5-yl]-phenyl}-methanone,
1-Morpholin-4-yl-2-{4-[3-(3,4,5-trimethoxy-phenyl)-quinoxalin-5-yl]-phenyl}-ethanone,
N-{4-[3-(3,4,5-Trimethoxy-phenyl)-quinoxalin-5-yl]-phenyl}-methanesulfonamide,
1-(1,1-Dioxido-thiomorpholin-4-yl)-2-{4-[3-(3,4,5-trimethoxy-phenyl)-quinoxalin-5-yl]-phenyl}-ethanone,
1-(4-Methyl-piperazin-1-yl)-2-{4-[3-(3,4,5-trimethoxy-phenyl)-quinoxalin-5-yl]-phenyl}-ethanone,
8-(4-Morpholin-4-ylmethyl-phenyl)-2-(3,4,5-trimethoxy-phenyl)-quinoxaline,
{2-Methyl-4-[3-(3,4,5-trimethoxy-phenyl)-quinoxalin-5-yl]-phenyl}-morpholin-4-yl-methanone,
2-Fluoro-4-[3-(3,4,5-trimethoxy-phenyl)-quinoxalin-5-yl]-phenyl}-morpholin-4-yl-methanone,
{2-Chloro-4-[3-(3,4,5-trimethoxy-phenyl)-quinoxalin-5-yl]-phenyl}-morpholin-4-yl-methanone,
8-[4-(1,1-Dioxido-thiomorpholin-4-ylmethyl)-phenyl]-2-(3,4,5-trimethoxy-phenyl)-quinoxaline,
8-(3-Fluoro-4-morpholin-4-ylmethyl-phenyl)-2-(3,4,5-trimethoxy-phenyl)-quinoxaline,
8-(3-Methyl-4-morpholin-4-ylmethyl-phenyl)-2-(3,4,5-trimethoxy-phenyl)-quinoxaline,
4-[3-(3,4-Dimethoxy-phenyl)-quinoxalin-5-yl]-N-methyl-benzenesulfonamide,
2-(3,4-Dimethoxy-phenyl)-8-(4-methanesulfonyl-phenyl)-quinoxaline,
2-(3,4-Diethoxy-phenyl)-8-(4-methylsulfanylmethyl-phenyl)-quinoxaline,
2-(3,4-Diethoxy-phenyl)-8-(4-methanesulfonylmethyl-phenyl)-quinoxaline,
2-{4-[3-(3,4-Diethoxy-phenyl)-quinoxalin-5-yl]-phenyl}-1-morpholin-4-yl-ethanone,
2-{4-[3-(3,4-Diethoxy-phenyl)-quinoxalin-5-yl]-phenyl}-1-(1,1-dioxido-thiomorpholin-4-yl)-ethanone,
{4-[3-(3,4-Diethoxy-phenyl)-quinoxalin-5-yl]-2-fluoro-phenyl}-morpholin-4-yl-methanone,
N-{4-[3-(3,4-Diethoxy-phenyl)-quinoxalin-5-yl]-phenyl}-methanesulfonamide,
2-{4-[3-(3,4-Diethoxy-phenyl)-quinoxalin-5-yl]-2-fluoro-phenyl}-1-morpholin-4-yl-ethanone,
{4-[3-(3,4-Diethoxy-phenyl)-quinoxalin-5-yl]-2-fluoro-phenyl}-(1,1-dioxido-thiomorpholin-4-yl)-methanone,
2-(3,4-Diethoxy-phenyl)-8-[4-(1,1-dioxido-thiomorpholin-4-ylmethyl)-3-methyl-phenyl]-quinoxaline,
8-(4-Ethanesulfonyl-phenyl)-2-[3-methoxy-4-(2-morpholin-4-yl-ethoxy)-phenyl]-quinoxaline,
2-(4-{3-[3-Methoxy-4-(2-morpholin-4-yl-ethoxy)-phenyl]-quinoxalin-5-yl}-phenyl)-1-morpholin-4-yl-ethanone,
(2-Fluoro-4-{3-[3-methoxy-4-(2-morpholin-4-yl-ethoxy)-phenyl]-quinoxalin-5-yl}-phenyl)-morpholin-4-yl-methanone,
N-(4-{3-[3-Methoxy-4-(2-morpholin-4-yl-ethoxy)-phenyl]-quinoxalin-5-yl}-phenyl)-methanesulfonamide,
8-(4-Methanesulfonylmethyl-phenyl)-2-[3-methoxy-4-(2-morpholin-4-yl-ethoxy)-phenyl]-quinoxaline,
N-(3-{8-[4-(2-Morpholin-4-yl-2-oxo-ethyl)-phenyl]-quinoxalin-2-yl}-phenyl)-methanesulfonamide,
N-{3-[8-(4-Ethanesulfonyl-phenyl)-quinoxalin-2-yl]-phenyl}-methanesulfonamide,
(4-{8-[4-(1,1-Dioxido-thiomorpholin-4-ylmethyl)-phenyl]-quinoxalin-2-yl}-2-methyl-phenyl)-(4-methyl-piperazin-1-yl)-methanone,
2-(4-{3-[3-Methyl-4-(4-methyl-piperazine-1-carbonyl)-phenyl]-quinoxalin-5-yl}-phenyl)-1-morpholin-4-yl-ethanone,
{4-[8-(3,5-Difluoro-4-morpholin-4-ylmethyl-phenyl)-quinoxalin-2-yl]-2-methyl-phenyl}-(4-methyl-piperazin-1-yl)-methanone,
(4-{8-[4-(1,1-Dioxido-thiomorpholin-4-ylmethyl)-3-methyl-phenyl]-quinoxalin-2-yl}-2-methyl-phenyl)-(4-methyl-piperazin-1-yl)-methanone,
(4-{8-[4-(1,1-Dioxido-thiomorpholin-4-ylmethyl)-3,5-difluoro-phenyl]-quinoxalin-2-yl}-2-methyl-phenyl)-(4-methyl-piperazin-1-yl)-methanone,
1-Morpholin-4-yl-2-{4-[3-(4-morpholin-4-yl-phenyl)-quinoxalin-5-yl]-phenyl}-ethanone,
{2-Methyl-4-[3-(4-morpholin-4-yl-phenyl)-quinoxalin-5-yl]-phenyl}-morpholin-4-yl-methanone,
8-(4-Ethanesulfonyl-phenyl)-2-[3-methoxy-4-(2-methoxy-ethoxy)-phenyl]-quinoxaline,
8-[4-(1,1-Dioxido-thiomorpholin-4-ylmethyl)-3-fluoro-phenyl]-2-[3-methoxy-4-(2-methoxy-ethoxy)-phenyl]-quinoxaline,
2-(2-Fluoro-4-{3-[3-methoxy-4-(2-methoxy-ethoxy)-phenyl]-quinoxalin-5-yl}-phenyl)-1-morpholin-4-yl-ethanone,
8-(3,5-Difluoro-4-morpholin-4-ylmethyl-phenyl)-2-[3-methoxy-4-(2-methoxy-ethoxy)-phenyl]-quinoxaline,
8-(3-Fluoro-4-morpholin-4-ylmethyl-phenyl)-2-[3-methoxy-4-(2-methoxy-ethoxy)-phenyl]-quinoxaline,
8-[4-(1,1-Dioxido-thiomorpholin-4-ylmethyl)-3-methyl-phenyl]-2-[3-methoxy-4-(2-methoxy-ethoxy)-phenyl]-quinoxaline,
8-[4-(1,1-Dioxido-thiomorpholin-4-ylmethyl)-3,5-difluoro-phenyl]-2-[3-methoxy-4-(2-methoxy-ethoxy)-phenyl]-quinoxaline,
4-{8-[4-(1,1-Dioxido-thiomorpholin-4-ylmethyl)-3-fluoro-phenyl]-quinoxalin-2-yl}-2,N,N-trimethyl-benzamide,
2,N,N-Trimethyl-4-[8-(4-morpholin-4-ylmethyl-3-trifluoromethyl-phenyl)-quinoxalin-2-yl]-benzamide,
4-[8-(3-Fluoro-4-morpholin-4-ylmethyl-phenyl)-quinoxalin-2-yl]-2,N,N-trimethyl-benzamide,
(4-{8-[4-(1,1-Dioxido-thiomorpholin-4-ylmethyl)-3-methyl-phenyl]-quinoxalin-2-yl}-2-methyl-phenyl)-morpholin-4-yl-methanone,
{4-[8-(3-Fluoro-4-morpholin-4-ylmethyl-phenyl)-quinoxalin-2-yl]-2-methyl-phenyl}-morpholin-4-yl-methanone,
{4-[8-(3,5-Difluoro-4-morpholin-4-ylmethyl-phenyl)-quinoxalin-2-yl]-2-methyl-phenyl}-morpholin-4-yl-methanone,
{2-Methyl-4-[8-(3-methyl-4-morpholin-4-ylmethyl-phenyl)-quinoxalin-2-yl]-phenyl}-morpholin-4-yl-methanone,
(4-{8-[3-Chloro-4-(1,1-dioxido-thiomorpholin-4-ylmethyl)-phenyl]-quinoxalin-2-yl}-2-methyl-phenyl)-morpholin-4-yl-methanone,
(4-{8-[4-(1,1-Dioxido-thiomorpholin-4-ylmethyl)-3-fluoro-phenyl]-quinoxalin-2-yl}-2-methyl-phenyl)-morpholin-4-yl-methanone,
(4-{8-[4-(1,1-Dioxido-thiomorpholin-4-ylmethyl)-phenyl]-quinoxalin-2-yl}-2-methyl-phenyl)-morpholin-4-yl-methanone,
(4-{8-[4-(1,1-Dioxido-thiomorpholin-4-ylmethyl)-3,5-difluoro-phenyl]yl}-2-methyl-phenyl)-morpholin-4-yl-methanone, {4-[8-(3-Fluoro-4-morpholin-4-ylmethyl-phenyl)-quinoxalin-2-yl]-2-methyl-phenyl}-pyrrolidin-1-yl-methanone,
{4-[8-(3,5-Difluoro-4-morpholin-4-ylmethyl-phenyl)-quinoxalin-2-yl]-2-methyl-phenyl}-pyrrolidin-1-yl-methanone,
(4-{8-[3-Chloro-4-(1,1-dioxido-thiomorpholin-4-ylmethyl)-phenyl]-quinoxalin-2-yl}-2-methyl-phenyl)-pyrrolidin-1-yl-methanone,
(2-Methyl-4-{3-[3-methyl-4-(pyrrolidine-1-carbonyl)-phenyl]-quinoxalin-5-yl}-phenyl)-pyrrolidin-1-yl-methanone,
1-(1,1-Dioxido-thiomorpholin-4-yl)-2-{2-fluoro-4-[3-(3-methyl-4-morpholin-4-ylmethyl-phenyl)-quinoxalin-5-yl]-phenyl}-ethanone,
8-[4-(1,1-Dioxido-thiomorpholin-4-ylmethyl)-3-methyl-phenyl]-2-(3-methyl-4-morpholin-4-ylmethyl-phenyl)-quinoxaline,
8-(3,5-Difluoro-4-morpholin-4-ylmethyl-phenyl)-2-(3-methyl-4-morpholin-4-ylmethyl-phenyl)-quinoxaline,
1-(1,1-Dioxido-thiomorpholin-4-yl)-2-{2-fluoro-4-[3-(4-imidazol-1-ylmethyl-3-methyl-phenyl)-quinoxalin-5-yl]-phenyl}-ethanone,
(1,1-Dioxido-thiomorpholin-4-yl)-(2-fluoro-4-{3-[4-(3-morpholin-4-yl-propoxy)-phenyl]-quinoxalin-5-yl}-phenyl)-methanone,
1-Morpholin-4-yl-2-(4-{3-[4-(3-morpholin-4-yl-propoxy)-phenyl]-quinoxalin-5-yl}-phenyl)-ethanone,
(2-Fluoro-4-{3-[4-(3-morpholin-4-yl-propoxy)-phenyl]-quinoxalin-5-yl}-phenyl)-morpholin-4-yl-methanone,
2-(2-Fluoro-4-{3-[3-methyl-4-(3-morpholin-4-yl-propoxy)-phenyl]-quinoxalin-5-yl}-phenyl)-1-morpholin-4-yl-ethanone,
4-[8-(4-Ethanesulfonyl-phenyl)-quinoxalin-2-yl]-2-methoxy-phenol,
2-{4-[7-Fluoro-3-(3,4,5-trimethoxy-phenyl)-quinoxalin-5-yl]-phenyl}-1-morpholin-4-yl-ethanone,
{4-[7-Methyl-3-(3,4,5-trimethoxy-phenyl)-quinoxalin-5-yl]-phenyl}-morpholin-4-yl-methanone,
(4-Ethyl-piperazin-1-yl)-(2-methyl-4-{8-[3-methyl-4-(1-methyl-1-morpholin-4-yl-ethyl)-phenyl]-quinoxalin-2-yl}-phenyl)-methanone,
[4-(8-{4-[1-(1,1-Dioxido-thiomorpholin-4-yl)-1-methyl-ethyl]-3-methyl-phenyl}-quinoxalin-2-yl)-2-methyl-phenyl]-(4-ethyl-piperazin-1-yl)-methanone,
{4-[8-(3,5-Difluoro-4-morpholin-4-ylmethyl-phenyl)-quinoxalin-2-yl]-2-methyl-phenyl}-(4-ethyl-piperazin-1-yl)-methanone,
2-(4-{3-[3-Methoxy-4-(3-morpholin-4-yl-propoxy)-phenyl]-quinoxalin-5-yl}-phenyl)-1-morpholin-4-yl-ethanone,
8-(3,5-Difluoro-4-morpholin-4-ylmethyl-phenyl)-2-[3-methoxy-4-(3-morpholin-4-yl-propoxy)-phenyl]-quinoxaline,
8-[4-(1,1-Dioxido-thiomorpholin-4-ylmethyl)-3-fluoro-phenyl]-2-[3-methoxy-4-(3-morpholin-4-yl-propoxy)-phenyl]-quinoxaline,
8-[4-(1,1-Dioxido-thiomorpholin-4-ylmethyl)-3,5-difluoro-phenyl]-2-[3-methoxy-4-(3-morpholin-4-yl-propoxy)-phenyl]-quinoxaline,
8-(3,5-Difluoro-4-morpholin-4-ylmethyl-phenyl)-2-[4-(4-methyl-piperazin-1-yl)-phenyl]-quinoxaline,
2-(2-Fluoro-4-{3-[4-(4-methyl-piperazin-1-yl)-phenyl]-quinoxalin-5-yl}-phenyl)-1-morpholin-4-yl-ethanone,
(2,6-Difluoro-4-{3-[4-(4-methyl-piperazin-1-yl)-phenyl]-quinoxalin-5-yl}-phenyl)-morpholin-4-yl-methanone,
8-[4-(1,1-Dioxido-thiomorpholin-4-ylmethyl)-3,5-difluoro-phenyl]-2-[4-(4-methyl-piperazin-1-yl)-phenyl]-quinoxaline,
8-[4-(1,1-Dioxido-thiomorpholin-4-ylmethyl)-phenyl]-2-[4-(4-methyl-piperazin-1-yl)-phenyl]-quinoxaline,
8-(3,5-Difluoro-4-morpholin-4-ylmethyl-phenyl)-2-[4-(4-ethyl-piperazin-1-ylmethyl)-3-methyl-phenyl]-quinoxaline,
2-[4-(4-Ethyl-piperazin-1-ylmethyl)-3-methyl-phenyl]-8-(3-fluoro-4-morpholin-4-ylmethyl-phenyl)-quinoxaline,
4-[8-(3,5-Difluoro-4-morpholin-4-ylmethyl-phenyl)-quinoxalin-2-yl]-N-(2-dimethylamino-ethyl)-2,N-dimethyl-benzamide,
N-(2-Dimethylamino-ethyl)-4-{8-[4-(1,1-dioxido-thiomorpholin-4-ylmethyl)-3,5-difluoro-phenyl]-quinoxalin-2-yl}-2,N-dimethyl-benzamide,
8-[4-(1,1-Dioxido-thiomorpholin-4-ylmethyl)-3,5-difluoro-phenyl]-2-(1-piperidin-4-yl-1H-pyrazol-4-yl)-quinoxaline,
{2,6-Difluoro-4-[3-(1-piperidin-4-yl-1H-pyrazol-4-yl)-quinoxalin-5-yl]-phenyl}-morpholin-4-yl-methanone,
8-(3,5-Difluoro-4-morpholin-4-ylmethyl-phenyl)-2-(1-piperidin-4-yl-1H-pyrazol-4-yl)-quinoxaline,
8-(3-Fluoro-4-methanesulfonyl-phenyl)-2-(1-piperidin-4-yl-1H-pyrazol-4-yl)-quinoxaline,
{2-Methyl-4-[3-(1-piperidin-4-yl-1H-pyrazol-4-yl)-quinoxalin-5-yl]-phenyl}-morpholin-4-yl-methanone,
{4-[8-(3,5-Difluoro-4-morpholin-4-ylmethyl-phenyl)-quinoxalin-2-yl]-2-methyl-phenyl}-(4-dimethylamino-piperidin-1-yl)-methanone,
(4-Dimethylamino-piperidin-1-yl)-(4-{8-[4-(1,1-dioxido-thiomorpholin-4-ylmethyl)-3,5-difluoro-phenyl]-quinoxalin-2-yl}-2-methyl-phenyl)-methanone,
8-(3,5-Difluoro-4-morpholin-4-ylmethyl-phenyl)-2-[4-(4-ethyl-piperazin-1-yl)-3-methyl-phenyl]-quinoxaline,
8-(3,5-Difluoro-4-morpholin-4-ylmethyl-phenyl)-2-[3-methoxy-4-(4-methyl-piperazin-1-yl)-phenyl]-quinoxaline,
(4-{3-[3-Methoxy-4-(4-methyl-piperazin-1-yl)-phenyl]-quinoxalin-5-yl}-2-methyl-phenyl)-morpholin-4-yl-methanone,
8-[4-(1,1-Dioxido-thiomorpholin-4-ylmethyl)-3,5-difluoro-phenyl]-2-(2-methoxy-pyridin-4-yl)-quinoxaline,
8-(3,5-Difluoro-4-morpholin-4-ylmethyl-phenyl)-2-[6-(4-methyl-piperazin-1-yl)-pyridin-3-yl]-quinoxaline,
8-[4-(1,1-Dioxido-thiomorpholin-4-ylmethyl)-3,5-difluoro-phenyl]-2-[6-(4-methyl-piperazin-1-yl)-pyridin-3-yl]-quinoxaline,
8-[4-(1,1-Dioxido-thiomorpholin-4-ylmethyl)-phenyl]-2-[6-(4-methyl-piperazin-1-yl)-pyridin-3-yl]-quinoxaline,
5-[8-(3,5-Difluoro-4-morpholin-4-ylmethyl-phenyl)-quinoxalin-2-yl]-pyridine-2-carboxylic acid (2-dimethylamino-ethyl)-methyl-amide,
5-{8-[4-(1,1-Dioxido-thiomorpholin-4-ylmethyl)-3,5-difluoro-phenyl]-quinoxalin-2-yl}-pyridine-2-carboxylic acid (2-dimethylamino-ethyl)-methyl-amide,
5-[8-(3,5-Difluoro-4-morpholin-4-ylmethyl-phenyl)-quinoxalin-2-yl]-3-methyl-pyridine-2-carboxylic acid (2-dimethylamino-ethyl)-methyl-amide,
5-{8-[4-(1,1-Dioxido-thiomorpholin-4-ylmethyl)-3,5-difluoro-phenyl]-quinoxalin-2-yl}-3-methyl-pyridine-2-carboxylic acid (2-dimethylamino-ethyl)-methyl-amide, (2-Methyl-4-{3-[1-(3-morpholin-4-yl-propyl)-1H-pyrazol-4-yl]-quinoxalin-5-yl}-phenyl)-morpholin-4-yl-methanone,
8-(3,5-Difluoro-4-morpholin-4-ylmethyl-phenyl)-2-[1-(2-methoxy-ethyl)-1H-pyrazol-4-yl]-quinoxaline,
2-(1-Azetidin-3-yl-1H-pyrazol-4-yl)-8-(3,5-difluoro-4-morpholin-4-ylmethyl-phenyl)-quinoxaline,
8-(3,5-Difluoro-4-morpholin-4-ylmethyl-phenyl)-2-[1-(tetrahydro-pyran-4-yl)-1H-pyrazol-4-yl]-quinoxaline,
4-(2,6-Difluoro-4-{3-[1-(tetrahydro-pyran-4-yl)-1H-pyrazol-4-yl]-quinoxalin-5-yl}-benzyl)-piperazin-2-one,
(2,6-Difluoro-4-{3-[1-(tetrahydro-pyran-4-yl)-1H-pyrazol-4-yl]-quinoxalin-5-yl}-phenyl)-morpholin-4-yl-methanone,
4-[8-(3,5-Difluoro-4-morpholin-4-ylmethyl-phenyl)-quinoxalin-2-yl]-N-(2-hydroxy-ethyl)-2-methyl-benzamide,
1-(4-{4-[8-(3,5-Difluoro-4-morpholin-4-ylmethyl-phenyl)-quinoxalin-2-yl]-pyrazol-1-yl}-piperidin-1-yl)-ethanone,
4-{4-[8-(3,5-Difluoro-4-morpholin-4-ylmethyl-phenyl)-quinoxalin-2-yl]-pyrazol-1-yl}-piperidine-1-carboxylic acid 2-methoxy-ethyl ester,
8-(3,5-Difluoro-4-morpholin-4-ylmethyl-phenyl)-2-{1-[1-(2-methoxy-ethyl)-piperidin-4-yl]-1H-pyrazol-4-yl}-quinoxaline,
4-{4-[8-(3,5-Difluoro-4-morpholin-4-ylmethyl-phenyl)-quinoxalin-2-yl]-5-methyl-pyrazol-1-yl}-piperidine-1-carboxylic acid tert-butyl ester,
8-(3,5-Difluoro-4-morpholin-4-ylmethyl-phenyl)-2-(5-methyl-1-piperidin-4-yl-1H-pyrazol-4-yl)-quinoxaline,
4-{4-[8-(3,5-Difluoro-4-morpholin-4-ylmethyl-phenyl)-quinoxalin-2-yl]-3-methyl-pyrazol-1-yl}-piperidine-1-carboxylic acid tert-butyl ester,
8-(3,5-Difluoro-4-morpholin-4-ylmethyl-phenyl)-2-(3-methyl-1-piperidin-4-yl-1H-pyrazol-4-yl)-quinoxaline,
2-[1-(1-Cyclopropyl-piperidin-4-yl)-1H-pyrazol-4-yl]-8-(3,5-difluoro-4-morpholin-4-ylmethyl-phenyl)-quinoxaline,
Cyclopropyl-(4-{4-[8-(3,5-difluoro-4-morpholin-4-ylmethyl-phenyl)-quinoxalin-2-yl]-pyrazol-1-yl}-piperidin-1-yl)-methanone,
4-{4-[8-(3,5-Difluoro-4-morpholin-4-ylmethyl-phenyl)-quinoxalin-2-yl]-pyrazol-1-yl}-piperidine-1-carboxylic acid methyl ester,
1-(4-{4-[8-(3,5-Difluoro-4-morpholin-4-ylmethyl-phenyl)-quinoxalin-2-yl]-3-methyl-pyrazol-1-yl}-piperidin-1-yl)-2-methyl-propan-1-one,
4-{4-[8-(3,5-Difluoro-4-morpholin-4-ylmethyl-phenyl)-quinoxalin-2-yl]-pyrazol-1-ylmethyl}-piperidine-1-carboxylic acid tert-butyl ester,
8-(3,5-Difluoro-4-morpholin-4-ylmethyl-phenyl)-2-(1-piperidin-4-ylmethyl-1H-pyrazol-4-yl)-quinoxaline,
(rac)-3-{4-[8-(3,5-Difluoro-4-morpholin-4-ylmethyl-phenyl)-quinoxalin-2-yl]-pyrazol-1-ylmethyl}-piperidine-1-carboxylic acid tert-butyl ester,
(rac)-8-(3,5-Difluoro-4-morpholin-4-ylmethyl-phenyl)-2-(1-piperidin-3-ylmethyl-1H-pyrazol-4-yl)-quinoxaline,
4-{4-[8-(3,5-Difluoro-4-morpholin-4-ylmethyl-phenyl)-quinoxalin-2-yl]-pyrazol-1-yl}-piperidine-1-carboxylic acid tert-butyl ester,
4-{4-[8-(4-Methanesulfonyl-phenyl)-quinoxalin-2-yl]-pyrazol-1-yl}-piperidine-1-carboxylic acid tert-butyl ester,
4-{4-[8-(3-Fluoro-4-morpholin-4-ylmethyl-phenyl)-quinoxalin-2-yl]-pyrazol-1-yl}-piperidine-1-carboxylic acid tert-butyl ester,
4-{4-[8-(3-Methyl-4-morpholin-4-ylmethyl-phenyl)-quinoxalin-2-yl]-pyrazol-1-yl}-piperidine-1-carboxylic acid tert-butyl ester,
4-{4-[8-(2-Methyl-4-morpholin-4-ylmethyl-phenyl)-quinoxalin-2-yl]-pyrazol-1-yl}-piperidine-1-carboxylic acid tert-butyl ester,
4-(4-{8-[4-(1,1-Dioxido-thiomorpholin-4-ylmethyl)-phenyl]-quinoxalin-2-yl}-pyrazol-1-yl)-piperidine-1-carboxylic acid tert-butyl ester,
4-(4-{8-[4-(1,1-Dioxido-thiomorpholin-4-ylmethyl)-2-methyl-phenyl]-quinoxalin-2-yl}-pyrazol-1-yl)-piperidine-1-carboxylic acid tert-butyl ester,
4-{4-[8-(4-Morpholin-4-ylmethyl-phenyl)-quinoxalin-2-yl]-pyrazol-1-yl}-piperidine-1-carboxylic acid tert-butyl ester,
8-(4-Methanesulfonyl-phenyl)-2-(1-piperidin-4-yl-1H-pyrazol-4-yl)-quinoxaline,
8-(3-Fluoro-4-morpholin-4-ylmethyl-phenyl)-2-(1-piperidin-4-yl-1H-pyrazol-4-yl)-quinoxaline,
8-(3-Methyl-4-morpholin-4-ylmethyl-phenyl)-2-(1-piperidin-4-yl-1H-pyrazol-4-yl)-quinoxaline,
8-(2-Methyl-4-morpholin-4-ylmethyl-phenyl)-2-(1-piperidin-4-yl-1H-pyrazol-4-yl)-quinoxaline,
8-[4-(1,1-Dioxido-thiomorpholin-4-ylmethyl)-phenyl]-2-(1-piperidin-4-yl-1H-pyrazol-4-yl)-quinoxaline,
8-[4-(1,1-Dioxido-thiomorpholin-4-ylmethyl)-2-methyl-phenyl]-2-(1-piperidin-4-yl-1H-pyrazol-4-yl)-quinoxaline,
8-(4-Morpholin-4-ylmethyl-phenyl)-2-(1-piperidin-4-yl-1H-pyrazol-4-yl)-quinoxaline,
4-{4-[8-(3,5-Difluoro-4-morpholin-4-ylmethyl-phenyl)-quinoxalin-2-yl]-3,5-dimethyl-pyrazol-1-yl}-piperidine-1-carboxylic acid tert-butyl ester,
4-{3,5-Dimethyl-4-[8-(4-morpholin-4-ylmethyl-phenyl)-quinoxalin-2-yl]-pyrazol-1-yl}-piperidine-1-carboxylic acid tert-butyl ester,
4-(4-{8-[4-(1,1-Dioxido-thiomorpholin-4-ylmethyl)-phenyl]-quinoxalin-2-yl}-3,5-dimethyl-pyrazol-1-yl)-piperidine-1-carboxylic acid tert-butyl ester,
4-{3,5-Dimethyl-4-[8-(3-methyl-4-morpholin-4-ylmethyl-phenyl)-quinoxalin-2-yl]-pyrazol-1-yl}-piperidine-1-carboxylic acid tert-butyl ester,
8-(3,5-Difluoro-4-morpholin-4-ylmethyl-phenyl)-2-(3,5-dimethyl-1-piperidin-4-yl-1H-pyrazol-4-yl)-quinoxaline,
2-(3,5-Dimethyl-1-piperidin-4-yl-1H-pyrazol-4-yl)-8-(4-morpholin-4-ylmethyl-phenyl)-quinoxaline,
2-(3,5-Dimethyl-1-piperidin-4-yl-1H-pyrazol-4-yl)-8-[4-(1,1-dioxido-thiomorpholin-4-ylmethyl)-phenyl]-quinoxaline,
2-(3,5-Dimethyl-1-piperidin-4-yl-1H-pyrazol-4-yl)-8-(3-methyl-4-morpholin-4-ylmethyl-phenyl)-quinoxaline,
(rac)-3-{4-[8-(3,5-Difluoro-4-morpholin-4-ylmethyl-phenyl)-quinoxalin-2-yl]-pyrazol-1-yl}-piperidine-1-carboxylic acid tert-butyl ester,
(rac)-8-(3,5-Difluoro-4-morpholin-4-ylmethyl-phenyl)-2-(1-piperidin-3-yl-1H-pyrazol-4-yl)-quinoxaline,
8-[4-(1,1-Dioxido-thiomorpholin-4-ylmethyl)-phenyl]-2-[4-methoxy-3-(4-methyl-piperazin-1-yl)-phenyl]-quinoxaline, 8-(3,5-Difluoro-4-morpholin-4-ylmethyl-phenyl)-2-[4-methoxy-3-(4-methyl-piperazin-1-yl)-phenyl]-quinoxaline, 8-[4-(1,1-Dioxido-thiomorpholin-4-ylmethyl)-3,5-difluoro-phenyl]-2-[4-methoxy-3-(4-methyl-piperazin-1-yl)-phenyl]-quinoxaline, {3-[8-(3,5-Difluoro-4-morpholin-4-ylmethyl-phenyl)-quinoxalin-2-yl]-phenyl}-(4-methyl-piperazin-1-yl)-methanone, (3-{8-[4-(1,1-Dioxido-thiomorpholin-4-ylmethyl)-phenyl]-quinoxalin-2-yl}-phenyl)-(4-methyl-piperazin-1-yl)-methanone, (3-{8-[4-(1,1-Dioxido-thiomorpholin-4-ylmethyl)-3,5-difluoro-phenyl]-quinoxalin-2-yl}-phenyl)-(4-methyl-piperazin-1-yl)-methanone, {4-[8-(3,5-Difluoro-4-morpholin-4-ylmethyl-phenyl)-quinoxalin-2-yl]-1-methyl-1H-pyrrol-2-yl}-(4-methyl-piperazin-1-yl)-methanone, (4-{8-[4-(1,1-Dioxido-thiomorpholin-4-ylmethyl)-3,5-difluoro-phenyl]-quinoxalin-2-yl}-1-methyl-1H-pyrrol-2-yl)-(4-methyl-piperazin-1-yl)-methanone, 8-[4-(1,1-Dioxido-thiomorpholin-4-ylmethyl)-3,5-difluoro-phenyl]-2-(3-piperazin-1-yl-phenyl)-quinoxaline, and 8-[4-(1,1-Dioxido-thiomorpholin-4-ylmethyl)-3,5-difluoro-phenyl]-2-[3-(4-methyl-piperazin-1-yl)-phenyl]-quinoxaline; or a pharmaceutically acceptable salt thereof.

\* \* \* \* \*